(12) United States Patent
Muyldermans et al.

(10) Patent No.: US 9,156,905 B2
(45) Date of Patent: Oct. 13, 2015

(54) FUNCTIONAL HEAVY CHAIN ANTIBODIES, FRAGMENTS THEREOF, LIBRARY THEREOF AND METHODS OF PRODUCTION THEREOF

(75) Inventors: Serge Muyldermans, Hoelaart (BE); Viet Khong Nguyen, Hanoi (VN)

(73) Assignee: VIB vzw, Zwijnaarde (BE)

( * ) Notice: Subject to any disclaimer, the term of this patent is extended or adjusted under 35 U.S.C. 154(b) by 0 days.

(21) Appl. No.: 12/498,835

(22) Filed: Jul. 7, 2009

(65) Prior Publication Data

US 2010/0047241 A1 Feb. 25, 2010

Related U.S. Application Data

(63) Continuation of application No. 11/474,521, filed on Jun. 23, 2006, now Pat. No. 8,097,251, which is a continuation of application No. 10/492,668, filed as application No. PCT/EP02/07804 on Jul. 12, 2002, now abandoned.

(60) Provisional application No. 60/335,054, filed on Oct. 24, 2001.

(30) Foreign Application Priority Data

Oct. 24, 2001 (GB) .................................. 01204037.4
Jan. 11, 2002 (JP) .................................. 2002-004184

(51) Int. Cl.
| | | |
|---|---|---|
| A61K 39/395 | (2006.01) | |
| C07K 16/30 | (2006.01) | |
| C07K 16/00 | (2006.01) | |
| C07K 16/24 | (2006.01) | |
| A61K 39/00 | (2006.01) | |

(52) U.S. Cl.
CPC ............. *C07K 16/005* (2013.01); *C07K 16/241* (2013.01); *C07K 16/3007* (2013.01); *A61K 2039/505* (2013.01); *C07K 2317/21* (2013.01); *C07K 2317/22* (2013.01); *C07K 2317/56* (2013.01); *C07K 2317/569* (2013.01); *C07K 2317/622* (2013.01); *C07K 2319/22* (2013.01)

(58) Field of Classification Search
None
See application file for complete search history.

(56) References Cited

U.S. PATENT DOCUMENTS

| | | | |
|---|---|---|---|
| 5,530,101 A | 6/1996 | Queen et al. | |
| 6,262,238 B1 | 7/2001 | Steipe et al. | |
| 6,670,453 B2 | 12/2003 | Frenken et al. | |
| 7,084,257 B2 | 8/2006 | Deshpande et al. | |
| 7,229,619 B1 * | 6/2007 | Young et al. ............... | 424/159.1 |
| 7,368,111 B2 | 5/2008 | Thompson et al. | |
| 7,432,238 B2 | 10/2008 | Kisiel et al. | |
| 8,097,251 B2 * | 1/2012 | Muyldermans et al. ... | 424/133.1 |
| 8,188,223 B2 | 5/2012 | Beirnaert et al. | |
| 8,282,924 B2 | 10/2012 | Rother et al. | |
| 8,703,131 B2 | 4/2014 | Beirnaert | |
| 2002/0001587 A1 | 1/2002 | Erickson et al. | |
| 2002/0165387 A1 | 11/2002 | Kerr Anderson et al. | |
| 2003/0099655 A1 | 5/2003 | Watkins et al. | |
| 2003/0129659 A1 | 7/2003 | Whelihan et al. | |
| 2004/0071705 A1 | 4/2004 | Sato et al. | |
| 2005/0054001 A1 * | 3/2005 | Muyldermans ................ | 435/7.1 |
| 2005/0271663 A1 | 12/2005 | Ignatovich et al. | |
| 2006/0034845 A1 | 2/2006 | Silence et al. | |
| 2006/0106203 A1 | 5/2006 | Winter et al. | |
| 2006/0228355 A1 | 10/2006 | Laeremans et al. | |
| 2007/0031424 A1 * | 2/2007 | Muyldermans ............ | 424/155.1 |
| 2007/0077249 A1 | 4/2007 | Silence et al. | |
| 2007/0178082 A1 | 8/2007 | Silence et al. | |
| 2007/0237769 A1 | 10/2007 | Silence et al. | |
| 2007/0269422 A1 | 11/2007 | Beirnaert et al. | |
| 2008/0008713 A1 | 1/2008 | Brewis | |
| 2009/0022721 A1 | 1/2009 | Silence et al. | |
| 2009/0028880 A1 | 1/2009 | Beirnaert et al. | |
| 2009/0148434 A1 | 6/2009 | Tomlinson et al. | |
| 2010/0081792 A1 | 4/2010 | Grant et al. | |
| 2010/0297111 A1 | 11/2010 | Beirnaert | |
| 2011/0251373 A1 | 10/2011 | Muyldermans | |
| 2012/0172578 A1 | 7/2012 | Muyldermans | |

FOREIGN PATENT DOCUMENTS

| | | |
|---|---|---|
| EP | 93201239.6 | 4/1993 |
| EP | 0 584 421 A1 | 3/1994 |
| EP | 98300525.7 | 1/1998 |
| EP | 1399484 | 6/2001 |
| GB | 0115841.9 | 6/2001 |

(Continued)

OTHER PUBLICATIONS

De Pascalis et al. The Journal of Immunology (2002) 169, 3076-3084.*

(Continued)

*Primary Examiner* — Misook Yu
*Assistant Examiner* — Julie Wu
(74) *Attorney, Agent, or Firm* — Wolf, Greenfield & Sacks, P.C.

(57) ABSTRACT

The present invention relates to functional heavy chain antibodies, functional single domain heavy chain antibodies, functional VH domains, or functional fragments thereof comprising an amino acid which is neither a charged amino acid nor a C at position 45, and comprising an amino acid at position 103 independently chosen from the group consisting of R, G, K, S, Q, L, and P, and optionally an amino acid at position 108 independently chosen from the group consisting of Q, L and R, said positions determined according to the Kabat numbering.

10 Claims, 10 Drawing Sheets

(56) References Cited

FOREIGN PATENT DOCUMENTS

| JP | 62-175426 | 8/1987 |
|---|---|---|
| JP | 6-50256 | 3/1994 |
| WO | WO 92/01787 | 2/1992 |
| WO | WO 94/04678 A1 | 3/1994 |
| WO | WO 94/13804 | 6/1994 |
| WO | WO 94/25591 A1 | 11/1994 |
| WO | WO 99/20749 A2 | 4/1999 |
| WO | WO 99/37681 A2 | 7/1999 |
| WO | WO 99/42077 | 8/1999 |
| WO | WO 00/09757 A1 | 2/2000 |
| WO | WO 00/73430 A2 | 12/2000 |
| WO | WO 01/44301 A1 | 6/2001 |
| WO | WO 01/45746 A2 | 6/2001 |
| WO | WO 01/90190 A2 | 11/2001 |
| WO | WO 02/48193 A2 | 6/2002 |
| WO | WO 03/002609 A2 | 1/2003 |
| WO | WO 03/035694 A2 | 5/2003 |
| WO | WO 03/050531 A2 | 6/2003 |
| WO | WO 2004/001064 A2 | 12/2003 |
| WO | WO 2004/003019 A2 | 1/2004 |
| WO | WO 2004/003019 A3 | 1/2004 |
| WO | WO 2004/041862 A2 | 5/2004 |
| WO | WO 2005/035572 A2 | 4/2005 |
| WO | WO 2006/038027 A2 | 4/2006 |
| WO | WO 2006/059106 | 6/2006 |
| WO | WO 2007/049017 A2 | 5/2007 |
| WO | WO 2008/149144 A2 | 12/2008 |
| WO | WO 2008/149146 A2 | 12/2008 |
| WO | WO 2008/149147 A2 | 12/2008 |
| WO | WO 2008/149148 A2 | 12/2008 |
| WO | WO 2009/068627 A2 | 6/2009 |

OTHER PUBLICATIONS

Chen et al. J. Mol. Bio. (1999) 293, 865-881.*
Brummell et al. (Biochemistry 32:1180-1187 (1993)).*
Kobayashi et al. (Protein Engineering 12:879-844 (1999)).*
Burks et al. (PNAS 94:412-417 (1997)).*
Hasemann et al. (JBC 266(12):7627-7632 (1991)).*
Ibragimova and Eade (Biophysical Journal, Oct. 1999, vol. 77, pp. 2191-2198).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987)).*
Lin et al Biochemistry USA vol. 14:1559-1563 (1975)).*
Conrath et al., (Journal Antimicrobial Agents and Chemotherapy, Oct. 2001, vol. 45, No. 10, pp. 2807-2812, was received on Sep. 26, 2001 shown by the stamp from Virginia Tech).*
Harmsen et al., (Molecular Immunology, Aug. 2000, vol. 37, pp. 579-590).*
Desmyter et al., (The Journal of Biological Chemistry, 276, 26285-26290, First Published on May 7, 2001).*
Lefranc et al., (Developmental and Comparative Immunology 27 (2003) 55-77).*
U.S. Appl. No. 60/207,234, Tanha et al.
Ameloot et al., "Heterotrimers formed by tumor necrosis factors of different species or muteins," *J. Biol. Chem.* Jul. 20, 2001; 276(29):27098-103. Epub May 22, 2001.
Anker et al., "VH and VL region structure of antibodies that recognize the (NANP)3 dodecapeptide sequence in the circumsporozoite protein of *Plasmodium falciparum*," *Eur. J Immunol.* Dec. 1990; 20(12):2757-61.
Babu et al., "Omalizumab, a novel anti-IgE therapy in allergic disorders," *Expert Opin. Biol. Ther.* Nov. 2001; 1(6):1049-58.
Bodtger et al., "The safety and efficacy of subcutaneous birch pollen immunotherapy—a one-year, randomized, double-blind, placebo-controlled study," *Allergy* Apr. 2002; 57(4):297-305.
Brorson et al., *J. Immunol.* 1999; 163:6694-6701.

Carter et al., Structure of serum albumin. *Adv Protein Chem.* 1994;45:153-203. Review.
Casset et al., "A peptide mimetic of an anti-CD4 monoclonal antibody by rational design," *BBRC* 2003:198-205.
Chavez et al., "Antibody as an immunological probe for studying the refolding of bovine serum albumin. An immunochemical approach to the identification of possible nucleation sites." *J Biol Chem.* Nov. 25, 1978;253(22):8081-6.
Chikao et al., "Inhibition of *Helicobacter pylori* infection by orally administered yolk-derived anti-*Helicobacter pylori* antibody." *Hepatogastroenterology.* May-Jun. 2002;49(45):709-14. Abstract.
Chukwuocha et al., "Isolation, characterization and sequence analysis of five IgG monoclonal anti-beta 2-glycoprotein-1 and anti-prothrombin antigen-binding fragments generated by phage display," *J Immunol.* Oct. 15, 1999; 163(8): 4604-11.
Coleman, *Research in Immunol.* 1994; 145:33-36.
Conrath et al. "Camel Single-domain Antibodies as Modular Building Units in Bispecific and Bivalent Antibody Constructs," *The Journal of Biological Chemistry* 2001; 276(10):7346-7350.
Conrath et al., "Antigen binding and solubility effects upon the veneering of a camel VHH in framework-2 to mimic a VH." *J Mol Biol.* Jul. 1, 2005;350(1):112-25.
Conrath, K.E. et al., "Beta-Lactamase Inhibitors Derived from Single-Domain Antibody Fragments Elicited in the Camelidae," *Antimicrobial Agents and Chemotherapy* 2001; 45(10):2807-2812.
Coppieters et al., "Formatted anti-TNF-alpha nanobodies show superior efficacy in a collagen-induced arthritis model in mice." *Arthritis &Rheumatism.* Sep. 2005;52(9), Supp. S:S362-S363. Abstract 922.
Coppieters et al., "Formatted anti-tumor necrosis factor alpha VHH proteins derived from camelids show superior potency and targeting to inflamed joints in a murine model of collagen-induced arthritis." *Arthritis Rheum.* Jun. 2006;54(6):1856-66.
Davies, J. and Riechmann, L., "Single antibody domains as small recognition units: design and in vitro antigen selection of camelized, human VH domains with improved protein stability," *Protein Engineering* 1996; 9(6):531-37.
Dennis et al., "Albumin binding as a general strategy for improving the pharmacokinetics of proteins." *J Biol Chem.* Sep. 20, 2002;277(38):35035-43. Epub Jul. 15, 2002.
Desmyter, A. et al., "Antigen Specificity and High Affinity Binding Provided by One Single Loop of a Camel Single-domain Antibody," *The Journal of Biological Chemistry* Jul. 2001;276(28): 26285-290.
Dimasi et al., "Characterization of engineered hepatitis C virus NS3 protease inhibitors affinity selected from human pancreatic secretory trypsin inhibitor and minibody repertoires," *J Virol.* Oct. 1997; 71(10):7461-9.
Dufner, P. et al., "Harnessing phage and ribosome display for antibody optimization," *Trends in Biotechnology* 2006; 24(11):523-29.
Fan, Zhao-chang et al., "Three-dimensional Structure of an Fv from a Human IgM Immunoglobulin," *J Mol. Biol.* 1992; 228:188-207.
Ferguson et al, "Immunoregulatory properties of antigenic fragments from bovine serum albumin." *Cell Immunol.* May 1983;78(1):1-12.
Gordon et al., "A pilot study of treatment of active ulcerative colitis with natalizumab, a humanized monoclonal antibody to alpha-4 integrin," *Aliment Pharmacol Ther.* Apr. 2002; 16(4):699-705.
Harmsen, M.M. et al., "Properties, production, and applications of camelid single-domain antibody fragments," *Applied Microbiology and Biotechnology* 2007; 77:13-22.
Holm et al., "Functional mapping and single chain construction of the anti-cytokeratin 8 monoclonal antibody TS1," *Molec. Immunol.* 2007; 44:1075-1084.
Hommes et al., "Infliximab treatment for Crohn's disease: one-year experience in a Dutch academic hospital," *Inflamm Bowel Dis.* Mar. 2002; 8(2): 81-6.
Hoogenboom et al., "Multi-subunit proteins on the surface of filamentous phage: methodologies for displaying antibody (Fab) heavy and light chains," *Nucleic Acids Res.* Aug. 11, 1991; 19(15):4133-7.
Jang et al., *Molec. Immunol.* 1998; 35:1207-1217.
Klooster, R. et al., "Improved anti-IgG and HAS affinity ligands: Clinical application of VHH antibody technology," *Journal of Immunological Methods* 2007; 324:1-12.
Kumar et al., *J. Biol. Chem.* 2000; 275-35129-35136.

(56) References Cited

OTHER PUBLICATIONS

Lauwereys, M. et al., "Potent enzyme inhibitors derived from dromedary heavy-chain antibodies," *The EMBO Journal* 1998; 17(13):3512-20.
MacCallum et al., "Antibody-antigen interactions: contact analysis and binding site topography," *J. Mol. Biol.* 1996; 262:732-745.
Muyldermans et al., *Trends in Biochem. Sci.* Apr. 2001; 26:230-235.
Muyldermans, S. et al., "Unique single-domain antigen binding fragments derived from naturally occurring camel heavy-chain antibodies," *Journal of Molecular Recognition* 1999; 12:131-140.
Muyldermans, S., "Single domain camel antibodies: current status," *Reviews in Molecular Biotechnology* 2001; 74:277-302.
Nguyen et al., "Camel heavy-chain antibodies: diverse germline V(H)H and specific mechanisms enlarge the antigen-binding repertoire," *EMBO J.* Mar. 1, 2000; 19(5):921-30.
Nguyen, V.K., Thesis, "Generation of heavy chain antibodies in camelids," Free University of Brussels, Faculty of Science, Inst. For Molecular Biology and Biotechnology, Lab. of Ultrastructure (submitted Aug. 2001).
Nutall et al., "Immunoglobulin VH domains and beyond: design and selection of single-domain binding and targeting reagents," *Curr Pharm Biotechnol.* Nov. 2000; 1(3): 253-63.
Quiocho et al., "Protein engineering. Making of the minibody," *Nature* Mar. 25, 1993; 362(6418):293-4.
Riechman et al., "Single domain antibodies: comparison of camel VH and camelised human VH domains," *J. Immunol. Methods* 1999; 231(1-2):25-38.
Rudikoff et al., "Single amino acid substitution altering antigen-binding specificity," *Proc Natl Acad Sci USA* 1982; vol. 79, p. 1979.
Skurkovich et al., "Treatment of corneal transplant rejection in humans with anti-interferon-gamma antibodies." *Am J Ophthalmol.* Jun. 2002;133(6):829-30.
Smith-Gill et al., *J. Immunol.* 1987; 139:4135-4144.
Sollinger et al., "Basiliximab versus antithymocyte globulin for prevention of acute renal allograft rejection," *Transplantation* Dec. 27, 2001; 72(12):1915-9.
Song et al., *Biochem Biophys Res Comm* 2000; 268:390-394.
Spinelli et al., "The crystal structure of a llama heavy chain variable domain," *Nat Struct Biol.* Sep. 1996; 3(9):752-7.
Tang et al., "Stabilization of leucine zipper coiled coils by introduction of trifluoroleucine," *Abst Pap Am Chem.* 1999; 5218:U138. Abstract 416.
Teitelbaum et al., "A mAb recognizing a surface antigen of *Mycobacterium tuberculosis* enhances host survival." *Proc Natl Acad Sci U S A.* Dec. 22, 1998;95(26):15688-93.
Vajdos et al., "Comprehensive functional maps of the antigen-binding site of an anti-ErbB2 antibody obtained with shotgun scanning mutagensis," *J. Mol. Biol.* 2002; 320:415-428.
Vajdos, F.F. et al., "Comprehensive functional maps of the antigen-binding site of an anti-Erb2 antibody obtained with shotgun scanning mutagenesis," *Journal of Molecular Biology* 2002; 320:415-428.
Van Hest et al., "Efficient introduction of alkene functionality into proteins in vivo," *FEBS Lett.* May 22, 1998; 428(1-2):68-70.
Vu, et al., "Comparison of Llama $V_H$ Sequences from conventional and heavy chain antibodies," Molecular Immunology, vol. 34, No. 16-17, pp. 1121-1131 (1997).
Ward et al., "Binding activities of a repertoire of single immunoglobulin variable domains secreted from *Escherichia coli*," *Nature* Oct. 12, 1989; 341(6242):544-6.
Worledge et al., "Oral administration of avian tumor necrosis factor antibodies effectively treats experimental colitis in rats." *Dig Dis Sci.* Dec. 2000;45(12):2298-305.
Wu, H. et al., "Humanization of a murine monoclonal antibody by simultaneous optimization of framework and CDR residues," *Journal of Molecular Biology* 1999; 294:151-162.
Wunder et al., "Albumin-based drug delivery as novel therapeutic approach for rheumatoid arthritis." *J Immunol.* May 1, 2003;170(9):4793-801.
[No Author Listed]Fundamental Immunology, William E. Paul, MD, Ed. 3$^{rd}$ ed. 1993, p. 242.

Arbabi Ghahroudi et al., Selection and identification of single domain antibody fragments from camel heavy-chain antibodies. FEBS Lett. Sep. 15, 1997;414(3):521-6.
Black et al., Development of hydrophobicity parameters to analyze proteins which bear post-pr cotranslational modifications. Anal Biochem. Feb. 15, 1991;193(1):72-82.
Caldas et al., Humanization of the anti-CD18 antibody 6.7: an unexpected effect of a framework residue in binding to antigen. Mol Immunol. May 2003;39(15):941-52.
Chien et al., Significant structural and functional change of an antigen-binding site by a distant amino acid substitution: proposal of a structural mechanism. Proc Natl Acad Sci U S A. Jul. 1989;86(14):5532-6.
Chothia et al., Domain association in immunoglobulin molecules. The packing of variable domains. J Mol Biol. Dec. 5, 1985;186(3):651-63.
Cortez-Retamozo et al., Efficient cancer therapy with a nanobody-based conjugate. Cancer Res. Apr. 15, 2004;64(8):2853-7.
Desmyter et al., Crystal structure of a camel single-domain VH antibody fragment in complex with lysozyme. Nat Struct Biol. Sep. 1996;3(9):803-11.
Dumoulin et al., Single-domain antibody fragments with high conformational stability. Protein Sci. Mar. 2002;11(3):500-15.
Giusti et al., Somatic diversification of S107 from an antiphosphocholine to an anti-DNA autoantibody is due to a single base change in its heavy chain variable region. Proc Natl Acad Sci U S A. May 1987;84(9):2926-30.
Hamers-Casterman et al., Naturally occurring antibodies devoid of light chains. Nature. Jun. 3, 1993;363(6428):446-8.
Harmsen et al., Llama heavy-chain V regions consist of at least four distinct subfamilies revealing novel sequence features. Mol Immunol. Aug. 2000;37(10):579-90.
Janeway et al., Immunobiology, 3$^{rd}$ Ed. Garland Press, 1997, p. 3:7-3:11.
López-Requena et al., Gangliosides, Ab1 and Ab2 antibodies II. Light versus heavy chain: An idiotype-anti-idiotype case study. Mol Immunol. Feb. 2007;44(5):1015-28. Epub Apr. 18, 2006.
Mariuzza et al., The structural basis of antigen-antibody recognition. Annu Rev Biophys Biophys Chem. 1987;16:139-59. Review.
Muyldermans, Single domain camel antibodies: current status. J Biotechnol. Jun. 2001;74(4):277-302.
Nargessi et al., Solid-phase fluoroimmunoassay of human albumin in biological fluids. Clin Chim Acta. Nov. 1, 1978;89(3):455-60.
Pessi et al., A designed metal-binding protein with a novel fold. Nature. Mar. 25, 1993;362(6418):367-9.
Portolano et al., Lack of promiscuity in autoantigen-specific H and L chain combinations as revealed by human H and L chain "roulette". J Immunol. Feb. 1, 1993;150(3):880-7.
Rahbarizadeh et al., Production of novel recombinant single-domain antibodies against tandem repeat region of MUC1 mucin. Hybrid Hybridomics. Jun. 2004;23(3):151-9.
Reiter et al., An antibody single-domain phage display library of a native heavy chain variable region: isolation of functional single-domain VH molecules with a unique interface. J Mol Biol. Jul. 16, 1999;290(3):685-98.
Riechmann, Rearrangement of the former VL interface in the solution structure of a camelised, single antibody VH domain. J Mol Biol. Jun. 28, 1996;259(5):957-69.
Sheikh et al., Enhanced recognition of reactive oxygen species damaged human serum albumin by circulating systemic lupus erythematosus autoantibodies. Autoimmunity. Nov. 2007;40(7):512-20.
Smith et al., Prolonged in vivo residence times of antibody fragments associated with albumin. Bioconjug Chem. Sep.-Oct. 2001;12(5):750-6.
Tanha et al., Selection by phage display of llama conventional V(H) fragments with heavy chain antibody V(H)H properties. J Immunol Methods. May 1, 2002;263(1-2):97-109.
Van Der Linden et al., Comparison of physical chemical properties of llama VHH antibody fragments and mouse monoclonal antibodies. Biochim Biophys Acta. Apr. 12, 1999;1431(1):37-46.

(56) References Cited

OTHER PUBLICATIONS

Vincke et al., General strategy to humanize a camelid single-domain antibody and identification of a universal humanized nanobody scaffold. J Biol Chem. Jan. 30, 2009;284(5):3273-84. Epub Nov. 14, 2008.

Winkler et al., Changing the antigen binding specificity by single point mutations of an anti-p24 (HIV-1) antibody. J Immunol. Oct. 15, 2000;165(8):4505-14.

GENBANK Submission; NIH/NCBI, Accession No. AJ401076; Harmsen et al.; May 22, 2010.

GENBANK Submission; NIH/NCBI, Accession No. AJ401077; Harmsen et al.; May 22, 2010.

Holt et al., Anti-serum albumin domain antibodies for extending the half-lives of short lived drugs. Protein Eng Des Sel. May 2008;21(5):283-8. doi: 10.1093/protein/gzm067. Epub Apr. 2, 2008.

Roovers et al., Efficient inhibition of EGFR signaling and of tumour growth by antagonistic anti-EFGR Nanobodies. Cancer Immunol Immunother. Mar. 2007;56(3):303-317.

Stancovski et al., Mechanistic aspects of the opposing effects of monoclonal antibodies to the ERBB2 receptor on tumor growth. Proc Natl Acad Sci U S A. Oct. 1, 1991;88(19):8691-5.

Zhang et al., Site-directed mutational analysis of human tumor necrosis factor-alpha receptor binding site and structure-functional relationship. J Biol Chem. Nov. 25, 1992;267(33):24069-75.

[No author listed] Anti human IgG ligand for depletion of human plasma. Biotechnol App Centre. Sep. 2003. Product sheet 101-0822-V1.0. www.bac.nl. 2 pages.

[No author listed] Anti human serum albumin ligand for depletion of human plasma. Biotechnol App Centre. Sep. 2003. Product sheet 102-0826-V1.0. www.bac.nl. 2 pages.

[No author listed] BAC invoice (redacted) for 102-0822-03 CaptureSelect anti-human IgG ligand. Invoice No. S05-0006. Invoice date: Mar. 24, 2005. 1 page.

Krauss et al., Impact of antibody framework residue VH-71 on the stability of a humanised anti-MUC1 scFv and derived immunoenzyme. Br J Cancer. May 4, 2004;90(9):1863-70.

Pakula et al., Genetic analysis of protein stability and function. Annu Rev Genet. 1989;23:289-310. Summary only.

Roitt et al., Immunology. MIR. Moscow. 2000; p. 150. Russian with English Translation.

Hanauer et al., Maintenance infliximab for Crohn's disease: the ACCENT I randomised trial. Lancet. May 4, 2002;359(9317):1541-9.

Hu et al., Comparison of the inhibition mechanisms of adalimumab and infliximab in treating tumor necrosis factor α-associated diseases from a molecular view. J Biol Chem. Sep. 20, 2013;288(38):27059-67. doi: 10.1074/jbc.M113.491530. Epub Aug. 13, 2013.

Jones et al., Replacing the complementarity-determining regions in a human antibody with those from a mouse. Nature. 1986;321:522-25.

Sandborn et al., Antitumor necrosis factor therapy for inflammatory bowel disease: a review of agents, pharmacology, clinical results, and safety. Inflamm Bowel Dis. May 1999;5(2):119-33.

Shimamoto et al., Inhibition of *Helicobacter pylori* infection by orally administered yolk-derived anti-*Helicobacter pylori* antibody. Hepatogastroenterology. May-Jun. 2002;49(45):709-14. Database BIOSIS Abstract. Accession No. PREV200200382020.

* cited by examiner

Figure 1-1

(A) TEM04

```
  1 caggtgcagc tggtggagtc tgggggaggc ttggtgcagg ctggagggtc
tctgaggctc
        q  v  q    l  v  e  s    g  g  g    l  v  q  a    g  g  s  l  r  l 61 tcctgtgcag cctctggatt caccttcagt agcgcatgga tgacatgggt
ccgccaggct
        s  c  a    a  s  g  f    t  f  s    s  a  w    m  t  w  v  r  q  a 121 ccagggaagg gactcgagtg ggtcacaagt attgctacgg atgggtccac
ggactatgca
        p  g  k    g  l  e  w    v  t  s    i  a  t    d  g  s    t  d  y  a 181 gactccgtga agggccgatt caccatctcc agagacaatg ccaagaacac
gctgtatctg
        d  s  v    k  g  r  f    t  i  s    r  d  n    a  k  n    t  l  y  l 241 caattaaaca gcctgaacac tgaagacacg gccgtgtatt actgtgcaaa
agatcgttgg
        q  l  n    s  l  n  t    e  d  t    a  v  y    y  c  a    k  d  r  w 301 gggtatgtcg taagaggcca ggggacccag gtcaccgtct cctca
        g  y  v    v  r  g  q    g  t  q    v  t  v    s  s
```

AGA = wild type

TGG = mutant

Figure 1-2

(B) CEA71

```
  1  caggtgcagc tggtggagtc tgggggaggc ttggtgcaac ctggggggtc
tctgagactc
        q  v  q  l  v  e  s  g  g  l  v  q  p  g  g  s  l  r  l 61  tcctgtgcag cctctggatt caccttcagt agcagctaca tgagctgggt
ccgccaggct
        s  c  a  a  s  g  f  t  f  s  s  s  y  m  s  w  v  r  q  a 121  ccagggaagg ggctggagtg ggtgtccggc attaataccg atggaagttt
cacgcgctat
        p  g  k  g  l  e  w  v  s  g  i  n  t  d  g  s  f  t  r  y 181  gccgactccg tgaagggccg attcaccatc tccagagaca acgccaagaa
cacgctgtat
        a  d  s  v  k  g  r  f  t  i  s  r  d  n  a  k  n  t  l  y 241  ctgcaaatga acagcctgaa atctgaggac acggccctgt attactgtgc
cgtaggcggc
        l  q  m  n  s  l  k  s  e  d  t  a  l  y  y  c  a  v  g  g 301  gggttaggct atggccccag gggccagggg accctggtca ctgtctcctc a
        g  l  g  y  g  p  r  g  q  g  t  l  v  t  v  s  s
```

AGG = wild type

TGG = mutant

Figure 6-1

| SEQ ID NO: | Position #45 | Position #103 | Position #108 |
|---|---|---|---|
| 1 | Not charged, and not C | G | Q |
| 2 | Not charged, and not C | G | R |
| 3 | Not charged, and not C | K | R |
| 4 | Not charged, and not C | L | R |
| 5 | Not charged, and not C | P | L |
| 6 | Not charged, and not C | P | R |
| 7 | Not charged, and not C | Q | L |
| 8 | Not charged, and not C | Q | R |
| 9 | Not charged, and not C | S | L |
| 10 | Not charged, and not C | S | R |

SEQ ID NO: 13    RGQGTQ
SEQ ID NO: 14    RGKGTQ
SEQ ID NO: 15    VXXXXXXGLXW
SEQ ID NO: 16    LGQGTQVTVSS
SEQ ID NO: 17    QGQGTGVTVSS
SEQ ID NO: 18    PGQGTQVTVSS
SEQ ID NO: 19    SSQGTQVTVSS

| SEQ ID NO: | Position #45 | Position #103 | Position #108 |
|---|---|---|---|
| 20 | P | G | Q |
| 21 | V | G | Q |
| 22 | S | G | Q |
| 23 | L | G | Q |
| 24 | M | G | Q |
| 25 | W | G | R |
| 26 | A | G | R |
| 27 | T | G | R |
| 28 | G | G | R |
| 29 | F | G | R |
| 30 | A | K | R |
| 31 | F | K | R |
| 32 | M | K | R |
| 33 | I | K | R |
| 34 | P | K | R |
| 35 | V | L | R |
| 36 | I | L | R |
| 37 | F | L | R |
| 38 | Y | L | R |
| 39 | T | L | R |
| 40 | L | P | L |

Figure 6-2

| | | | |
|---|---|---|---|
| 41 | I | P | L |
| 42 | P | P | L |
| 43 | V | P | L |
| 44 | W | P | L |
| 45 | G | P | R |
| 46 | L | P | R |
| 47 | F | P | R |
| 48 | S | P | R |
| 49 | M | P | R |
| 50 | T | Q | L |
| 51 | M | Q | L |
| 52 | F | Q | L |
| 53 | I | Q | L |
| 54 | V | Q | L |
| 55 | V | Q | R |
| 56 | W | Q | R |
| 57 | A | Q | R |
| 58 | S | Q | R |
| 59 | Y | Q | R |
| 60 | I | R | Q |
| 61 | G | R | Q |
| 62 | W | R | Q |
| 63 | P | R | Q |
| 64 | A | R | Q |
| 65 | P | R | R |
| 66 | A | R | R |
| 67 | M | R | R |
| 68 | V | R | R |
| 69 | T | R | R |
| 70 | A | S | L |
| 71 | I | S | L |
| 72 | Y | S | L |
| 73 | P | S | L |
| 74 | S | S | L |
| 75 | T | S | R |
| 76 | M | S | R |
| 77 | V | S | R |
| 78 | A | S | R |
| 79 | P | S | R |

SEQ ID NO: 80 Primer 1 (R103):
5'- GAG TCA TTC TCG ACT TGC GGC CGC TGA GGA GAC GGT GAC CTG GGT CCC CTG GCC (A/T/C/G)CG -3'

SEQ ID NO: 81 Primer 2 (R103):
5'-GAG TCA TTC TCG ACT TGC GGC CGC TGA GGA GAC GGT GAC CTG GGT CCC CTG GCC (C/T)CT-3'

SEQ ID NO: 82 Primer 3 (K103):
5'- GAG TCA TTC TCG ACT TGC GGC CGC GCT GGA GAC GGT GAC CTG GGT CCC CTG GCC (T/C)TT -3'

Figure 6-3

SEQ ID NO: 83 Primer 4 (Q103):
5'- GAG TCA TTC TCG ACT TGC GGC CGC TGA GGA GAC GGT GAC CTG GGT CCC CTG GC(C/G) (C/T)TG -3'

SEQ ID NO: 84 Primer 5 (L103):
5'- GAG TCA TTC TCG ACT TGC GGC CGC TGA GGA GAC GGT GAC CTG GGT CCC CTG GCC (A/G/C/T)AG -3'

SEQ ID NO: 85 Primer 6 (F103):
5'- GAG TCA TTC TCG ACT TGC GGC CGC TGA GGA GAC GGT GAC CTG GGT CCC CTG GCC (A/G)AA -3'

SEQ ID NO: 86 Primer 7 (G103):
5'- GAG TCA TTC TCG ACT TGC GGC CGC TGA GGA GAC GGT GAC CTG GGT CCC CCC CGG (A/G/C/T)CC -3'

SEQ ID NO: 87 Primer 8 (S103):
5'- GAG TCA TTC TCG ACT TGC GGC CGC TGA GGA GAC GGT GAC CTG GGT CCC CTG (A/G/C/T)GA (A/G/C/T)GA -3'

SEQ ID NO: 88 Primer 9 (P103):
5'- GAG TCA TTC TCG ACT TGC GGC CGC TGA GGA GAC GGT GAC CTG GGT CCC CTG CTG (A/G/C/T)GG -3'

FUNCTIONAL HEAVY CHAIN ANTIBODIES, FRAGMENTS THEREOF, LIBRARY THEREOF AND METHODS OF PRODUCTION THEREOF

RELATED APPLICATIONS

This application is a continuation of U.S. application Ser. No. 11/474,521, filed Jun. 23, 2006, which is a continuation of U.S. application Ser. No. 10/492,668, filed Oct. 5, 2004, which is national stage filing under 35 U.S.C. §371 of international application PCT/EP02/07804, filed Jul. 12, 2002, which was published under PCT Article 21(2) in English, and which claims the benefit under 35 U.S.C. §119(e) of U.S. provisional application Ser. No. 60/355,054, filed Oct. 24, 2001, all of which are incorporated by reference herein.

FIELD OF THE INVENTION

The present invention relates to functional heavy chain antibodies, fragments thereof and a library thereof. It also relates to methods for producing functional heavy chain antibodies, fragments thereof and a library thereof. It further relates to uses of functional heavy chain antibodies, fragments thereof and a library thereof.

BACKGROUND OF THE INVENTION

The IgG isotype is the most abundant immunoglobulin found in sera. In all mammals, it is composed of two identical heavy (H) chains and two identical light (L) chains. Immunoglobulins harbouring this structure are therefore designated four-chain immunoglobulins. The H-chain of a 4-chain immunoglobulin contains 4 domains and a hinge region in between the second and third domain. The L-chain has two domains. The N-terminal domains of both the L- and H-chain are more variable in sequence than the remaining domains and are known as V-domains (VL and VH respectively). Three loops within the VH and three loops within the VL juxtapose in the paired VH-VL domains and constitute the antigen-binding site. The loops are hypervariable in sequence and named CDR for Complementarity Determining Region. A description of the general structure of a 4-chain Immunoglobulin is provided in "Immunology" Roitt I. et al., Ed. MEDSI/McGRAW-HILL.

Much of the antigen binding diversity and the success of antibodies to generate a tight antigen binder against virtually all possible foreign substances, comes from the random pairing of one out of thousands of possible VHs with one out of thousands possible VLs. The second domain of the L-chain, having a more conserved sequence and denoted CL, is associated with the second domain of the H-chain (CH1) that has also a conserved sequence.

A pathological disorder in humans, known as heavy chain disease, is characterised by the presence of antibodies in the serum that do not contain L-chains. Moreover, these antibodies lack important parts of their VH and CH1 as well, although the missing VH and CH1 regions can vary widely among different HCAb (Heavy Chain Antibody). The deletions in the H-chain are due to deletions of the rearranged H-chain involving part of the VH and the CH1 domain. These antibodies no longer recognise antigen since the VL is absent and large parts of the VH is absent too. The HCAb can be secreted from the B-cells because the chaperone proteins (such as BIP) that associate with the CH1 retain the H chain in the endoplasmic reticulum until BIP is replaced by the L-chain. In absence of the CH1 polypeptide domain, the BIP can no longer retain the truncated H-chain in the endoplasmic reticulum, and the L-chain cannot bind either resulting in the fact that the H-chains are immediately secreted as homodimers.

Similar non-functional HCAbs were also reported to emerge in mouse monoclonal cell lines.

In sera of Camelidae (camels, dromedaries and llamas) we found the presence of the 4-chain immunoglobins and, in addition, of large amounts of functional HCAbs. These functional HCAbs have been described in European Patent Application No. 0656946 and in various publications including Hamers-Casterman et al. (1993), Vu et al. (1997) and Muyldermans et al. (2001). They are distinct from the human/mouse HCAbs present as a result of the pathological stage, in several respects. Firstly, they are functional in antigen binding. In this respect the HCAbs found in Camelidae are functional normal immunoglobulins. Secondly, in Camelidae, the entire CH1 domain is missing, and the V domain is intact but HCAbs have a sequence that deviates at a few sites from normal VH sequences. Said functional HCAb occur as a homodimeric molecules.

The CH1 is however encoded in the germline of all γ-genes in dromedaries (and llama) and is removed from the mRNA coding for the functional HCAbs by a splicing of the 3' end of the V-exon with the 5' end of the hinge exon. Thus, the CH1 is part of the intron and is no longer recognized as an exon because of a single point mutation of the consensus splicing signal sequence. Llama and dromedary carry the same point mutation at the former CH1 exon and this finding indicates that these γ-genes emerged before the llama and camels diverged from each other. The different splicing activity of the mRNA is not an alternative splicing as all mRNA is spliced according to this scheme. Hence these γ-genes will always lead to a H-chain with its CH1 removed. Other γ-genes are used to produce the common H-chain with a CH1 domain.

The V-domain of the H-chain of functional HCAb (referred to as VHH, for Variable domain of the H-chain of a normal, i.e. immunologically-active HCAb) is expected to acquire adaptations versus the VH (i.e. V-domain of H-chain of conventional four-chain antibody) in the regions that are no longer contacting the VL (or the CH1) domain and in those participating in antigen binding (i.e. the paratope).

For instance, Chothia et al. (1985) have indicated in the above-referenced publication that crystallographic data revealed that conserved Val 37, Gly 44, Leu 45 and Trp 47 are clustered in space in a conventional 4-chain IgG and make important hydrophobic contacts with the VL. They added that the VH amino acids Gln 39, Tyr 91, Trp 103 and Glu 105 are also recognized as important for VL association. Desmyter et al. (1996) further observed that the surface of the VHH domain which is present in camelidae and which corresponds to the VH side of conventional IgG which interacts with a VL is significantly reshaped in the camelid VHHs. In the present invention, the numbering of the amino acid residues is given by reference to the Kabat numbering (Kabat E, 1991) which is used in accordance with the Kabat database available, for example at the website of Dr. A.C.R. Martin's Bioinformatics Group at University College London bioinf.org.uk/abs.

The most frequently occurring amino acid residues at twelve VH locations known to interact with VL have been determined for 332 vertebrate VH segments. It is mentioned that for the purpose of the present invention, the protein domain of the variable heavy polypeptide chain is referred as "VH" and the corresponding DNA is designated VH-D-J as it is assembled from a VH germline, a diversity D minigene and a J minigene. In fact the CDR3 and FR4 are not encoded by the VH, but they are provided by D and J minigene that are recombined with the VH or (VHH) germline.

For comparison, the amino acid consensus has been deduced for 42 dromedary germline VHH sequences at the corresponding locations. The preferred amino acid residues at four positions (39, 43, 60 and 91, Kabat numbering) is invariable in VH and VHH. In contrast, at four other sites (33, 35, 50 and 58) neither VH nor VHH sequences reveal a pronounced amino acid preference. At the latter VH sites, the possible contact with the VL is dependent on the actual angle between VH and VL domains, and this explains the observed amino acid degeneracy. The only crucial differences between VH and VHH proteins in this area concern position 37, 44, 45 and 47. These are highly conserved amino acid residues among VH phenotypes (i.e. Val37, Gly44, Leu45 and Trp47), but in the VHH, the inventors observed most frequently Phe37 (or Tyr), Glu44, Arg45 (or Cys), and Gly47 (or Leu). These comparisons substantiate previous identifications of camel VHH-specific "hallmark" residues that arise in response to the absence of the L-chain.

From the results published by Nguyen et al. (2000), it is apparent that VHH and VH genes are imprinted in the dromedary genome. The VH and VHH genes are most likely residing in the same locus. It was noticed that the VH and VHH germline genes use the same D and J genes with the H-chain of conventional 4-chain antibodies. By PCR, around 50 VH and around 40 VHH germline genes were identified in dromedary. Each PCR fragment contains a leader signal exon and a V-exon, that ends where the CDR3 should start. The CDR3 and FR4 are provided by the recombined D-J segments. The VH germline segment harbours codons for Val37, Gly44, Leu45 and Trp47, and the VHH germline minigenes possess the Phe37 (11×) Tyr37 (30×) or in one single case Val37; Glu44 or Gln44 (8×); Arg45 (37×) or Cys45 (5×) and Gly47 (6×) or Leu47 (24×) or Trp47 (8×) or Phe47 (3×). In addition, these VHH germline-genes contain always (except 1) a Cys codon at position 45 or at the CDR1 region (codon 30, 32 or 33). Based on the length of the CDR2 (16 or 17 amino acids in size) and the location of the extra Cys, the VHH germline segments were grouped in subfamilies. Some subfamilies had several members while others are much scarcer in the genome. However, it should be noted that the frequency of occurrence of these VHH germline genes in expressed HCAb is not at all related to their frequency of occurrence in the genome. The Cys at position 45 or around the CDR1 is normally maintained in the rearranged VHH-D-J segments, and these rearrangements products have also acquired an extra Cys in the CDR3. Likewise, VHH-D-J rearrangements that were unable to generate an extra Cys in their CDR3 will apparently knock out the Cys45 or Cys in the CDR1 region probably by somatic hypermutation or by B-cell receptor editing. B cell receptor editing is a mechanism by which an upstream unrearranged V-segment is recombined into an existing V-D-J recombination product, that was most likely not functional, or recognizing a self antigen.

For dromedary, the VHH domains carry also longer CDR3 than that of the VH domains (average length 17-18 versus 9). Three possibilities can be envisaged to generate a longer CDR3. The VHH may uses two or more D minigenes, however, this is unlikely in view of the necessity to recombine two minigenes with a different recombination signal sequence (the 12-23 spacer rule). Alternatively, a more active terminal deoxynucleotidyl transferase during the D-J or V-D-J recombination might add several non-template encoded nucleotides. Finally, it can not be excluded that the length difference is only due to selection in which the fraction of VHH domains with long CDR3 or the VH domains with short CDR3 is much more likely to become functional to interact with antigen. A combination of the two latter explanations might also be relevant.

It has been proposed repeatedly that the presence of the VHH hallmarks at positions 37, 44, 45 or 47 or the substitution of the VH into the VHH hallmarks can lead to the formation of soluble single-domain antibody fragment. Of these, the amino acid at position 45 was considered crucial as the substitution of Leu45 of a human VH domain by Arg45 rendered the isolated domain more soluble. This camelised human VH adopts a properly folded immunoglobulin structure (Riechman, 1996. Rearrangement of the former VL interface in the solution structure of a camelised, single domain VH antibody).

However, work of Chothia et al. (1985) revealed that amino acids of VH at position 35, 37, 39, 44, 45, 47, 91, 93 encoded by the VH gene segment, 95, 100, 101 as part of the CDR3, and 103, 105 encoded by the J gene segment are the key participants for the VL interaction. Of these, amino acids 37, 45, 47 differ largely between VH and VHH. Position 103 is occupied by a conserved Trp that is well buried in the VH-VL complex and provides the largest contact surface area with the VL after Leu45 and Trp47 (FIG. 2 in Chothia et al.). As this Trp103 is encoded by the J gene and as the J gene is used in common in the VH-D-J and VHH-D-J recombination, it is logical to expect Trp at position 103 in VHH's as well. Since the VH-VL association is mediated by hydrophobic interactions, it is also clear that the substitution of the large aromatic and hydrophobic Trp 103 residue by the charged and hydrophilic Arg will prevent the association with a VL, and that of the surrogate light chain as well. WO92/01787 claims a single chain variable domain, being a synthetic variable immunoglobulin heavy chain domain, in which one or more of the amino acid residues at position 37, 39, 45, 47, 91, 93 or 103 is altered, whereby the tryptophan at position 103 is changed into glutamate, tyrosine or threonine. However, there is no indication that a substitution of tryptophan at 103 alone by arginine, glycine, lysine, proline or serine would be sufficient to obtain a functional heavy chain antibody, neither that this mutation could compensate for the absence of a charged amino acid or a cysteine at position 45, nor that said mutation may result in an increased solubility of a single domain heavy chain antibody fragment.

It is known in the art that the production of antibodies, for example by bacterial overexpression techniques, by phage display libraries, is technically difficult due to the antibody or fragments thereof being poorly expressed, insoluble, misfolded. It is also known that the screening of antibody libraries is restricted to those which are soluble, so excluding a large fraction of antibodies with potentially active antigen binding regions. Thus binders which might be therapeutically useful would be precluded from screening. There is a need by researchers involved in discovering new therapeutic agents for a method for producing functional antibodies and fragments thereof. There is a need by researchers involved in discovering new therapeutic agents for antibody libraries comprising functional antibodies. There is a need by researchers involved in discovering new therapeutic agents for methods to functionalise antibodies.

SUMMARY OF THE INVENTION

One embodiment of the invention is a functional heavy chain antibody, a functional single domain heavy chain antibody, a functional VH domain, or a functional fragment thereof comprising, an amino acid which is neither a charged amino acid nor a C at position 45, and comprising an amino acid at position 103 independently chosen from the group consisting of R, G, K, S, Q, L, and P, and optionally an amino acid at position 108 independently chosen from the group consisting of Q, L and R, said positions determined according to the Kabat numbering.

Another embodiment of the invention is a functional heavy chain antibody, a functional single domain heavy chain antibody, a functional VH domain, or a functional fragment thereof comprising an amino acid which is neither a charged amino acid nor a C at position 45 and SEQ ID NO: 13 (RGQGTQ) according to FIG. 6, said positions determined according to the Kabat numbering.

Another embodiment of the invention is a functional heavy chain antibody, a functional single domain heavy chain antibody, a functional VH domain, or a functional fragment thereof comprising an amino acid which is neither a charged amino acid nor a C at position 45 and SEQ ID NO: 14 (RGKGTQ) according to FIG. 6, said positions determined according to the Kabat numbering.

Another embodiment of the invention is a functional heavy chain antibody, a functional single domain heavy chain antibody, a functional VH domain, or a functional fragment thereof comprising SEQ ID NO: 15 (VXXXXXXGLXW) according to FIG. 6, wherein X is any amino acid, said positions determined according to the Kabat numbering.

Another embodiment of the invention is a functional heavy chain antibody, a functional single domain heavy chain antibody, a functional VH domain, or a functional fragment thereof comprising an amino acid which is neither a charged amino acid nor a C at position 45 and SEQ ID NO: 16 (LGQGTQVTVSS) according to FIG. 6, said positions determined according to the Kabat numbering.

Another embodiment of the invention is a functional heavy chain antibody, a functional single domain heavy chain antibody, a functional VH domain, or a functional fragment thereof comprising an amino acid which is neither a charged amino acid nor a C at position 45 and SEQ ID NO: 17 (QGQGTGVTVSS) according to FIG. 6, said positions determined according to the Kabat numbering.

Another embodiment of the invention is a functional heavy chain antibody, a functional single domain heavy chain antibody, a functional VH domain, or a functional fragment thereof comprising an amino acid which is neither a charged amino acid nor a C at position 45 and SEQ ID NO: 18 (PGQGTQVTVSS) according to FIG. 6, said positions determined according to the Kabat numbering.

Another embodiment of the invention is a functional heavy chain antibody, a functional single domain heavy chain antibody, a functional VH domain, or a functional fragment thereof comprising an amino acid which is neither a charged amino acid nor a C at position 45 and SEQ ID NO: 19 (SSQGTQVTVSS) according to FIG. 6, said positions determined according to the Kabat numbering.

Another embodiment of the invention is a functional heavy chain antibody, a functional single domain heavy chain antibody, a functional VH domain, or a functional fragment thereof, comprising any one of SEQ ID NOS: 1 to 10 according to FIG. 6.

Another embodiment of the invention is a functional heavy chain antibody, a functional single domain heavy chain antibody, a functional VH domain, or a functional fragment thereof, comprising any one of SEQ ID NOS: 1, 3, 5, 7 or 9 according to FIG. 6.

Another embodiment of the invention is a functional heavy chain antibody, a functional single domain heavy chain antibody, a functional VH domain, or a functional fragment thereof, comprising any one of SEQ ID NOS: 2, 4, 6, 8 or 10 according to FIG. 6.

Another embodiment of the invention is a functional heavy chain antibody, a functional single domain heavy chain antibody, a functional VH domain, or a functional fragment thereof, comprising any one of SEQ ID NOS: 1, 2, 3, 4 or 5 according to FIG. 6.

Another embodiment of the invention is a functional heavy chain antibody, a functional single domain heavy chain antibody, a functional VH domain, or a functional fragment thereof, comprising any one of SEQ ID NOS: 6, 7, 8, 9 or 10 according to FIG. 6.

Another embodiment of the invention is a functional heavy chain antibody, a functional single domain heavy chain antibody, a functional VH domain, or a functional fragment thereof, comprising any one of SEQ ID NOS: 5, 6, 7, 8 or 9 according to FIG. 6.

Another embodiment of the invention is a functional heavy chain antibody, a functional single domain heavy chain antibody, a functional VH domain, or a functional fragment thereof, comprising any one of SEQ ID NOS: 1, 3, 7, 9 or 10 according to FIG. 6.

Another embodiment of the invention is a functional heavy chain antibody, a functional single domain heavy chain antibody, a functional VH domain, or a functional fragment thereof, comprising any one of SEQ ID NOS: 2, 5, 8, 9 or 10 according to FIG. 6.

Another embodiment of the invention is a functional heavy chain antibody, a functional single domain heavy chain antibody, a functional VH domain, or a functional fragment thereof, comprising any one of SEQ ID NOS: 3, 4, 5, 6 or 7 according to FIG. 6.

Another embodiment of the invention is a functional heavy chain antibody, a functional single domain heavy chain antibody, a functional VH domain, or a functional fragment thereof, comprising any one of SEQ ID NOS: 4, 6, 7, 8 or 9 according to FIG. 6.

Another embodiment of the invention is a functional heavy chain antibody, a functional single domain heavy chain antibody, a functional VH domain, or a functional fragment thereof, comprising any one of SEQ ID NOS: 20 to 79 according to FIG. 6.

Another embodiment of the invention is a functional heavy chain antibody, a functional single domain heavy chain antibody, a functional VH domain, or a functional fragment thereof, comprising SEQ ID NO: 1.

Another embodiment of the invention is a functional heavy chain antibody, a functional single domain heavy chain antibody, a functional VH domain, or a functional fragment thereof, comprising SEQ ID NO: 2.

Another embodiment of the invention is a functional heavy chain antibody, a functional single domain heavy chain antibody, a functional VH domain, or a functional fragment thereof, comprising SEQ ID NO: 3.

Another embodiment of the invention is a functional heavy chain antibody, a functional single domain heavy chain antibody, a functional VH domain, or a functional fragment thereof, comprising SEQ ID NO: 4.

Another embodiment of the invention is a functional heavy chain antibody, a functional single domain heavy chain antibody, a functional VH domain, or a functional fragment thereof, comprising SEQ ID NO: 5.

Another embodiment of the invention is a functional heavy chain antibody, a functional single domain heavy chain antibody, a functional VH domain, or a functional fragment thereof, comprising SEQ ID NO: 6.

Another embodiment of the invention is a functional heavy chain antibody, a functional single domain heavy chain antibody, a functional VH domain, or a functional fragment thereof, comprising SEQ ID NO: 7.

Another embodiment of the invention is a functional heavy chain antibody, a functional single domain heavy chain antibody, a functional VH domain, or a functional fragment thereof, comprising SEQ ID NO: 8.

Another embodiment of the invention is a functional heavy chain antibody, a functional single domain heavy chain antibody, a functional VH domain, or a functional fragment thereof, comprising SEQ ID NO: 9.

Another embodiment of the invention is a functional heavy chain antibody, a functional single domain heavy chain antibody, a functional VH domain, or a functional fragment thereof, comprising SEQ ID NO: 10.

Another embodiment of the invention is a functional heavy chain antibody, a functional single domain heavy chain antibody, a functional VH domain, or a functional fragment thereof, comprising SEQ ID NO: 20.

Another embodiment of the invention is a functional heavy chain antibody, a functional single domain heavy chain antibody, a functional VH domain, or a functional fragment thereof, comprising SEQ ID NO: 21.

Another embodiment of the invention is a functional heavy chain antibody, a functional single domain heavy chain antibody, a functional VH domain, or a functional fragment thereof, comprising SEQ ID NO: 22.

Another embodiment of the invention is a functional heavy chain antibody, a functional single domain heavy chain antibody, a functional VH domain, or a functional fragment thereof, comprising SEQ ID NO: 23.

Another embodiment of the invention is a functional heavy chain antibody, a functional single domain heavy chain antibody, a functional VH domain, or a functional fragment thereof, comprising SEQ ID NO: 24.

Another embodiment of the invention is a functional heavy chain antibody, a functional single domain heavy chain antibody, a functional VH domain, or a functional fragment thereof, comprising SEQ ID NO: 25.

Another embodiment of the invention is a functional heavy chain antibody, a functional single domain heavy chain antibody, a functional VH domain, or a functional fragment thereof, comprising SEQ ID NO: 26.

Another embodiment of the invention is a functional heavy chain antibody, a functional single domain heavy chain antibody, a functional VH domain, or a functional fragment thereof, comprising SEQ ID NO: 27.

Another embodiment of the invention is a functional heavy chain antibody, a functional single domain heavy chain antibody, a functional VH domain, or a functional fragment thereof, comprising SEQ ID NO: 28.

Another embodiment of the invention is a functional heavy chain antibody, a functional single domain heavy chain antibody, a functional VH domain, or a functional fragment thereof, comprising SEQ ID NO: 29.

Another embodiment of the invention is a functional heavy chain antibody, a functional single domain heavy chain antibody, a functional VH domain, or a functional fragment thereof, comprising SEQ ID NO: 30.

Another embodiment of the invention is a functional heavy chain antibody, a functional single domain heavy chain antibody, a functional VH domain, or a functional fragment thereof, comprising SEQ ID NO: 31.

Another embodiment of the invention is a functional heavy chain antibody, a functional single domain heavy chain antibody, a functional VH domain, or a functional fragment thereof, comprising SEQ ID NO: 32.

Another embodiment of the invention is a functional heavy chain antibody, a functional single domain heavy chain antibody, a functional VH domain, or a functional fragment thereof, comprising SEQ ID NO: 33.

Another embodiment of the invention is a functional heavy chain antibody, a functional single domain heavy chain antibody, a functional VH domain, or a functional fragment thereof, comprising SEQ ID NO: 34.

Another embodiment of the invention is a functional heavy chain antibody, a functional single domain heavy chain antibody, a functional VH domain, or a functional fragment thereof, comprising SEQ ID NO: 35.

Another embodiment of the invention is a functional heavy chain antibody, a functional single domain heavy chain antibody, a functional VH domain, or a functional fragment thereof, comprising SEQ ID NO: 36.

Another embodiment of the invention is a functional heavy chain antibody, a functional single domain heavy chain antibody, a functional VH domain, or a functional fragment thereof, comprising SEQ ID NO: 37.

Another embodiment of the invention is a functional heavy chain antibody, a functional single domain heavy chain antibody, a functional VH domain, or a functional fragment thereof, comprising SEQ ID NO: 38.

Another embodiment of the invention is a functional heavy chain antibody, a functional single domain heavy chain antibody, a functional VH domain, or a functional fragment thereof, comprising SEQ ID NO: 39.

Another embodiment of the invention is a functional heavy chain antibody, a functional single domain heavy chain antibody, a functional VH domain, or a functional fragment thereof, comprising SEQ ID NO: 40.

Another embodiment of the invention is a functional heavy chain antibody, a functional single domain heavy chain antibody, a functional VH domain, or a functional fragment thereof, comprising SEQ ID NO: 41.

Another embodiment of the invention is a functional heavy chain antibody, a functional single domain heavy chain antibody, a functional VH domain, or a functional fragment thereof, comprising SEQ ID NO: 42.

Another embodiment of the invention is a functional heavy chain antibody, a functional single domain heavy chain antibody, a functional VH domain, or a functional fragment thereof, comprising SEQ ID NO: 43.

Another embodiment of the invention is a functional heavy chain antibody, a functional single domain heavy chain antibody, a functional VH domain, or a functional fragment thereof, comprising SEQ ID NO: 44.

Another embodiment of the invention is a functional heavy chain antibody, a functional single domain heavy chain antibody, a functional VH domain, or a functional fragment thereof, comprising SEQ ID NO: 45.

Another embodiment of the invention is a functional heavy chain antibody, a functional single domain heavy chain antibody, a functional VH domain, or a functional fragment thereof, comprising SEQ ID NO: 46.

Another embodiment of the invention is a functional heavy chain antibody, a functional single domain heavy chain antibody, a functional VH domain, or a functional fragment thereof, comprising SEQ ID NO: 47.

Another embodiment of the invention is a functional heavy chain antibody, a functional single domain heavy chain antibody, a functional VH domain, or a functional fragment thereof, comprising SEQ ID NO: 48.

Another embodiment of the invention is a functional heavy chain antibody, a functional single domain heavy chain antibody, a functional VH domain, or a functional fragment thereof, comprising SEQ ID NO: 49.

Another embodiment of the invention is a functional heavy chain antibody, a functional single domain heavy chain antibody, a functional VH domain, or a functional fragment thereof, comprising SEQ ID NO: 50.

Another embodiment of the invention is a functional heavy chain antibody, a functional single domain heavy chain antibody, a functional VH domain, or a functional fragment thereof, comprising SEQ ID NO: 51.

Another embodiment of the invention is a functional heavy chain antibody, a functional single domain heavy chain antibody, a functional VH domain, or a functional fragment thereof, comprising SEQ ID NO: 52.

Another embodiment of the invention is a functional heavy chain antibody, a functional single domain heavy chain antibody, a functional VH domain, or a functional fragment thereof, comprising SEQ ID NO: 53.

Another embodiment of the invention is a functional heavy chain antibody, a functional single domain heavy chain antibody, a functional VH domain, or a functional fragment thereof, comprising SEQ ID NO: 54.

Another embodiment of the invention is a functional heavy chain antibody, a functional single domain heavy chain antibody, a functional VH domain, or a functional fragment thereof, comprising SEQ ID NO: 55.

Another embodiment of the invention is a functional heavy chain antibody, a functional single domain heavy chain antibody, a functional VH domain, or a functional fragment thereof, comprising SEQ ID NO: 56.

Another embodiment of the invention is a functional heavy chain antibody, a functional single domain heavy chain antibody, a functional VH domain, or a functional fragment thereof, comprising SEQ ID NO: 57.

Another embodiment of the invention is a functional heavy chain antibody, a functional single domain heavy chain antibody, a functional VH domain, or a functional fragment thereof, comprising SEQ ID NO: 58.

Another embodiment of the invention is a functional heavy chain antibody, a functional single domain heavy chain antibody, a functional VH domain, or a functional fragment thereof, comprising SEQ ID NO: 59.

Another embodiment of the invention is a functional heavy chain antibody, a functional single domain heavy chain antibody, a functional VH domain, or a functional fragment thereof, comprising SEQ ID NO: 60.

Another embodiment of the invention is a functional heavy chain antibody, a functional single domain heavy chain antibody, a functional VH domain, or a functional fragment thereof, comprising SEQ ID NO: 61.

Another embodiment of the invention is a functional heavy chain antibody, a functional single domain heavy chain antibody, a functional VH domain, or a functional fragment thereof, comprising SEQ ID NO: 62.

Another embodiment of the invention is a functional heavy chain antibody, a functional single domain heavy chain antibody, a functional VH domain, or a functional fragment thereof, comprising SEQ ID NO: 63.

Another embodiment of the invention is a functional heavy chain antibody, a functional single domain heavy chain antibody, a functional VH domain, or a functional fragment thereof, comprising SEQ ID NO: 64.

Another embodiment of the invention is a functional heavy chain antibody, a functional single domain heavy chain antibody, a functional VH domain, or a functional fragment thereof, comprising SEQ ID NO: 65.

Another embodiment of the invention is a functional heavy chain antibody, a functional single domain heavy chain antibody, a functional VH domain, or a functional fragment thereof, comprising SEQ ID NO: 66.

Another embodiment of the invention is a functional heavy chain antibody, a functional single domain heavy chain antibody, a functional VH domain, or a functional fragment thereof, comprising SEQ ID NO: 67.

Another embodiment of the invention is a functional heavy chain antibody, a functional single domain heavy chain antibody, a functional VH domain, or a functional fragment thereof, comprising SEQ ID NO: 68.

Another embodiment of the invention is a functional heavy chain antibody, a functional single domain heavy chain antibody, a functional VH domain, or a functional fragment thereof, comprising SEQ ID NO: 69.

Another embodiment of the invention is a functional heavy chain antibody, a functional single domain heavy chain antibody, a functional VH domain, or a functional fragment thereof, comprising SEQ ID NO: 70.

Another embodiment of the invention is a functional heavy chain antibody, a functional single domain heavy chain antibody, a functional VH domain, or a functional fragment thereof, comprising SEQ ID NO: 71.

Another embodiment of the invention is a functional heavy chain antibody, a functional single domain heavy chain antibody, a functional VH domain, or a functional fragment thereof, comprising SEQ ID NO: 72.

Another embodiment of the invention is a functional heavy chain antibody, a functional single domain heavy chain antibody, a functional VH domain, or a functional fragment thereof, comprising SEQ ID NO: 73.

Another embodiment of the invention is a functional heavy chain antibody, a functional single domain heavy chain antibody, a functional VH domain, or a functional fragment thereof, comprising SEQ ID NO: 74.

Another embodiment of the invention is a functional heavy chain antibody, a functional single domain heavy chain antibody, a functional VH domain, or a functional fragment thereof, comprising SEQ ID NO: 75.

Another embodiment of the invention is a functional heavy chain antibody, a functional single domain heavy chain antibody, a functional VH domain, or a functional fragment thereof, comprising SEQ ID NO: 76.

Another embodiment of the invention is a functional heavy chain antibody, a functional single domain heavy chain antibody, a functional VH domain, or a functional fragment thereof, comprising SEQ ID NO: 77.

Another embodiment of the invention is a functional heavy chain antibody, a functional single domain heavy chain antibody, a functional VH domain, or a functional fragment thereof, comprising SEQ ID NO: 78.

Another embodiment of the invention is a functional heavy chain antibody, a functional single domain heavy chain antibody, a functional VH domain, or a functional fragment thereof, comprising SEQ ID NO: 79.

Another embodiment of the invention is a functional heavy chain antibody, a functional single domain heavy chain antibody, a functional VH domain, or a functional fragment thereof, according to any of the macromolecules above wherein said macromolecule is derived from camel.

Another embodiment of the invention is a functional heavy chain antibody, a functional single domain heavy chain antibody, a functional VH domain, or a functional fragment thereof, according to any of the macromolecules above wherein said macromolecule is derived from human.

Another embodiment of the invention is a functional heavy chain antibody, a functional single domain heavy chain antibody, a functional VH domain, or a functional fragment thereof, according to any of the macromolecules above wherein said macromolecule is derived from mouse.

Another embodiment of the invention is a functional heavy chain antibody, a functional single domain heavy chain antibody, a functional VH domain, or a functional fragment thereof, according to any of the macromolecules above wherein said macromolecule is derived from rabbit.

Another embodiment of the invention is a functional heavy chain antibody, a functional single domain heavy chain antibody, a functional VH domain, or a functional fragment thereof, according to any of the macromolecules above wherein said macromolecule is derived from goat.

Another embodiment of the invention is a functional heavy chain antibody, a functional single domain heavy chain antibody, a functional VH domain, or a functional fragment thereof, according to any of the macromolecules above wherein said macromolecule is derived from kangaroo.

Another embodiment of the invention is a functional heavy chain antibody, a functional single domain heavy chain antibody, a functional VH domain, or a functional fragment thereof, according to any of the macromolecules above wherein said macromolecule is derived from sheep.

Another embodiment of the invention is a functional heavy chain antibody, a functional single domain heavy chain antibody, a functional VH domain, or a functional fragment thereof, according to any of the macromolecules above wherein said macromolecule is derived from any vertebrate species other than camel, human and mouse.

Another embodiment of the invention is a functional heavy chain antibody, a functional single domain heavy chain antibody, a functional VH domain, or a functional fragment thereof according to any of the macromolecules above, as an artificial mutant.

Another embodiment of the invention is a functional heavy chain antibody, a functional single domain heavy chain antibody, a functional VH domain, or a functional fragment thereof, according to any of the macromolecules above, as a peptide homologue of said functional heavy chain antibody, functional single domain heavy chain antibody, functional VH domain, or functional fragment thereof.

By "homologue" as meant herein is an amino acid sequence which is at least 65%, 70%, 75%, 80%, 85%, 90%, 95%, 96%, 97%, 98%, 98.5%, 99%, 99.5% identical to the amino acid sequences of the present invention. By a polypeptide with an amino acid sequence having at least, for example, 95% "identity" to a reference amino acid sequence of the present invention, it is intended at the amino acid sequence of the polypeptide is identical to the reference sequence, except that it may have up to 5% of its amino acids deleted or substituted compared with the reference sequence, or, except that the sequence may have amino acid insertions up to 5% of the total number of amino acids in the reference sequence. As a practical matter, whether any particular peptide is at least 65%, 70%, 75%, 80%, 85%, 90%, 95%, 96%, 97%, 98%, 98.5%, 99%, 99.5% identical to the amino acid sequences of the present invention can be determined using known algorithms.

Another embodiment of the invention is a polypeptide comprising a functional single domain heavy chain antibody, a functional VH domain, or a functional fragment thereof, as described above.

Another embodiment of the invention is a functional heavy chain antibody, a functional single domain heavy chain antibody, a functional VH domain, or a functional fragment thereof, as described above wherein one or more amino acids are derivatized.

Another embodiment of the invention is a functional heavy chain antibody, a functional single domain heavy chain antibody, a functional VH domain, or a functional fragment thereof as defined above wherein said macromolecules are dimers.

Another embodiment of the invention is a functional heavy chain antibody, a functional single domain heavy chain antibody, a functional VH domain, or a functional fragment thereof as defined above wherein said macromolecules are trimers.

Another embodiment of the invention is a functional heavy chain antibody, a functional single domain heavy chain antibody, a functional VH domain, or a functional fragment thereof as defined above wherein said macromolecules are multimeric.

Another embodiment of the invention is a method to functionalize a heavy chain antibody, a single domain heavy chain antibody, a VH domain, or a fragment thereof by replacing the amino acid at position 103 with an amino acid independently chosen from the group consisting of R, G, K, S and P, and optionally replacing the amino acid at position 108 with an amino acid independently chosen from the group consisting of L, Q and R, said positions determined by the Kabat numbering.

Another embodiment of the invention is a method to functionalize a heavy chain antibody, a single domain heavy chain antibody, a VH domain, or a fragment thereof by replacing the amino acid at position 103 with R, said position determined according to the Kabat numbering.

Another embodiment of the invention is a method to humanize and functionalize a heavy chain antibody, a single domain heavy chain antibody, a VH domain, or a fragment thereof, said method comprising replacing the amino acid at position 45 with L, and optionally replacing the amino acid at position 37 with V and/or the amino acid at position 44 with G and/or the amino acid at position 47 with W, and replacing of amino acid at position 103 with R, said position determined according to the Kabat numbering.

Another embodiment of the invention is a method to humanize and functionalize a heavy chain antibody, a single domain heavy chain antibody, a VH domain, or a fragment thereof, said method comprising replacing the amino acid at position 45 with L, replacing the amino acid at position 103 with an amino acid independently chosen from the group consisting of R, G, K, S and P, and optionally replacing the amino acid at position 37 with V and/or the amino acid at position 44 with G and/or the amino acid at position 47 with W, and optionally replacing the amino acid at position 108 with an amino acid independently chosen from the group consisting of L, Q and R, said positions determined by the Kabat numbering.

Another embodiment of the invention is a method according to the above methods, wherein said heavy chain antibody, single domain heavy chain antibody, VH domain, or fragment thereof is derived from human or mouse.

Another embodiment of the invention is a method according to the above methods, wherein said heavy chain antibody, single domain heavy chain antibody, VH domain, or fragment thereof is derived from human.

Another embodiment of the invention is a method according to the above methods, wherein said heavy chain antibody, single domain heavy chain antibody, VH domain, or fragment thereof is derived from mouse.

Another embodiment of the invention is a method according to the above methods, wherein said heavy chain antibody, single domain heavy chain antibody, VH domain, or fragment thereof is derived from rabbit.

Another embodiment of the invention is a method according to the above methods, wherein said heavy chain antibody, single domain heavy chain antibody, VH domain, or fragment thereof is derived from goat.

Another embodiment of the invention is a method according to the above methods, wherein said heavy chain antibody, single domain heavy chain antibody, VH domain, or fragment thereof is derived from sheep.

Another embodiment of the invention is a method according to the above methods, wherein said heavy chain antibody, single domain heavy chain antibody, VH domain, or fragment thereof is derived from rat.

Another embodiment of the invention is a method according to the above methods, wherein said heavy chain antibody, single domain heavy chain antibody, VH domain, or fragment thereof is derived from any vertebrate species other than human and mouse.

Another embodiment of the invention is a method to humanize a functional camelid heavy chain antibody, a functional camelid single domain heavy chain, a functional camelid VHH domain or a functional fragment thereof, said method comprising replacing the amino acid at position 45 with L, and optionally replacing the amino acid at position 37 with V and/or the amino acid at position 44 with G and/or the amino acid at position 47 with W, said positions determined by the Kabat numbering.

Another embodiment of the invention is a method to camelize a functional heavy chain antibody, a functional single domain heavy chain, a functional VH domain or a functional fragment thereof, said method comprising replacing the amino acid at position 45 with an amino acid independently chosen from the group consisting of L, V and P, replacing the amino acid at position 103 with an amino acid independently chosen from the group consisting of R, G, K, S and P, and replacing the amino acid at position 37 with F, the amino acid at position 44 with G, the amino acid at position 47 with W, and amino acid at position 103 with R, and optionally replacing the amino acid at position 108 with an amino acid independently chosen from the group consisting of L, Q and R, said positions determined by the Kabat numbering.

Another embodiment of the invention is a functional heavy chain antibody, a functional single domain heavy chain antibody, a functional VH domain, or a functional fragment thereof, obtainable by the methods above.

Another embodiment of the invention is a functional heavy chain antibody, a functional single domain heavy chain antibody, a functional VH domain, or a functional fragment thereof, obtained by the methods above.

Another embodiment of the invention is a functional humanized camelid heavy chain antibody, a functional humanized camelid single domain heavy chain, a functional humanized VH domain or a functional fragment thereof, obtainable by the methods above.

Another embodiment of the invention is a functional humanized camelid heavy chain antibody, a functional humanized camelid single domain heavy chain, a functional humanized VH domain or a functional humanized fragment thereof, obtained by the method above.

Another embodiment of the invention is a functional heavy chain antibody, a functional single domain heavy chain antibody; a functional VH domain, or a functional fragment thereof, according to above 4 paragraphs, as an artificial mutant.

Another embodiment of the invention is a functional heavy chain antibody, a functional single domain heavy chain antibody, a functional VH domain, or a functional fragment thereof, according to above 5 paragraphs, as a peptide homologue of said functional heavy chain antibody, functional single domain heavy chain antibody, functional VH domain, or functional fragment thereof.

Another embodiment of the invention is a polypeptide comprising a functional heavy chain antibody, a functional single domain heavy chain antibody, a functional VH domain, or a functional fragment thereof according to according to above 6 paragraphs.

Another embodiment of the invention is a functional heavy chain antibody, a functional single domain heavy chain antibody, a functional VH domain, or a functional fragment thereof, according to the above 7 paragraphs which recite said macromolecules, or a polypeptide according the above paragraph wherein one or more amino acids is derivatized.

Another embodiment of the invention is a functional heavy chain antibody, a functional single domain heavy chain antibody, a functional VH domain, or a functional fragment thereof obtained by the methods as defined above wherein said macromolecules are dimers.

Another embodiment of the invention is a functional heavy chain antibody, a functional single domain heavy chain antibody, a functional VH domain, or a functional fragment thereof obtainable by the methods as defined above wherein said macromolecules are dimers.

Another embodiment of the invention is a functional heavy chain antibody, a functional single domain heavy chain antibody, a functional VH domain, or a functional fragment thereof obtained by the methods as defined above wherein said macromolecules are trimers.

Another embodiment of the invention is a functional heavy chain antibody, a functional single domain heavy chain antibody, a functional VH domain, or a functional fragment thereof obtainable by the methods as defined above wherein said macromolecules are trimers.

Another embodiment of the invention is a functional heavy chain antibody, a functional single domain heavy chain antibody, a functional VH domain, or a functional fragment thereof obtained by the methods as defined above wherein said macromolecules are multimeric.

Another embodiment of the invention is a functional heavy chain antibody, a functional single domain heavy chain antibody, a functional VH domain, or a functional fragment thereof obtainable by the methods as defined above wherein said macromolecules are multimeric.

Another embodiment of the invention is a library, comprising one or more functional heavy chain antibodies, functional single domain antibodies, functional VH domains, or functional fragments thereof as defined above.

Another embodiment of the invention is a method to make a library, comprising at least one functional heavy chain antibody, functional single domain heavy chain antibody, functional VH domain, or a functional fragment thereof, comprising the steps:
  introducing a restriction enzyme recognition site in the coding region of the framework 4 region of a VH chain, whereby the cutting site of said restriction enzyme recognition site is situated in the CDR3 region,
  cutting the nucleic acid molecule comprising said coding sequence with said restriction enzyme, ligating a double stranded primer to the VH encoding nucleic acid molecule, restoring the CDR3 and so introducing an R amino acid at position 103, said position determined by the Kabat numbering, and amplifying the ligated fragments.

Another embodiment of the invention is a method according to the above, whereby said restriction enzyme cut is situated within the last two codons of the CDR3 coding region.

Another embodiment of the invention is a method according to the above, whereby said restriction enzyme creates a GA 3' sticky end by cutting before the first nucleotide of the codon coding for amino acid position 101 and after the second nucleotide of codon coding for amino acid position 101 on the complementary strand, said positions determined according to the Kabat numbering.

Another embodiment of the invention is a method according to the above, whereby said restriction enzyme cut is situated within the last codon of the CDR3 coding region.

Another embodiment of the invention is a method according to the above, whereby said restriction enzyme is creating a CA-3' sticky end by cutting before the second nucleotide of codon coding for amino acid position 102 and after the third nucleotide of codon 102 on the complementary strand, said position determined according to the Kabat numbering.

Another embodiment of the invention is a method according to the above, whereby said restriction enzyme is chosen from the group consisting of BpmI, Eco57I, BsgI, Smu I, Fau I, Bse RI and Bfi I.

Another embodiment of the invention is a method to make a library comprising at least one functional heavy chain antibody, functional single domain heavy chain antibody, functional VH domain, or functional fragment thereof, comprising a step of amplification of nucleic acid strands encoding a repertoire of immune or non-immune VHH antibodies, using a framework 1 specific primer as forward primer, and a back primer which anneals to said nucleic acid strands such that its 3'-terminal three nucleotides are positioned over the codon of the nucleic acid strands which encode amino acid position 103, the reverse-complement of said 3'-terminal three nucleotides encoding R103, K103, Q103, F103, P103, G103 or S103, said position determined according to the Kabat numbering.

Another embodiment of the invention is a method to make a library comprising at least one functional heavy chain antibody, functional single domain heavy chain antibody, functional VH domain, or functional fragment thereof, comprising a step of amplification of nucleic acid encoding a repertoire of immune or non-immune VHH antibodies or fragments thereof, using a framework 1 specific primer, as forward primer, and using one or more of SEQ ID NOs: 80 to 88 according to FIG. 6 as back primers.

Another embodiment of the invention is a library, comprising at least one functional heavy chain antibody, functional single domain heavy chain antibody, functional VH domain, or functional fragment thereof, obtainable by the method according to any of claims as defined above.

Another embodiment of the invention is a library, comprising at least one functional heavy chain antibody, functional single domain heavy chain antibody, functional VH domain, or functional fragment thereof, obtained by the method as defined above.

Another embodiment of the invention is a library as defined above wherein the methods use a single domain heavy chain library from human or mouse.

Another embodiment of the invention is a library as defined above wherein the methods use a single domain heavy chain library from camel.

Another embodiment of the invention is a library as defined above wherein the methods use a single domain heavy chain library from sheep.

Another embodiment of the invention is a library as defined above wherein the methods use a single domain heavy chain library from human.

Another embodiment of the invention is a library as defined above wherein the methods use a single domain heavy chain library from mouse.

Another embodiment of the invention is a library as defined above wherein the methods use a single domain heavy chain library from rat.

Another embodiment of the invention is a library as defined above wherein the methods use a single domain heavy chain library from goat.

Another embodiment of the invention is a library as defined above wherein the methods use a single domain heavy chain library from any vertebrate species other than camel, human or mouse.

Another embodiment of the invention is a heavy chain antibody, a functional single domain heavy chain antibody, a functional VH domain, or a functional fragment thereof, obtained by the method as defined above for use in immunoassays.

Another embodiment of the invention is a recombinant DNA construct useful for the expression of a polypeptide in a cell containing the construct, the construct comprising control sequences which regulate transcription and translation of the said antibody in the cell and a coding sequence regulated by the control sequences, wherein the coding sequence comprises a DNA sequence of at least 21 bp in reading frame in that the DNA sequence encodes a functional heavy chain antibody, a functional single domain heavy chain antibody, a functional VH domain, or a functional fragment thereof as defined above or a polypeptide as defined above.

Another embodiment of the invention is a recombinant DNA construct useful for the expression of a polypeptide in a cell containing the construct, the construct comprising control sequences which regulate transcription and translation of the said antibody in the cell and a coding sequence regulated by the control sequences, wherein the coding sequence comprises a DNA sequence of at least 42 bp in reading frame in that the DNA sequence encodes a functional heavy chain antibody, a functional single domain heavy chain antibody, a functional VH domain, or a functional fragment thereof as defined above or a polypeptide as defined above.

Another embodiment of the invention is a recombinant DNA construct useful for the expression of a polypeptide in a cell containing the construct, the construct comprising control sequences which regulate transcription and translation of the said antibody in the cell and a coding sequence regulated by the control sequences, wherein the coding sequence comprises a DNA sequence of at least 63 bp in reading frame in that the DNA sequence encodes a functional heavy chain antibody, a functional single domain heavy chain antibody, a functional VH domain, or a functional fragment thereof as defined above or a polypeptide as defined above.

Another embodiment of the invention is a recombinant DNA construct useful for the expression of a polypeptide in a cell containing the construct, the construct comprising control sequences which regulate transcription and translation of the said antibody in the cell and a coding sequence regulated by the control sequences, wherein the coding sequence comprises a DNA sequence of at least 83 bp in reading frame in that the DNA sequence encodes a functional heavy chain antibody, a functional single domain heavy chain antibody, a functional VH domain, or a functional fragment thereof as defined above or a polypeptide as defined above.

Another embodiment of the invention is a recombinant DNA construct useful for the expression of a polypeptide in a cell containing the construct, the construct comprising control sequences which regulate transcription and translation of the said antibody in the cell and a coding sequence regulated by the control sequences, wherein the coding sequence comprises a DNA sequence of at least 150 bp in reading frame in that the DNA sequence encodes a functional heavy chain antibody, a functional single domain heavy chain antibody, a functional VH domain, or a functional fragment thereof as defined above or a polypeptide as defined above.

Another embodiment of the invention is a recombinant DNA construct useful for the expression of a polypeptide in a cell containing the construct, the construct comprising control sequences which regulate transcription and translation of the said antibody in the cell and a coding sequence regulated by the control sequences, wherein the coding sequence comprises a DNA sequence of at least 240 bp in reading frame in that the DNA sequence encodes a functional heavy chain antibody, a functional single domain heavy chain antibody, a functional VH domain, or a functional fragment thereof as defined above or a polypeptide as defined above.

Another embodiment of the invention is a recombinant DNA construct useful for the expression of a polypeptide in a cell containing the construct, the construct comprising control sequences which regulate transcription and translation of the said antibody in the cell and a coding sequence regulated by the control sequences, wherein the coding sequence comprises a DNA sequence of at least 300 bp in reading frame in that the DNA sequence encodes a functional heavy chain antibody, a functional single domain heavy chain antibody, a functional VH domain, or a functional fragment thereof as defined above or a polypeptide as defined above.

Another embodiment of the invention is a nucleic acid comprising a DNA sequence encoding a functional heavy chain antibody, a functional single domain heavy chain antibody, a functional VH domain, or a functional fragment thereof as defined above or a polypeptide as defined above.

Another embodiment of the invention is a nucleic acid having a nucleotide sequence which is at least 65% identical to the sequence as defined above.

Another embodiment of the invention is a vector comprising a nucleic acid sequence as defined above.

Another embodiment of the invention is a host cell comprising an integrated or episomal copy of a nucleic acid molecule as defined above, or a vector as defined above.

Another embodiment of the invention is the host cell as used above, wherein said host cell is a yeast, bacterial, insect, fungal, plant or mammalian cell.

Another embodiment of the invention is a method for producing a functional heavy chain antibody, a functional single domain heavy chain antibody, a functional VH domain, or a functional fragment thereof as defined above or a polypeptide as defined above, comprising:
(a) culturing host cells comprising a nucleic acid as defined above, under conditions allowing the expression of the polypeptide, and,
(b) recovering the produced polypeptide from the culture.

Another embodiment of the invention is a functional heavy chain antibody, a functional single domain heavy chain antibody, a functional VH domain, or a functional fragment thereof as defined above or a polypeptide as defined above, or nucleic acid as defined above for the preparation of a medicament.

Another embodiment of the invention is a functional heavy chain antibody, a functional single domain heavy chain antibody, a functional VH domain, or a functional fragment thereof as defined above or a polypeptide as defined above, or nucleic acid as defined above for the preparation of a medicament for the treatment of a disease related to asthma, rhinoconjunctivitis, allergic disorders, acute allograft rejection, Crohn's disease and ulcerative colitis.

Another embodiment of the invention is a pharmaceutical composition comprising a functional heavy chain antibody, a functional single domain heavy chain antibody, a functional VH domain, or a functional fragment thereof as defined above or a polypeptide as defined above, or nucleic acid as defined above, optionally in combination with a suitable excipient.

Another embodiment of the invention is the use of a functional heavy chain antibody, a functional single domain heavy chain antibody, a functional VH domain, or a functional fragment thereof as defined above or a polypeptide as defined above, or nucleic acid as defined above in the diagnosis of a disease related to asthma, rhinoconjunctivitis, allergic disorders, acute allograft rejection, Crohn's disease and ulcerative colitis.

Another embodiment of the invention is the use of a functional heavy chain antibody, a functional single domain heavy chain antibody, a functional VH domain, or a functional fragment thereof as defined above or a polypeptide as defined above for the purification of a protein.

Another embodiment of the invention is a kit for the diagnosis of a pathological condition or a susceptibility to a pathological condition in a subject comprising a nucleic acid as defined above, a functional heavy chain antibody, a functional single domain heavy chain antibody, a functional VH domain, or a functional fragment thereof as defined above or a polypeptide as defined above.

Another embodiment of the invention is a method for diagnosing a pathological condition or a susceptibility to a pathological condition in a subject comprising the steps of:
(a) determining the presence or absence of a mutation in the nucleic acid as defined above, including mutations in the genomic and regulatory sequences of said nucleic acid, in a biological sample, and
(b) diagnosing a pathological condition or a susceptibility to a pathological condition based on the presence or absence of said mutation.

Another embodiment of the invention is a method for diagnosing a pathological condition or a susceptibility to a pathological condition in a subject comprising the steps of:
(a) determining the presence or amount of the nucleic acid as defined above or expression of a functional heavy chain antibody, a functional single domain heavy chain antibody, a functional VH domain, or a functional fragment as defined above or a polypeptide as defined above in a biological sample, and,
(b) diagnosing a pathological condition or a susceptibility to a pathological condition based on the presence or amount of said nucleic acid or expression of said functional heavy chain antibody, functional single domain heavy chain antibody, functional VH domain, functional fragment thereof or polypeptide.

Another embodiment of the invention is a drug screening assay for screening test compounds which interact with a functional heavy chain antibody, a functional single domain heavy chain antibody, a functional VH domain, or a functional fragment thereof as defined above or a polypeptide as defined above, comprising:

(a) combining a functional heavy chain antibody, a functional single domain heavy chain antibody, a functional VH domain, or a functional fragment thereof as defined above or a polypeptide as defined above with a test compound, under conditions which allow for interaction of the test compound to said functional heavy chain antibody, functional single domain heavy chain antibody, functional VH domain, functional fragment thereof or polypeptide, to form a complex, and, (b) detecting the formation of a complex, in which the ability of the test compound to interact with the said functional heavy chain antibody, functional single domain heavy chain antibody, functional VH domain, or functional fragment thereof, is indicated by the presence of the test compound in the complex.

Another embodiment of the invention is the product or compound identifiable by the assay as defined above.

Another embodiment of the invention is nucleic acid comprising the sequence SEQ ID NO: 80 according to FIG. 6.

Another embodiment of the invention is nucleic acid comprising the sequence SEQ ID NO: 81 according to FIG. 6.

Another embodiment of the invention is nucleic acid comprising the sequence SEQ ID NO: 82 according to FIG. 6.

Another embodiment of the invention is nucleic acid comprising the sequence SEQ ID NO: 83 according to FIG. 6.

Another embodiment of the invention is nucleic acid comprising the sequence SEQ ID NO: 84 according to FIG. 6.

Another embodiment of the invention is nucleic acid comprising the sequence SEQ ID NO: 85 according to FIG. 6.

Another embodiment of the invention is nucleic acid comprising the sequence SEQ ID NO: 86 according to FIG. 6.

Another embodiment of the invention is nucleic acid comprising the sequence SEQ ID NO: 87 according to FIG. 6.

Another embodiment of the invention is nucleic acid comprising the sequence SEQ ID NO: 88 according to FIG. 6.

Another embodiment of the invention is a nucleic acid having a nucleotide sequence which is at least 65% identical to the sequence as defined above.

Another embodiment of the invention is the use of a nucleic acid as defined above in a method to produce one or more functional heavy chain antibodies, functional single domain heavy chain antibodies, functional VH domains, or functional fragments thereof.

The antibodies of the above embodiments are functional and as such exhibit improved properties, for example, expression levels, stability, affinity and solubility over antibodies in which the characterising features are absent. It is known in the art that the production of antibodies, for example by bacterial overexpression techniques, in phage display libraries, for screening libraries, is difficult due to the properties of the antibody or fragments thereof.

DETAILED DESCRIPTION OF THE INVENTION

Surprisingly, the inventors have found that a heavy chain, carrying a mutation at position 103, possibly combined with a mutation at position 108 behaves as a functional heavy chain antibody (HCAb), even if it does not carry the VHH hallmark amino acids at positions 37, 44, 45 and 47. In particular, the inventors have found that a mutation wherein the amino acid residue corresponding to position 103 (Kabat numbering) is mutated to an amino acid selected among arginine, glycine, proline, serine, leucine, glutamine or lysine can compensate for the loss of the critical hallmark amino acid at position 45, whereby the charged amino acid or the cysteine at position 45, may be changed in any other amino acid, but preferably into a leucine. Prior to an aspect of the present invention, heavy chains having said amino acids at positions at 45 and 103 were considered by the person skilled in the art as part of a classical 4-chain antibody complex (Harmsen et al. 2000) and not as a functional heavy chain antibody. Moreover, for some antibodies having residues which characterise one aspect of the present invention, the presence of a light chain has been described (Anker et al., 1990; Chukwuocha at al., 1999), clearly demonstrating that these antibodies were not functional heavy chain antibodies.

Surprisingly, the inventors were able to show that an amino acid at position 103 selected among arginine, glycine, proline, serine or lysine increases the solubility of the heavy chain, while it may disrupt the possibility to interact with a light chain. Therefore, such a heavy chain molecule behaves like a functional heavy chain antibody, even without the hallmark amino acid for the functional HCAb at position 45.

The invention relates to a functional HCAb, comprising an amino acid, which is neither a charged amino acid nor a cysteine at position 45, and comprising an amino acid chosen from the group consisting of arginine (R), glycine (G), lysine (K), serine (S) and proline (P) at position 103, possibly combined with glutamine (Q) at position 108 according to the Kabat numbering. In one embodiment of the invention, the amino acid at position 45 is a L. In another embodiment, the amino acid at position 103 is an R. In another embodiment, the amino acid at position 103 is an R and the amino acid at position 108 is a Q.

In one embodiment of the invention embodiment, the functional HCAb or fragment thereof according to the invention is an artificial mutant. An artificial mutant, as used here, means that the change is introduced intentionally and differs from the sequence found in the natural situation. Said artificial mutant may be derived from a variable domain (designated VH) of a heavy polypeptide chain of an immunoglobulin wherein the amino acid residue corresponding to position 103 (Kabat numbering) is mutated to an amino acid selected from the group consisting of R, G, K, S and P, possibly in combination with a mutation wherein the amino acid residue corresponding to position 108 (Kabat numbering) is mutated to Q. In another embodiment, said artificial mutant is derived from a variable domain (designated VH) of a heavy polypeptide chain of an immunoglobulin wherein the amino acid residue corresponding to position 103 (Kabat numbering) is mutated to arginine. In another embodiment, said artificial mutant is derived from a variable domain (designated VH) of a heavy polypeptide chain of an immunoglobulin wherein the amino acid residue corresponding to position 103 (Kabat numbering) is mutated to arginine and the amino acid residue corresponding to position 108 (Kabat numbering) is mutated to glutamine. Alternatively, said artificial mutant may be derived from a variable domain (designated VHH) of a heavy polypeptide chain of a heavy chain antibody wherein the hallmark amino acid residue at position 45 is mutated to a Leucine, possibly in combination with a mutation of one or more of the other hallmark amino acids at position 37, 44 and 47 to Val37, Gly44 and Trp47. One embodiment is an artificial mutant wherein all hallmark amino acids at position 37, 44, 45 and 47 are mutated to Val37, Gly44, Leu45 and Trp47.

An artificial mutant according to the invention comprises a polypeptide sequence derived from the VH domain and encompasses within this polypeptide sequence RGQGTQ (SEQ ID NO: 13) or alternatively sequence RGKGTQ (SEQ ID NO: 14).

Another artificial mutant according to the invention comprises a polypeptide sequence derived from the VHH domain and encompasses within this polypeptide sequence VXXXXXXGLXW (SEQ ID NO: 15), whereby X can be any amino acid.

Another artificial mutant according to the invention comprises a polypeptide sequence derived from the VH domain and encompasses within this polypeptide sequence RGQGTQ (SEQ ID NO: 13), wherein R of said sequence is at position 103 according to the Kabat numbering. Another artificial mutant according to the invention comprises a polypeptide sequence derived from the VH domain and encompasses within this polypeptide sequence RGKGTQ (SEQ ID NO: 14), wherein R of said sequence is at position 103 according to the Kabat numbering.

Another artificial mutant according to the invention comprises a polypeptide sequence derived from the VHH domain and encompasses within this polypeptide sequence VXXXXXXGLXW (SEQ ID NO: 15), wherein V of said sequence is at position 37 according to the Kabat numbering, whereby X can be any amino acid.

Another artificial mutant according to the invention comprises a polypeptide sequence derived from the VH domain and encompasses within this polypeptide sequence LGQGTQVTVSS (SEQ ID NO: 16), wherein L of said sequence is at position 103 according to the Kabat numbering.

Another artificial mutant according to the invention comprises a polypeptide sequence derived from the VH domain and encompasses within this polypeptide sequence QGQGTGVTVSS (SEQ ID NO: 17), wherein L of said sequence is at position 103 according to the Kabat numbering.

Another artificial mutant according to the invention comprises a polypeptide sequence derived from the VH domain and encompasses within this polypeptide sequence PGQGTQVTVSS (SEQ ID NO: 18), wherein L of said sequence is at position 103 according to the Kabat numbering.

Another artificial mutant according to the invention comprises a polypeptide sequence derived from the VH domain and encompasses within this polypeptide sequence SSQGTQVTVSS (SEQ ID NO: 19), wherein L of said sequence is at position 103 according to the Kabat numbering.

Said SEQ ID NOs: 13 to 19 are those cited in FIG. 6.

The artificial mutant according to the invention is derived from a VH domain, or a VHH domain, meaning that in accordance with the present invention it can be isolated from said domain by introducing said mutations, or it can be synthesized, including chemically synthesized or expressed especially by recombinant techniques, including in host cells, starting from the knowledge of the polypeptide sequence of said VH domains or VHH domains and the position of the mutations to be introduced. More generally, it can be prepared by any method made available for the preparation of polypeptide chains.

The polypeptide chain derived from the VH gene and having the features as defined here above may be obtained by methods involving site-directed mutagenesis or PCR (using primers carrying said mutation), starting from a conventional VH-D-J gene, especially one obtained from a library. A relevant method is that described by Hemsley et al. (1989). The present invention thus provides the possibility to generate soluble mutant single domain antibody fragments that originate from a VH-D-J gene. The method of Hemsley, however, requires that the sequence of the gene to be mutated is known, at least in the region where the mutation has to be introduced. As a position to be mutated, residue 103, is adjacent to a variable region, the method of Hemsley et al. (1989) is not suitable for the introduction of a mutation in VHs with unknown variable regions, and an adapted method has to be applied in this case.

Alternatively, the polypeptide chain derived from the VHH and having the features as defined here above may be obtained by methods involving site-directed mutagenesis or PCR (using primers carrying said the mutation), starting from a HCAb VHH, especially one obtained from a library. As these mutations are situated in a conserved framework region, the method of Hemsley et al. (1989) can be applied. In that case, the present invention provides the possibility to humanize single domain antibody fragments that originate from a VHH-D-J gene. Humanization may comprise the replacement of one or more of the VHH hallmark amino acids at position 37, 44, 45 and 47 into the conserved human residues Val37, Gly44, Leu 45 and Trp47. However, to introduce the compensating mutation at position 103, the sequence of the adjacent variable region should be known, as discussed above.

The invention relates further to a method to solubilize single domain heavy chain fragment derived from conventional 4-chain immunoglobulins. Indeed, the inventors have shown that the presence at position 103 of a hydrophilic amino acid residue, especially of a residue selected among arginine, glycine, proline, serine or lysine renders the resulting polypeptide derived from the VH more soluble with respect to the same polypeptide having a tryptophan residue at position 103. This effect may even be enhanced by replacing the amino acid at position 108 by a glutamine.

Another aspect of the invention is a method to "humanize" a camelid heavy chain antibody, said method comprising at least the replacement of the camelid hallmark amino acid at position 45, possibly combined with a replacement of one or more of the other hallmark amino acids at position 37, 44 and 47. Humanizing, as used here, means that one or more of the camelid hallmark amino acids in the HCAb are replaced by their human counterpart as found in the human consensus sequence, without that said heavy chain antibody is losing its typical character, i.e. the humanization does not significantly affect the antigen binding capacity of the resulting HCAb or fragment thereof.

Another aspect of the invention is a functional single domain heavy chain antibody fragment, obtainable by the method according to the invention. Still another aspect of the invention is a functional single domain heavy chain antibody fragment, obtained by the method according to the invention. Still another aspect of the invention is a functional humanized single domain heavy chain antibody fragment, obtainable by the method according to the invention. Still another aspect of the invention is a functional humanized single domain heavy chain antibody fragment, obtained by the method according to the invention.

Another aspect of the invention is a library, comprising one or more functional single domain heavy chain antibody fragments according to the invention. In one embodiment of the present invention, said library comprises at least 100, or at least 1000, or at least 10 000, or at least 100 000, or at least 1 000 000 functional single domain heavy chain antibody fragments. Such a library has the advantage that it is composed of soluble molecules, contrary to a possible library of classical VH molecules, which would be insoluble and non-functional (Nutall et al., 2000). Whereas for one single VH, the problem may be solved by denaturation, followed by refolding and resolubilization, this procedure is not possible in case of the creation of a complex library, especially not when said creation is followed by the selection of domains with varying antigen binding specificities. Indeed, generation of insoluble and therefore "sticky" scaffold protein during selection procedures can lead to false positives through non-specific binding to antigen by hydrophobic patches on the displayed domain. Several attempts have been made to overcome this aggregation problem (Pessi et al, 1993; Quiocho, 1993; Dimasi et al., 1997), but till now, the attempts of producing single domain VH libraries with acceptable solubility characteristics have not been successful. Therefore, the soluble single domain heavy chain antibody fragment according to the invention allow for the first time the efficient construction of a library comprising functional single chain antibody fragments.

As the functional single domain heavy chain antibodies according to the invention do normally not occur in nature, such a library cannot be made by direct amplification of the messenger RNA, but has to be made by the use of mutagenic primers. Although in principle, a VHH backbone may be used as starting material, this has several drawbacks, as not only the camelid hallmark amino acids have to be mutated, but the compensating mutation at position 103 has to be introduced. For this reason, it is preferable to construct the library starting from a human VH mRNA library. From such a library, potent antigen binders may be retrieved. Contrary to the VHH situation, starting from a VH backbone, only the mutation at position 103 has to be introduced.

The problem to make such library is that the 3'-end primer used to amplify the VH by RT-PCR needs to be mutagenic for the codon 103, and the primer should extend for at least 4-5 nucleotides towards its 3'-end to anneal perfectly to the template. However, since this region is part of the CDR3, such a primer will contain too much degeneracies so that no DNA amplification will be achieved. As a consequence, making a functional single domain heavy chain library, according to the invention is far from obvious.

Therefore another aspect of the invention is a method to make a library, comprising at least one functional single chain library, according to the invention, comprising introducing a restriction enzyme recognition site in the coding region of the framework 4 region of a VH or VHH chain, whereby the cutting site of said restriction enzyme recognition site is situated in the CDR3 region cutting the nucleic acid molecule comprising said coding sequence with said restriction enzyme ligating a double stranded primer to the remaining V encoding nucleic acid molecules, restoring the CDR3 and framework 4 codons and introducing the 103 mutation in the framework 4 amplifying the ligated fragments.

One embodiment comprises said method whereby the method is carried out on a pool of coding sequences, such as a pool of mRNA as well as on one isolated coding sequence. Another embodiment comprises said method whereby the method is carried out on one isolated coding sequence, and a synthetic library is generated by randomizing one or more codons of one or more of the CDR loops. Alternatively, a library may be generated by grafting camelid CDR loops on the mutated framework, comprising the 103R mutation.

In another embodiment, the restriction enzyme cut is situated within the last codon or within the last two codons of the CDR3 coding region. One embodiment comprises said method, whereby said enzyme is creating a blunt end at the CDR3—framework 4 junction. Another embodiment comprises said method, whereby said enzyme creates a CA 3' sticky end by cutting before the second nucleotide of codon 102 and after the second nucleotide of codon 102, according to the Kabat numbering. Indeed, in most VH and VHH's, there is a conserved tyrosine (Y) at position 102. This amino acid is most frequently encoded by TAC. Another embodiment comprises said method, whereby said enzyme creates a GA 3' sticky end by cutting before the first nucleotide of codon 101 and after the second nucleotide of codon 101, according to the Kabat numbering. Indeed, in most human VH, there is a conserved aspartic acid (D) at position 101, a charged amino acid that is important for the CDR3 loop structure. This amino acid is encoded by either GAC or GAT. By creating a GA 3' sticky end, the conserved codon may be restored by the ligation to the double stranded primer. In that case, the codon 102 may be either randomized or fixed, by ligation of the primer. One embodiment comprises said method above, whereby said restriction site is Bpm I. Another embodiment comprises said method, whereby said restriction site is Eco57 I. Another embodiment comprises said method, whereby said restriction site is Bsg I. An embodiment comprises said method, whereby said restriction site is Fau I. Another embodiment comprises said method, whereby said restriction site is Smu I. Another embodiment comprises said method, whereby said restriction site is Bse R1.

Another embodiment comprises said method, whereby the restriction site is BfiI, introduced in such a way that the enzyme cuts at the CDR3 junction in the upper strand, and between the first and the second nucleotide of CDR3, adjacent to the framework 4 in the lower strand. In the latter case, the CDR3 and framework 4 regions may be restored by ligation with a double stranded primer consisting of the framework 4 coding region for the upper strand, and the complementary strand thereof, with either a TG 3' overhang, or a TG-3' overhang and an extra codon such as GTG, or TAC before the Trp103 codon.

Still another aspect of the inventions is a library obtainable by the invention, comprising one or more functional single domain heavy chain antibody fragments. Still another aspect of the invention is a library, obtained by the invention, comprising one or more functional single domain heavy chain antibody fragments.

In one embodiment, said library comprises at least 100, in another embodiment at least 1000, in another embodiment at least 10 000, in another embodiment at least 100 000, in another embodiment at least 1 000 000 functional single domain heavy chain antibody fragments.

Surprisingly, we have found that a significant fraction of the camelid antibodies comprises functional heavy chain antibodies according to the invention, contrary to what is assumed by the person skilled in the art. This significant fraction represent a new class of functional heavy chain antibodies. It would not be obvious, therefore, to a skilled artisan that a functional heavy chain antibody and/or a functional soluble single domain heavy chain antibody fragment can be isolated directly from a mRNA preparation from camelids, and this material can be used as starting material for the preparation of a functional soluble single domain heavy chain antibody fragment library according to the invention. As a consequence, another aspect of the invention is a library obtained by specific amplification and cloning of the new class of functional heavy chain antibodies described in this invention, and which have more homology to human antibodies than the class of VHH with the hydrophilic residues in FR2. In order to obtain this new class of VHH from a repertoire of immune or non-immune antibodies, specific primers for amplification were designed, that anneal preferentially to genes encoding VHH with Arginine, Lysine, Glutamine, Phenylalanine, Proline, Glycine, Tryptophan or Serine as residue 103. To accomplish specific annealing the 3' site of the primer ends exactly at the first nucleotide of the codon coding for residue 103, which in the new class of VHH is different from the Tryptophan 103 containing VHH fragments.

The following primers were designed:

```
primer 1 (R103):
                                         (SEQ ID NO: 80)
5'-GAG TCA TTC TCG ACT TGC GGC CGC TGA GGA GAC GGT

GAC CTG GGT CCC CTG GCC (A/T/C/G)CG-3' primer 2 (R103):
                                         (SEQ ID NO: 81)
5'-GAG TCA TTC TCG ACT TGC GGC CGC TGA GGA GAC GGT

GAC CTG GGT CCC CTG GCC (C/T)CT-3' primer 3 (K103):
                                         (SEQ ID NO: 82)
5'-GAG TCA TTC TCG ACT TGC GGC CGC GCT GGA GAC GGT

GAC CTG GGT CCC CTG GCC (T/C)TT-3' primer 4 (Q103):
                                         (SEQ ID NO: 83)
5'-GAG TCA TTC TCG ACT TGC GGC CGC TGA GGA GAC GGT

GAC CTG GGT CCC CTG GC(C/G) (C/T)TG-3' primer 5 (L103):
                                         (SEQ ID NO: 84)
5'-GAG TCA TTC TCG ACT TGC GGC CGC TGA GGA GAC GGT

GAC CTG GGT CCC CTG GCC (A/G/C/T)AG-3' primer 6 (F103):
                                         (SEQ ID NO: 85)
5'-GAG TCA TTC TCG ACT TGC GGC CGC TGA GGA GAC GGT

GAC CTG GGT CCC CTG GCC (A/G)AA-3' primer 7 (G103):
                                         (SEQ ID NO: 86)
5'-GAG TCA TTC TCG ACT TGC GGC CGC TGA GGA GAC GGT

GAC CTG GGT CCC CCC CGG (A/G/C/T)CC-3' primer 8 (S103):
                                         (SEQ ID NO: 87)
5'-GAG TCA TTC TCG ACT TGC GGC CGC TGA GGA GAC GGT

GAC CTG GGT CCC CTG (A/G/C/T)GA (A/G/C/T)GA-3' primer 9 (P103):
                                         (SEQ ID NO: 88)
5'-GAG TCA TTC TCG ACT TGC GGC CGC TGA GGA GAC GGT

GAC CTG GGT CCC CTG CTG (A/G/C/T)GG-3' primer 10 (Y103):
                                         (SEQ ID NO: 89)
5'-GAG TCA TTC TCG ACT TGC GGC CGC TGA GGA GAC GGT

GAC CTG GGT CCC CTG GCC (A/G)TA-3'
```

Specific amplification was carried out using a Framework 1 specific primer, that is 5' linked to a SfiI site, as forward primer, and a pool of primers 1-10 as back primers for the amplification of functional soluble single domain heavy chain antibody fragments according to the invention. The resulting material was cut with SfiI and NotI or BstEII and the resulting fragment is cloned into pHen4.

Still another aspect of the invention is the use of a functional heavy chain antibody according to the invention or a functional soluble single domain heavy chain antibody fragment according to the invention for the preparation of a medicament. Still another aspect of the invention is a pharmaceutical composition, comprising a functional heavy chain antibody, according to the invention, or comprising a functional soluble single domain heavy chain antibody fragment, according to the invention, optionally in combination with a suitable excipient. Indeed, antibodies may be used in the treatment of several diseases, such as, as a non-limiting example, asthma and rhinoconjunctivitis (Botger et al, 2002), allergic disorders (Babu et al, 2001), acute allograft rejection (Sollinger et al, 2001), Crohn's disease (Hommes et al, 2002) and ulcerative colitis (Gordon et al, 2002). The functional soluble single domain heavy chain antibody fragment may have a significant advantage due to their small size and their solubility.

Another aspect of the invention is the use of a functional heavy chain antibody according to the invention or a functional soluble single domain heavy chain antibody fragment according to the invention in diagnosis. Diagnostic methods, using antibodies are known to the person skilled in the art and include, as a non-limiting example ELISA and RIA methods. The antibodies according to the invention do have several additional advantages in these assays, due to their stability and the fact that they can be fixed on a solid support without significant loss of activity. The latter characteristic makes them specially suitable for coating of surfaces, as may be desirable in several immunological detection techniques, including their use in microarrays.

Still another aspect of the invention is the use of a functional heavy chain antibody according to the invention or a functional soluble single domain heavy chain antibody fragment according to the invention in the purification of proteins and other molecules. Purification methods such as, as a non-limiting example, immunochromatography are known to the person skilled in the art. The antibodies according to the invention do have several additional advantages in such purification methods, due to their stability, that may guarantee a long lifetime of the purification carrier, and due to the fact that they can be fixed on a solid support without significant loss of activity.

DEFINITIONS

The following definitions are set forth to illustrate and define the meaning and scope of various terms used to describe the invention herein.

"Derivatized" as used herein in reference to a polypeptidic macromolecule means comprising derivatized amino acids. For example, homo-phenylalanine, citrulline, and noreleucine are considered derivatized amino acids for the purposes of the invention. Derivatized amino acids also include imino acid residues such as proline and hydroxyproline. In addition, any amino acid representing a component of the variant proteins of the present invention, replaced by the same amino acid but of the opposite chirality, is considered derivatized. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R or the S, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes.

In the preferred embodiment, the derivatized amino acids are in the (S) or L-configuration or the (S) or D-configuration. Derivatized amino acids may be used, for example, to prevent or retard in vivo degradations. Proteins including non-naturally occurring amino acids may be synthesized or in some cases, made recombinantly; see van Hest et al., FEBS Lett 428:(1-2) 68-70 May 221998 and Tang et al., Abstr. Pap Am. Chem. S218:U138-U138 Part 2 Aug. 22, 1999, both of which are expressly incorporated by reference herein.

Aromatic amino acids may be replaced with D- or L-naphylalanine, DM or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl) alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1-C20.

Acidic amino acids can be regarded as derivatized when they are substituted with non-carboxylate amino acids while maintaining a negative charge, and derivatives or analogs thereof, such as the non-limiting examples of (phosphono) alanine, glycine, leucine, isoleucine, threonine, or serine; or sulfated (e.g., —SO3H) threonine, serine, or tyrosine.

Other substitutions may include unnatural hyroxylated amino acids. Other derivatives may made by combining "alkyl" with any natural amino acid. The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is defined as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the variant polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant polypeptides of to the present invention may include the following: Cysteinyl residues may be reacted with α-haloacetates (and corresponding amine), such as 2-chloroacetic acid or chloroacetamide, to give carboxymethyl or carboxyamidomethyl derivatives.

Cysteinyl residues may also be derivatized by reaction with compounds such as bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, P-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5 to 7.0 because this agent is relatively specific for the histidyl side chain, and para-bromophenacyl bromide may also be used, e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues.

Other suitable reagents for derivatizing α-amino-containing residues include compounds such as imidoesters e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues per se is well-known, such as for introducing spectral labels into tyrosyl residues by reaction with aromatic diazonium compounds or tetranitromethane.

N-acetyll midizol and tetranitromethane may be used to form O-acetyl tyrosyl species and 3-nitro derivatives, respectively. Carboxyl side groups (aspartyl or glutamyl) may be selectively modified by reaction with carbodiimides (R'—N—C—N—R') such as 1-cyclohexyl-3-(2-morpholiny-1-(4-ethyl)carbodiimide or 1-ethyl-3-(4-azonia-4,4-dimethylpentyl)carbodiimide. Furthermore aspartyl and glutamyl residues may be converted to asparaginyl and glutaminyl residues by reaction with ammonium ions. Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

"Functional" in reference to a heavy chain antibody, a single domain heavy chain antibody, a VH domain or fragments thereof means that the same retains a significant binding (dissociation constant in the micromolar range) to its epitope, compared with its binding in vivo, and that it shows no or limited aggregation (soluble and non-aggregated above 1 mg/ml), so allowing the use of the antibody as a binder.

"Functionalized" in reference to a heavy chain antibody, a single domain heavy chain antibody, or fragments thereof means to render said heavy chain antibody, a single domain heavy chain antibody, or fragments thereof functional.

By "fragments thereof" as used herein, is meant a portion corresponding to more than 95% of the sequence, more than 90% of the sequence of, more than 85% of the sequence of, more than 80% of the sequence of, more than 75% of the sequence of, more than 70% of the sequence of, more than 65% of the sequence of, more than 60% of the sequence of, more than 55% of the sequence of, or more than 50% of the sequence of.

"Coding sequence" is a nucleotide sequence, which is transcribed into mRNA and/or translated into a polypeptide when placed under the control of appropriate regulatory sequences. The boundaries of the complete coding sequence are determined by a translation start codon at the 5'-terminus and a translation stop codon at the 3'-terminus. However, coding sequence as used here is not limited to the complete coding sequence, but includes fragments thereof; such fragments are also indicated as coding region. A coding sequence can include, but is not limited to mRNA, cDNA, recombinant nucleotide sequences or genomic DNA, while introns may be present as well under certain circumstances.

"Human hallmark amino acids" as used herein in reference to the humanization of non-human antibodies are Val37, Gly44, Leu45, Trp47, positions determined according to the Kabat numbering.

"Nucleotide sequence" "DNA sequence" "nucleic acid molecule(s)" or "nucleic acid" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog.

"Upper strand" of a DNA sequence is the strand that comprise the DNA version of the codons as they occur in the mRNA, lower strand is the strand with the anticodons, that is used as template to synthesize the mRNA.

"VH domain" as used herein means the variable domain of H-chain of a conventional four-chain antibody.

"VHH domain" as used herein means variable domain of the H-chain of a conventional, (i.e. immunologically functional) HCAb.

BRIEF DESCRIPTION OF THE FIGURES

FIGS. 1-1 and 1-2: Nucleotide and translated amino acid sequences of wild type anti-b-lactamase VHH TEM04 (A; SEQ ID NO:11 and SEQ ID NO:12) and anti-carcinoembryonic antigen VHH CEA71 (B; SEQ ID NO:92 and SEQ ID NO:93).

FIG. 2: Western blot analysis of R103W mutant and wild type VHH from (A) anti-β-lactamase VHH TEM04 and (B) anti-carcinoembryonic antigen VHH CEA71. From each clone three cultures were induced and used for analysis. As positive control the anti-lysozyme VHH cAblys3 was used.

FIG. 6-1, 6-2, 6-3: SEQ ID NOS: 1 to 10 and 20 to 79: sequences of heavy chain antibody, single domain antibody, a VH domain, or a fragment thereof, wherein amino acids at positions indicated are substituted by amino acids indicated, said positions determined according to the Kabat numbering.

EXAMPLES

Example 1

Camelization of Isolated VH1

Figure 2A:
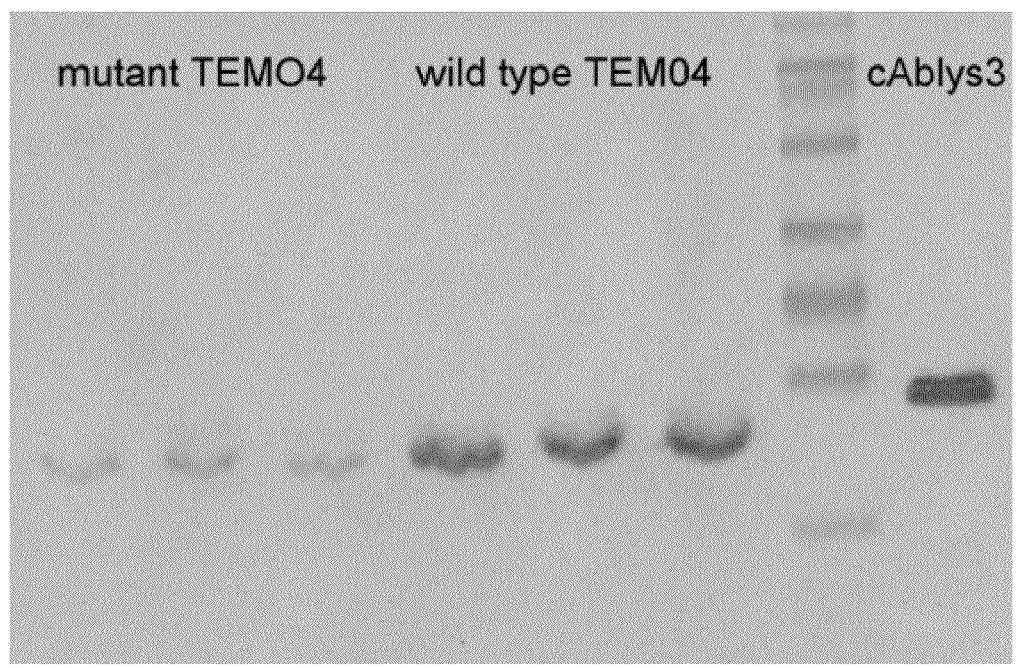

Classically, a recombinant VH domain is isolated from scFv libraries. Such VH domains usually originate from a cloning artifact for example by the cloning of VH instead of VH-VL, or they may originate from a gene recombination within the clone, due for example to instability of the linker sequences, resulting in the deletion of the VL gene fragment. These molecules are normally difficult to work with because of their low expression yields in, for example, bacterial and other expression systems and their low solubility. The inventors show that these VH molecules may be better expressed and show a higher solubility by introducing a mutation changing the Trp on position 103 into Arg. This is a much easier and more straightforward mutation than Val37Phe, Gly44Glu, Leu45Arg and Trp47Gly or part of it as originally carried out by Davies and Riechmann (1994). It has the additional advantage that it could be performed on all VH sequences, not only of human origin, but of all other species having antibodies with an Ig-fold.

Example 2

Generation of Soluble Single Domain from a scFv Antigen Binding Fragment

In cases where a minimal size of the antigen binding fragment is envisaged, it might be an advantage to design a single domain from an existing scFv. The VH domain has specific interest since this domain, in principle, provides specificity and is the largest contributor to affinity. Single domains have further advantages due to their smaller size. Although it has been repeatedly shown that VH domains retain sufficient activity to interact with antigen, VH domains are known to be sticky and insoluble. The present invention shows that these problems can be remedied by the Trp103Arg substitution.

Example 3

Effect of Arg103Trp Mutation on Solubility and Antigen Binding of VHH 3.1 Production and Purification of Wild Type and Mutant VHH The gene fragment encoding the anti-β-lactamase VHH TEM04 was mutagenized by PCR using the FR4 specific primer A4short-TEM04 (5'-GGA GAC GGT GAC CTG GGT CCC CTG GCC CCA TAC GAC-3') (SEQ ID NO: 96) thereby changing the wild type residue Arg on position 103 to Trp103. Using a similar approach, the anti-carcinoembryonic antigen (CEA) VHH CEA71, was mutated with primer A4short-CEAVH (5'-GGA GAC GGT GAC CTG GGT CCC CTG GCC CCA GGG GC-3') (SEQ ID NO: 97). The *E. coli* production vector pHEN6 was used for expression of the wild type and mutated VHH fragments. pHEN6 is derived from pHEN1 (Hoogenboom et al. (1991)), pHEN6 encoding the hexahistidine tag sequence for purification of VHH and lacking the phage M13 gene 3. The PCR-products and vector were digested with NcoI-BstEII and loaded on a 1% agarose gel. Fragments and vector were purified from gel with Jetsorb, ligated, transformed into WK6 competent cells and plated onto LB agar plates containing 100 μg/ml ampicillin and 2% glucose. Mutation of R to W on position 103 was confirmed by sequencing (FIG. 1).

For each construct pre-cultures were started in triplicate in 10 ml of LB-medium containing 100 μg/ml ampicillin and 2% glucose. 330 ml cultures (in TB-medium with 100 μg/ml ampicillin) were inoculated with 3 ml of preculture and grown at 37° C. Cultures were induced at OD600 nm=0.4 with 1 mM IPTG and grown overnight at 28° C. No significant differences were observed in cell densities after induction between the wild type and mutant (VHH TEM04: OD600 (wt)=1.05.+−.0.25; OD600(mut)=1.25.+−.0.05; VHH CEA71: OD600(wt)=1.48.+−.0.28; OD600(mut)=1.30.+−.0.20), suggesting that no toxic products were expressed.

Figure 2B:
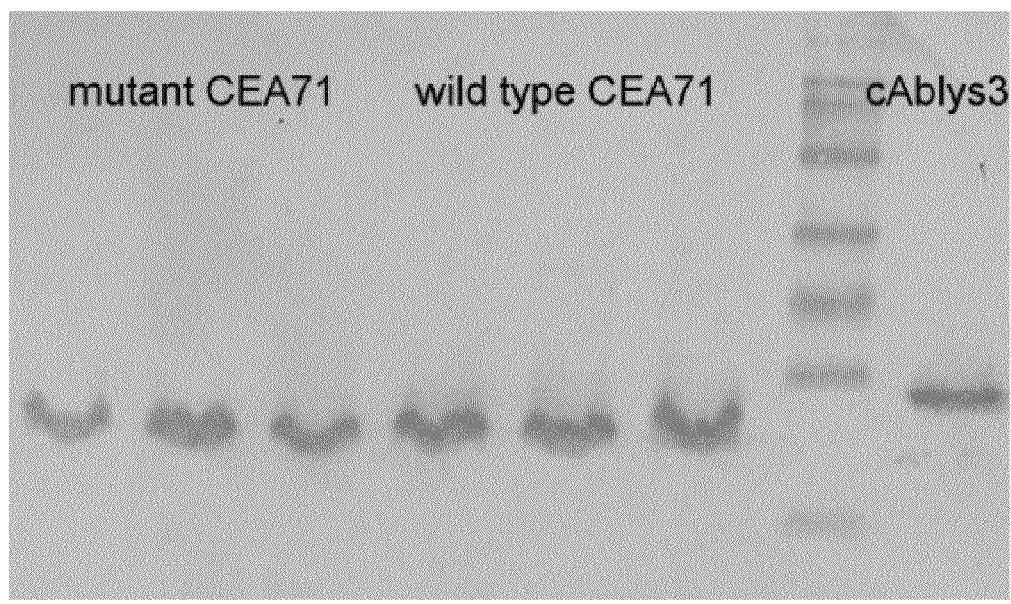

The cells were boiled in reducing sample buffer and loaded on 15% PAGE, normalized for the number of cells (OD600 nm=0.1). The proteins were blotted on nitrocellulose and blocked overnight in PBS containing 1% casein. The hexahistidine-tagged VHH was detected with mouse anti-Histidine monoclonal antibody (Serotec, diluted 1:1000 in PBS) and after 4 washes with PBS-0.5% tween-20 incubated with anti-mouse alkaline phosphatase conjugate (Sigma, diluted 1:1000) using NBT and BCIP as chromogenic substrates. It can be concluded that the VHH TEM04 mutant is expressed at much lower levels than its wild type derivative, while for VHH CEA71 no differences were observed (FIG. 2).

Figure 3:
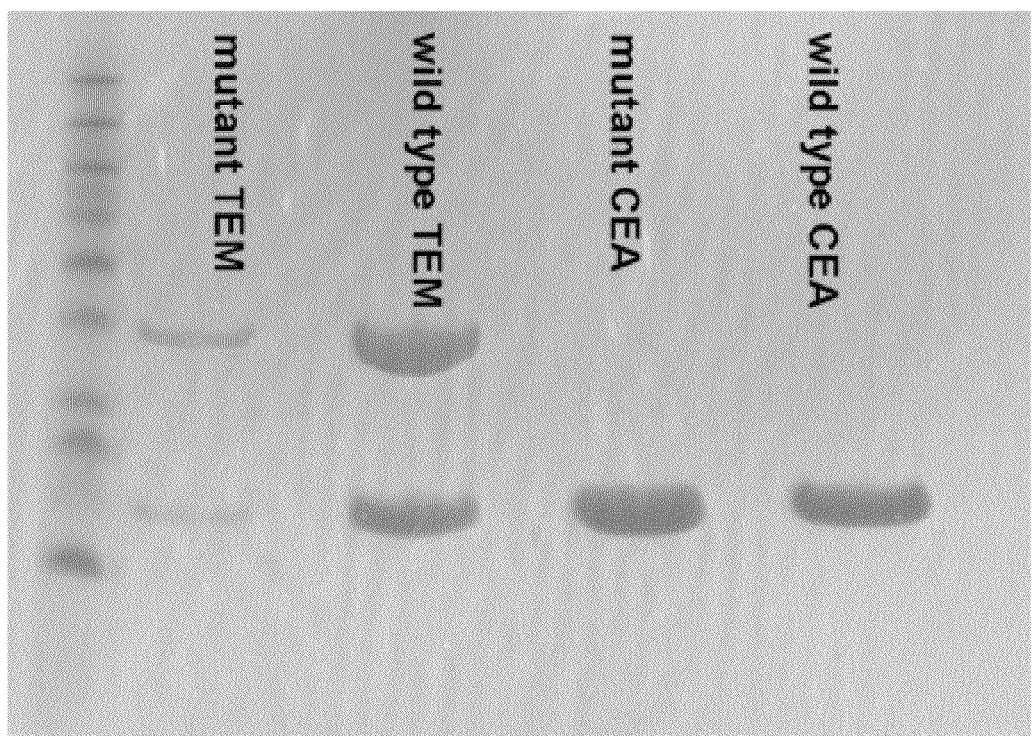
FIG. 3: Coomassie stained 15% SDS PAGE of IMAC purified R103W mutant and wild type VHH. The slower migrating product in the two lanes on the left is β-lactamase, which was complexed to the VHH.

Periplasmic extracts were made from all cultures by resuspending the cells in 4 ml TES (0.2 M Tris-HCl, 0.5 mM EDTA, 0.5 M sucrose; pH 8.0). The suspension was incubated for 30 minutes on ice. Subsequently 6 ml 0.25×TES was added and the incubation on ice was continued for 20 minutes. Periplasts were removed by centrifugation for 20 minutes at 10,000 rpm and 4° C. in SS34-rotor (Sorval). VHH was purified by IMAC using Ni-NTA (QIAGEN). The yields were determined by measuring the OD280 nm using the calculated molar extinction coefficients (VHH TEM04 E(R103)=2.168 and E(W103)=2.582; VHH CEA71 E(R103)=1.444 and E(W103)=1.865) (Table 1). As was observed by Western blot analysis the yield of mutant antibody for VHH TEM04 was much lower than for its wild type, while for VHH CEA71 no difference was found. The purified VHH were analyzed on a coomassie stained PAGE (FIG. 3), which revealed that β-lactamase was co-purified as a complex with VHH TEM04, both for the wild type and the mutant form.

TABLE 1

Production yields of wild type (R on position 203) and mutant (W) VHH expressed per liter of culture.

| VHH | Yield (mg/l) | |
|---|---|---|
| | R (wild type) | W (mutant) |
| TEM04 | 14 ± 5 | 2.3 ± 0.7 |
| CEA71 | 33 ± 4 | 32 ± 2 |

3.2 Antigen Binding Characteristics of VHH CEA71 Variants.

Figure 4:
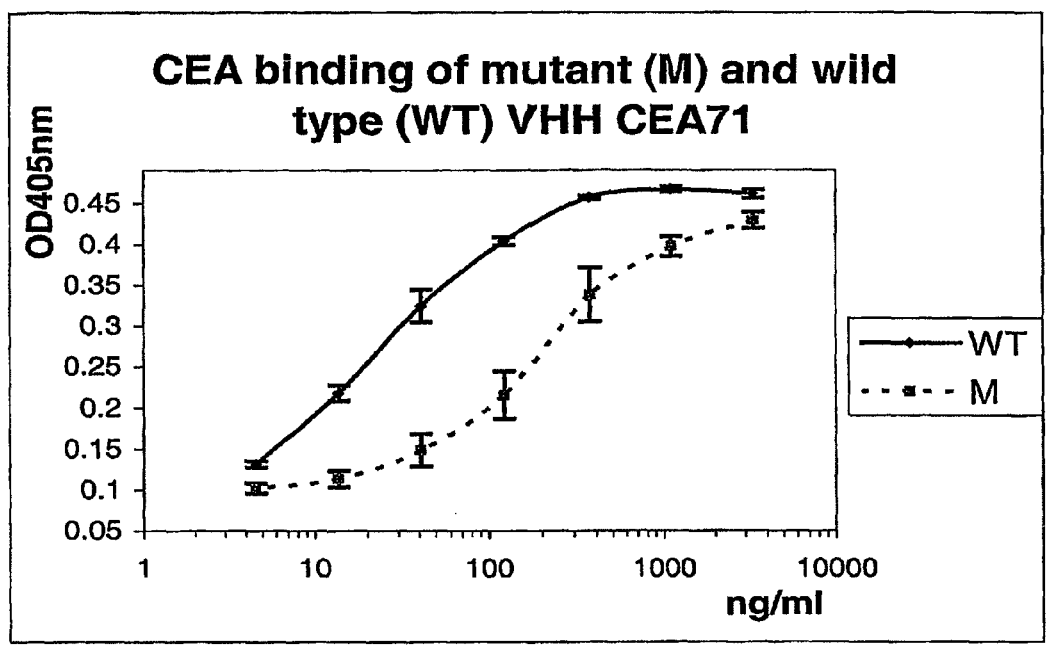
FIG. 4: Antigen binding determined by ELISA of VHH CEA71 wild type (WT) and R103W mutant.

An ELISA was performed to compare the antigen binding characteristics of the wild type and the mutant VHH CEA71. A microtiter plate (Maxisorp, NUNC) was coated overnight at 4° C. with CEA (Scripps) at a concentration of 1 μg/ml (in PBS), and blocked for two hours at room temperature (RT) with 300 μl 1% casein in PBS. The plates were washed three times with PBS-tween. Dilution series (10 μg/ml to 4.57 ng/ml, dilution factor three) of all purified samples were incubated in triplicate (100 μl/well) for 2 hours at RT. Plates were washed six times with PBS-tween, after which binding of VHH was detected by incubation with mouse anti-Histidine mAB (Serotec; 1:1000 diluted; 100 l/well) for 1 hour at RT followed by anti-mouse-alkaline phosphatase conjugate (Sigma, 1:2000 diluted), also for 1 hour at RT. Staining was performed with the substrate PNPP (p-nitrophenyl-phosphate, 2 mg/ml in 1M diethanolamine, 1 mM $Mg_2SO_4$, pH9.8) and the signals were measured after 30 minutes at 405 nm. The CEA wild type VHH still binds at approximately tenfold lower concentrations than the mutant form (FIG. 4). This means that either 90% of the mutant protein is not correctly folded (thus inactive) or that the affinity of the mutated VHH is tenfold lower. For VHH TEM04 no ELISA was performed, but on the coomassie stained gel (FIG. 3) the co-purified β-lactamase seems to have a similar intensity as the VHH, suggesting that the R103W mutant is produced completely in an active form. It therefore can be assumed that the introduction of Tryptophan on position 103 decreases the affinity.

3.3 Solubility of VHH CEA71 Wild Type and R103W Mutant.

Figure 5A:
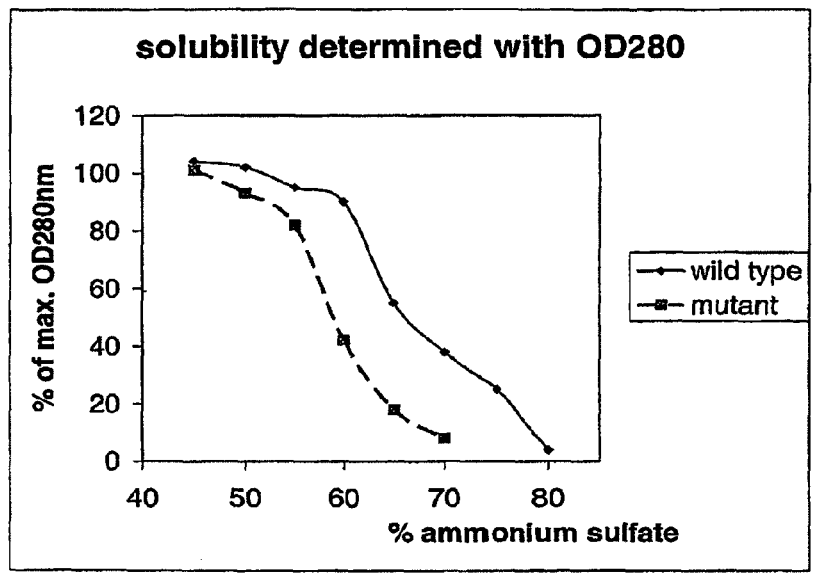
FIG. 5: Examination of the solubility characteristics of VHH CEA72 (wild type and R103W mutant) by determining the concentration of ammonium sulfate at which the fragment started to precipitate. The amount of VHH in the supernatant was measured (A) by protein content with OD280, or (B) by antigen binding in ELISA.
Figure 5B:
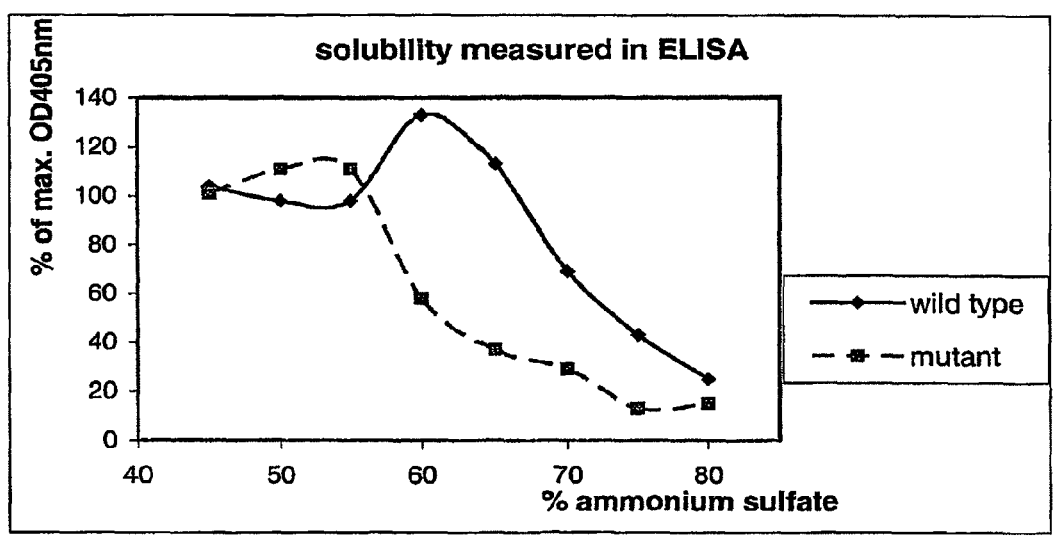

The solubility characteristics were examined by determination of the concentration of ammonium sulfate, at which the VHH starts to precipitate. Therefore a saturated stock solution of ammonium sulfate was prepared by dissolving an excess of salt in a limited volume of water. After equilibration for 2 hours at RT, the solid particles were removed by centrifugation at 4300 rpm for 10 minutes and the supernatant (100% ammonium sulfate solution) was used to make dilutions of 0-80%. 60 μl sample was added to 300 μl ammonium sulphate solution and mixed for 18 hours at 4° C. This mixture was centrifuged for 10 minutes at 13000 rpm in an Eppendorf centrifuge. The amount of soluble VHH in the supernatant was determined in ELISA deduced from the degree of antigen binding (FIG. 5A) and on the other hand by measuring the protein concentration with OD280 (FIG. 5B).

From both types of measurements it can be concluded that the wild type anti-CEA VHH CEA71 started to precipitate at an ammonium sulfate concentration of 65%, while the mutant form shows signs of precipitation at 58%. This experiment clearly demonstrates that the introduction of Tryptophan on position 103 in the context of the wild type sequence of VHH CEA71, which has Arginine on this position, decreases its solubility.

Example 4

Cloning, Selection and Production of Functional Single Domain Heavy Chain Antibody Fragments Dromedaries and llamas were immunized intramuscularly with a cocktail of antigens using Freund's complete adjuvant (first injection) and Freund's incomplete adjuvant (subsequent injections). Dromedaries were immunized with CEA (Carcino Embryonic Antigen), ovalbumine (OVA), PSA (Prostate Specific Antigen), Variant Surface Glycoprotein trypanosome (VSG), β-lactamase, carbonic anhydrase, Cutinase, Potyvirus and Lysozyme. Llamas were immunized with Poly A Binding Protein Type 2 (PABP2), Linoic Acid BSA-conjugate, a humanized mouse mAb to CD40 (Hu-anti-CD40), human serum albumin (HSA), *Salmonella typhimurium*, Rotavirus. Following 6 injections with a one-week interval, a blood sample of 100 ml was collected. PBL cells were separated on a Ficoll-Paque Plus gradient (Amersham Biosciences). Total RNA was isolated from these cells using an acid guanidinium thiocyanate extraction (Chomczynski and Sacchi, 1987) and cDNA was prepared using M-MLV RT (Gibco BRL) and random oligonucleotide primers (Amersham Biosciences). With the primers Call001 (5'-TCCTG-GCTGCTCTTCTACAAG-3') (SEQ ID NO: 98) and Call002 (5'-GGTACGTGCTGTTGAACTGTTCC-3') (SEQ ID NO: 99), annealing to the leader sequence and the CH2 exon of all camelid immunoglobulins respectively, the gene fragments coding for the variable domain were amplified by PCR. To introduce a NcoI restriction site, the gene fragments were reamplified using an equimolar mixture of upstream primers SM017 (5'-CAGCCGGCCATGGCTGATGTGCAGCTG-GTGGAGTCTGG-3' (SEQ ID NO: 101), and SM018 (5'-CCAGCCGGCCATGGCTCAGGTGCAGCTG-GTGGAGTCTGG-3') (SEQ ID NO: 100) in combination with Cll002 in a nested PCR. In the final amplification the A4short primer (5'-CATGCCATGACTCGCGGCCCAGC-CGGCCATGGC-3') (SEQ ID NO: 102) was used on one hand to introduce a SfiI site and on the other hand the primers as described before were used to introduce the key residues on position 103 and a NotI site: primer 1 (R103), primer 2 (R103), primer 3 (K103), primer 4 (Q103), primer 5 (L103), primer 6 (F103) primer 7 (G103), primer 8 (S103), primer 9 (P103), primer 10 (Y103). The PCR products were cloned using the SfiI/NotI restriction enzymes into the phagemid vector pHEN4 (a derivative of pHEN1 (Hoogenboom et al., 1991) with a HA-tag downstream the cloning sites of the heavy chain antibody fragment). The repertoire was expressed on phage following infection with M13K07 helper phages. Specific binders were selected using the principle of phage display and panning (Ghahroudi et al., 1997).

Single domain heavy chain antibodies specific for CEA (CEA1 and CEA72), PSA (N3-A, N8-B, C9-B, C11-B, C12-A, C1-B, C24-A, N13-A, N15-B), HSA (ALB1, ALB2, ALB3, ALB4, ALB5), Hu anti-CD40 (CD40-1, CD40-2, CD40-3, CD40-4, CD40-5, CD40-6, CD40-7), OVA (B13, 1DBOVA11, 1DBOVA23, 1DBOVA43, A2-19, A4-17, B368, R24), VSG (cAbAnO4), β-lactamase (cAbBLA01, cAbTEM04), carbonic anhydrase (1 D2CA30), PABP2 (C4PABP2, E3 PABP2, F6 PABP2), *Salmonella typhimurium* (MPOD6 salmon), Rotavirus (1-F6 RTV), Linoic Acid (LA-1), Cutinase (CutIII19, A4cut9, CACU13, CABCUT4, CU16), Potyvirus (48dpvy, 348DPVY, 1648DPVY, 1048DPVY23, PVYIA15, PVYIA2, PVYIA1, PVY17) and Lysozyme (1D2L28) were isolated and evaluated for expression, binding in ELISA and affinities. The sequences are listed below; amino acid position 103, as determined by the Kabat numbering is indicated in bold,

N3-A
(SEQ ID NO: 103)
DVQLQESGGSLVQPGGSLRLSCAASGFTFSAYYMIWVRQAPGKGLEWVSG

ISANGRDTLYEDSVEGRFAISRDNAKNTLYLQMNSLRSEDTALYYCVIGA

LITGRRGQGTQVTVSS

N8-B
(SEQ ID NO: 104)
DVQLQESGGGLVQPGGSLRLSCAASGFLFSDTYMTWARQAPGKGLEWLGG

ISKDGSGTLYEDSVEGRFTISRDNAKNTLYLQMNSLKSEDTALYYCSTGA

LLPTRPQGQGTQVTVSS

C9-B
(SEQ ID NO: 105)
DVQLQESGGGLVQPGGSLRLSCAASGFTFSNHYMTWVRQAPGKGLEWVSV

ISNDGRYTDYADSVKGRFTISRDNAKNTLYLQMNSLKTEDTALYTCVRGY

YLTNLPAGDRGQGTQVTVSS

C11-B
(SEQ ID NO: 106)
DVQLQESGGGLVQPGGSLRLSCAASGFIFSNTYMTWVRQAPGKGLEWVSG

ISADGRDTLYADSVEGRFAISRDNAKNTLYLQMNSLRSEDTALYYCVTGA

LMTGRRGQGTQVTVSS

C12-A
(SEQ ID NO: 107)
DVQLQESGGGLVRPGGSLRLSCAASGFLFSGTYMTWARQAPGKGLEWLCG

INKDGSGTLYADSVEGRFTCSRDNAKNTLYLQMNSLKSEDTALYYCSTGA

LLPTRPQGQGTQVTVSS

C1-B
(SEQ ID NO: 108)
DVQLQESGGGLVQPGGSLRLSCAASGFTFSTSYMTWARQAPGKGLEWVSG

INRDGNNPLYADSVEGRFTVSRDNAKNTLYLQMNSLKSEDTALYYCVAGA

LVAGARGQGTQVTVSS

C24-A
(SEQ ID NO: 109)
DVQLQESGGGLVQPGGSLRLSCAASGFAFTPSYMSWVRQAPGKGLEWVSV

ISNDGRYTDYADSVKGRFTISRDNAKNKTLYLQMNSLKTEDTALYTCVRG

YYLTNLPAGDRGQGTQVTVSS

N13-A
(SEQ ID NO: 110)
DVQLQESGGGSVQPGGSLRLSCAASGFTFKDASMNWVRQAPGKGLEWVSA

INGGGTVTDYADPMEGRFTISRDNA KNTLYLQMNSLNFEDTALYYCATG

WLFRANNYRGQGTQVTVSS

N15-B
(SEQ ID NO: 111)
DVQLQESGGGSVQAGGSLRLACAATAYTYDSNVLGWFRQAPGKEHEGVAV

IYTGTRTTYYADSVKGRFTISQDNAKNTVYLQMNSLKPGDTAMYFCAANV

RLGGVWSFDYRGQGTQVTVSS

ALB-1
(SEQ ID NO: 112)
QVQLQESGGGLVQPGGSLRLSCAASGFAFSSFPMTWVRQAPGKGLEWVSG

ILEGGGSPAYADSVKGRFTISRDDAKNTLYLQMNSLKPEDTAVYYCAKGY

VYAREGARSQGTQVTVSS

ALB-2
(SEQ ID NO: 113)
QVQLQESGGGLVQPGGSLRLTCTASGFAFSNFGMSWVRQPPGKGLEWVSA

ISADSSTKNYADSVKGRFTISRDNTKKMLYLEMNSLKPEDTAVYHCVIGR

GSASSQGTQVTVSS

ALB-3
(SEQ ID NO: 114)
QVQLQESGGGLVQPGNSLRLSCAASGFAFGNFGMSWVRQAPGKEPEWVSS

IDSIGSDTLYADFVKGRFTISRDNAKSTLYLQMNSLKPEDTAVYYCTIGG

SLSRSSQGTQVTVSS

ALB-4
(SEQ ID NO: 115)
QVQLQESGGGLVQPGNSLRLSCAASGFSFRSFGMSWVRQAPGKGPEWVSS

INSSGDDTRYTDSVKGRFTISRDNAKSTLYLQMNSLKPEDTAVYYCTIGS

SISRSSQGTQVTVSS

ALB-5
(SEQ ID NO: 116)
QVQLQESGGGLVQPGGSLRLTCTASGFAFSSFGMSWVRQPPGKGLEWVSA

ISADSSTKNYADSVKGRFTISRDNDKKMLYLEMNKLKPEDTAVYHCVIGR

GSPSSQGTQVTVSS

CEA1
(SEQ ID NO: 117)
QVQLVESGGGLVQPGGSLRLSCAASGFTFSKYDMSWVRQAPGKGLEWVSR

ISSGGGSTYYADSVKGRFTISRDNAKNTLYLQMNSLKPEDTAVYYCATPT

YSSDYRGLPPGQGTQVTVSS

CEA72

-continued

```
                                   (SEQ ID NO: 118)
QVQLVESGGGLVQPGGSLRLSCAASEFTFSSSYMSWVRQAPGKGLEWVSG

INTDGSFTRYADSVKGRFTISRDNAKNTLYLQMNSLSEDTALYYCAVGG

GLGYGPRGQGTQVTVSS

B13
                                   (SEQ ID NO: 119)
QVQLQASGGGLVQPGGSLRLSCAASGFDFMNVYMTWVRQAPGKGVEWVSG

ISVSGSITHYSESVKGRFTISRDNAKNMLYLQMNSLSEDTARYYCARGG

YNRYYGALGQGTLVTVSS

1DBOVA11
                                   (SEQ ID NO: 120)
QVQLVESGGGSVQ?GESLRLSCVASGFTFDV?YMNWVRQAPGKGLEWVSG

ISASGY?TTYA??VKGRFTISRDNAKNTLYLQMNSL??TRGQGTQVTVSS

1DBOVA23
                                   (SEQ ID NO: 121)
QVQLVESGGGSVQAGGSLIISCAASGFDFSNNYMTWVRQAPGKGVEWVSG

ISVSGSITHYTDSVKGRFTISRDNAKNTLYLQMNSLRSEDTARYYCGTGG

YGRYYGTLGQGTQVTVSS

1DBOVA43
                                   (SEQ ID NO: 122)
QVQLVESGGGLVQPGGSLRLSCVGSGFTFSSYYISWVRQAPGKGLEWVSG

ISGSGATTSYTDSVKGRFTISRDNAKNTVYLQLNSLETEDSAMYYCRLGY

GTPPGGVWPSQRGQGTQVTVSS

A2-19
                                   (SEQ ID NO: 123)
QVQLQASGGGLVQPGGSLKLSCVVSGFLFSNYAFSWVRQAPGKGLEWVST

IGTSSGYTNYAPSVKGRFITSRDNAKNTVYLQLNSLKTEDTAMYYCRRPG

TDERGQGTQVTVSS

A4-17
                                   (SEQ ID NO: 124)
QVQLQASGGGLVQPGGSLRLSCAASGFDFSNVYMTWVRQAPGKGVEWVSG

ISVSGSITHYSDSVKDRFTISRDNAKNTLYLQMNSLSEDTARYYCARGG

YNTYSGALGQGTQVTVSS

B368
                                   (SEQ ID NO: 125)
VQLVESGGGSVQAGGSLILSCTASGLPYKSYCMGWFRQAAGKEPEGVATI

NSGTGSKFYTDSVKGRFTISLDNDNNRVYLEMSSLKPEDTATYYCAAGQR

HSCGYVLKNTDGWTHRAQGTQVTVSS

R24
                                   (SEQ ID NO: 126)
SAQVQLQASGGGLVQPGGSLKLSCVVSGFLFSNYAFSWVRQAPGKGLEWV

STIGTSSGYTNYAPSVKGRFTISRDNAKNTVYLQLNSLKTEDTAMYYCRR

PGTDERGQGTQVTVSS cAbAn04
                                   (SEQ ID NO: 127)
QVQLVESGGGSVEAGGSLRLSCVVSGYSVSIGCMAWFRQAPGSGREGVAG

ISRGGSMTDYTASVKGRFTISRD-ND QRTVTLQMNSLKPEDTAVYYCAR

DGPEIATMIGGSRGRGTQVTVSS cAbBLA01
                                   (SEQ ID NO: 128)
QLQLVESGGGSVQSGGSLRLSCKVSGYIGSTNCMGWFRQAPGKEREGVAS

LFTGSGNTYYGDSVKGRFTISEDNAKNTVSLQMNSLKPEDTAMYYCASSS

NVGSDESCGRKNTRQFVYTYQGQGTQVTVSS cAbTEM04
                                   (SEQ ID NO: 129)
QVQLVESGGGLVQAGGSLRLSCAASGFTFSSAWMTWVRQAPGKGLEWVTS

IATDGSTDYADSVKGRFTISRDNAKNTLYLQLNSLNTEDTAVYYCAKDRW

GYVVRGQGTQVTVSS

1D2CA30
                                   (SEQ ID NO: 130)
QVQLVESGGGSVQAGGSLRLSCAASGYTVSTYCMGWFRQAPGKEREGVAT

ILGGSTYYGDSVKGRFTISQDNAKNTVYLQMNSLKPEDTAIYYCAGSTVA

STGWCSRLRPYDYHYRGQGTQVTVSS

C4 PABP2
                                   (SEQ ID NO: 131)
QVQLQESGGGLVQPGGSLRLSCAASGFTFSRSWMYWVRQAPGKGLEWVSS

ITPGGSEPFYVDSVKGRFTISRDNAKNTLYLQMNSLKSEDTAVYFCAKDS

KNGPRGQGTQVTVSS

E3 PABP2
                                   (SEQ ID NO: 132)
QVQLQESGGGLVQPGGSLRLSCAASGFTFSRSWMYWVRQAPGKGLEWVSS

ITPGGTEAFYADSVKGRFTISRDNAKNTLYLQMNSLKSEDTALYFCAKDS

KNGPRGQGTQVTVSS

F6 PABP2
                                   (SEQ ID NO: 133)
QVQLQESGGGLVQPGGSLRLSCATSGFISDYWMYWVRQAPGKGLEWVSSI

TPGASTTLYADSVKGRFTISRDNAKNTLYLQMNSLKSEDTAVYYCAKGSK

IGPRGQGTQVTVSS

LA-1
                                   (SEQ ID NO: 134)
QVQLQDDSGGGLVQPGGSLKLSCAASGFTFSNYEMSWVRQAPGKGLEWVS

SINNGGDITYYANSVKGRFTISRDNTKNTLYLQMNSLKSEDTAVYYCKVP

NRRLRGPGTQVTVSS

CD40-1
                                   (SEQ ID NO: 135)
QVQLLVESGGGLVQPGGSLRLSCAAAGFTFSNYAMSWVRQAPGKGLEWVS

GIKSGGGRTYYADSVKGRFTISRDNAKNTLTLQLNSLKTEDTAMYYCAKG

ARYDSDYDVYTWLDSYSGQGTQVTVSS

CD40-2
                                   (SEQ ID NO: 136)
EVQLVESGGGLVQAGGSLELSCSFGGRAFDRYFMAWFRQAPGKGLEWVSR

IYSGGSTSYADSVKGRFTISRDNAKNTLYLQMNNLKPEDTAVYYCDIAGR

RGQGIQVTVSS

CD40-3
                                   (SEQ ID NO: 137)
EVQLVESGGGLVQAGDSLRLSCAASGRTFNTVDMGWFRQAPGKEREFVAH

ISWRGGSTYYADSVKGRFTISRDNAKNTLYLQMNNLKPEDTAVYYCDIAG

RRGQGTQVTVSS

CD40-4
                                   (SEQ ID NO: 138)
QVQLVESGGGLVQPGGSLRLSCAASGFAFSRYSMYWVRQAPGKGLEWVSE

IYPDGNGWYTSSVKGRFTISRDNDKNMLYLQMNSLKPDDTAVYYCALSRS
```

-continued

CD40-5
(SEQ ID NO: 139)
EVQLVESGGGLVQAGGSLELSCSFGGRAFDRYFMAWFRQAPGKGLEWVSR
IYSGGSTSYADSVKGRFTISRDNAKNTLYLQMNNLKPEDTAVYYCDIAGR
RGQGIQVTVVS

CD40-6
(SEQ ID NO: 140)
EVQLVESGGGLVQAGDSLRLSCAASGRTFNTVDMGWFRQAPGKEREFVAH
ISWRGGSTYYADSVKGRFTISRDNAKNTLYLQMNNLKPEDTAVYYCDIAG
RRGQGTQVTVSS

CD40-7
(SEQ ID NO: 141)
AVQLEESGGDSVQAGGSLRLSCAASGFTFSRYSMYWVRQPPGKGLEWVSE
IYPDGNGWYTSSVKGRFTISRDNDKNMLYLQMNSLKPDDTAVYYCALSRS
GQGRGQGTRVTVSS

MPOD6 Salmon
(SEQ ID NO: 142)
QVQLQESGGGLVQPGGSLRLSCAASGFTFNDYFMNWVRQAPGKGLEWVSG
IYSDGSKTYYGDSVKGRFTISRDNAKNTLYLQMNSLKSEDSAVYYCTRGT
GWSSTPYTYRGQGTQVTVSS 1-F6 RTV
(SEQ ID NO: 143)
QVQLQEVRGRLVQLGGSLRLSCAASGFTFKYYAMSWVRQAPGKGLEWVSY
INDNGGYTDYSDSVKGRFTISRDNAKNTLYLHMNRLKPEDTAVYFCAKWD
TDAVSSSRYKTHNGDIRGPGTQVTVSS CUTIII19
(SEQ ID NO: 144)
QVQLVESGGGLVQAGESLTLSCTASGGSFNNWHMGWFRQAPGTEREFVAA
IRRAYGSTFYADSVKGRFTIARDNAKNTVYLQMSSLKPEDSAVYYCAAKR
AFRVGGDFEYYGQGTQVTVSS A4cut9
(SEQ ID NO: 145)
QVQLQASGGGLVQPGGSLRLSCAASGFTFSTYYMNWVRQAPGKGLEWVPG
INKDGSVSHYADSVKGRFTISRDNAKNTLYLRMNSLKSEDTALYYCATIA
GFRVGGGPGGTQVTVSS CACU13
(SEQ ID NO: 146)
DVQLVESGGGLVQPGGSLRLSCAASGFRFDSVAMTWVRQTPGKGLEWVSS
ISWDGTTTSYAASVKGRFTISRDNAKNTLYLQLDSLKTEDTAMYYCTKTG
VDYRDSRDRGRGTQVTVSS CABCUT4
(SEQ ID NO: 147)
QVQLVESGGGLVQPGGSLRLSCAASGFRFDSVAMTWVRQAPGKGLEWVSS
ISWDGTTTSYAASVKGRFTISRDNAKNTLYLQLDSLNTEDTAMYYCTKTG
VDYRDSRSRGQGTQVTVSS Cu16
(SEQ ID NO: 148)
QVQLVESGGGSVQAGGSLKLTCELSGFNGRSNCMGWFRQVLGKDREGVAA
INHPEGSEFYDDSVKGRFKITRDGLKDADSLQMNNLKPEDTATYYCALRP
YDCYSGAWSPADFYYRGARGTQVTVSS 48dpvy3
(SEQ ID NO: 149)
QVQLQASGGGSVEAGGSLRLSCAASGDTAKLNCMAWFRQAPGKERERVAS
LSTRLTTTSYTDSVKGRFTISQDTATNTVYLEMNSLQPEDTAVYYCQLSR
GGTNYRGQGTLVTVSS 48DPVY16
(SEQ ID NO: 150)
QVQLQASGGGSVQAGGSLRLSCAASGYTYSSNCMGWFRQALGKEREGVAA
IYTGGGSTYYADSVKGRFTISQDNAKNTVLYQMNSLKPEDTAMYYCAASL
LPLVAGIGVWDAFDYRGQGTQVTVSS 48DPVY10
(SEQ ID NO: 151)
QVQLQASGGGSVQAGGSLRLSCVASQYEYSNNYIAWFRQAPGKEREGVAA
IYTGGVTRASPYYADPVKGRFSISKDNAKNTVYLQMNDLKPEDSGTYICA
SSIHGLGNPLRSEFSYYGQGTLVTVSS 48DPVY23
(SEQ ID NO: 152)
QVQLQASGGGSVEAGGSLRLSCAASGDTAKLNCMAWFRQAPGKERERVAL
LSTRLTTTSYTDSVKGRFTISQDTATNTVYLEMNSLQPEDTAIYYCAARW
AGRSCLVSVYDYYGQGTLVTVSS PVYIA15
(SEQ ID NO: 153)
QVQLVESGGGLVQPGGSLRLSCAASGFTFSNYAMSWVRQAPGKGLEWVSG
IKSGGGRTYYADSVKGRFTISRDNAKNTLTLQLNSLKTEDTAMYYCAKGA
RYDSDYDVTWLDSYSGQGTQVTVSS PVYIA2
(SEQ ID NO: 154)
DVQLVESGGGSVQAGGSLRLSCTASGLRLNTYHMSWVRQAPGKGLEWVST
IYIGGTTTSHANSVSGRFTISRDDAKNTLYLQMNNLKPEDTAVYFCATGS
VNAYGVKGQGTQVTVSS PVYIA1
(SEQ ID NO: 155)
QVQLVESGGGSVQAGGSLTLSCTVSGYDFNRCSMNWYRENPGKEREFVAG
IDSDGTTTYADSVKGRFTISHDNTRNTLYLQMNSLKSEDTALYYCRLGGL
RTWPQYGYRGQGTQVTVSS PVY17
(SEQ ID NO: 156)
QVQLVESGGGLVQPGGSLRLSCTASGLRLNTYHMSWVRQAPGKGLEWVST
IYIGGTTTSHANSVSGRFTISRDDAKNTLYLQMNNLKPEDTAVYFCATGS
VNAYGVKGQGTLVTVSSAA 1D2L28
(SEQ ID NO: 157)
QVQLVESGGGLVQPGGSLRLSCAASGFAFSIYRMSWVRQAPGQGLEWVSS
IDSGGGITYYADSVKGRFTISRDNAKNTLYLQLNSLKTEDTAMYYCARGH
YLYDDIFTGAKGQGTQVTVSSGR For each construct 10 ml pre-cultures were started in TB containing 100 μg/ml ampicillin and 2% glucose. For each pre-culture, 4×330 ml culture was started at 37° C. in TB containing 100 μg/ml ampicillin with 3 ml of the overnight culture. Cultures were induced with 1 mM IPTG at OD600 nm=0.4 and grown overnight at 28° C.

Periplasmic extract was prepared for all overnight cultures. The overnight cultures were centrifuged for 10 minutes at 10,000 rpm at 40° C. The supernatant was removed and the pellet was re-suspended in 16 ml TES (0.2 M Tris-HCl, pH=8.0, 0.5 mM EDTA and 0.5 M sucrose). This mixture was incubated for 30 minutes on ice. 24 ml 0.25×TES was added, incubated on ice for 20 minutes and centrifuged for 20 minutes at 10,000 rpm. The supernatant was purified on Ni-NTA (QIAGEN), and dialyzed overnight against PBS. OD280 was measured and the yield (in mg) of purified material per liter of culture was determined. Kd's were determined on BIAcore are given in the table below.

| Name of binder | Antigen recognized by antibody | Kd (nM) | Expression level (mg/l culture, purified material) | Host |
|---|---|---|---|---|
| N3-A | Prostate specific antigen | — | 0.25 | Dromedary |
| N8-B | Prostate specific antigen | 1.6 | 6.2 | Dromedary |
| C9-B | Prostate specific antigen | 3.9 | 2.1 | Dromedary |
| C11-B | Prostate specific antigen | 2.6 | 6.1 | Dromedary |
| C12-A | Prostate specific antigen | 2.6 | 1.2 | Dromedary |
| C1-B | Prostate specific antigen | 0.8 | 0.75 | Dromedary |
| C24-A | Prostate specific antigen | — | 5.0 | Dromedary |
| N13-A | Prostate specific antigen | — | 0.25 | Dromedary |
| N15-B | Prostate specific antigen | — | 0.65 | Dromedary |
| CEA1 | Carcino Embryonic Antigen | | | Dromedary |
| CEA72 | Carcino Embryonic Antigen | | 8.4 | Dromedary |
| B13 | ovalbumin | | <13 | Dromedary |
| 1DBOVA11 | ovalbumin | | | Dromedary |
| 1DBOVA23 | ovalbumin | | | Dromedary |
| 1DBOVA43 | ovalbumin | | | Dromedary |
| A2-19 | ovalbumin | | | Dromedary |
| A4-17 | ovalbumin | | | Dromedary |
| B368 | ovalbumin | | | Dromedary |
| R24 | ovalbumin | | | Dromedary |
| cAbAn04 | Variant surface glycoprotein trypanosome | | | Dromedary |
| cAbBLA01 | β-lactamase | <1 | 0.4 | Dromedary |
| cAbTEM04 | TEM1 | | | Dromedary |
| 1D2CA30 | Carbonic anhydrase | | | Dromedary |
| A4Cut9 | Cutinase | | | Dromedary |
| CACU13 | Cutinase | | | Dromedary |
| CABCUT4 | Cutinase | | | Dromedary |
| CU16 | Cutinase | | | Dromedary |
| 48dpvy | Potyvirus | | | Dromedary |
| 348DPVY | Potyvirus | | | Dromedary |
| 1648DPVY | Potyvirus | | | Dromedary |
| 1048DPVY23 | Potyvirus | | | Dromedary |
| PVYIA15 | Potyvirus | | | Dromedary |
| PVYIA2 | Potyvirus | | | Dromedary |
| PVYIA1 | Potyvirus | | | Dromedary |
| PVY17 | Potyvirus | | | Dromedary |
| 1D2L28 | Lysozyme | | | Llama |
| LA-1 | Linoic acid | | | Llama |
| C4 PABP2 | Poly A Binding Protein Type 2 | | | Llama |
| E3 PABP2 | Poly A Binding Protein Type 2 | | | Llama |
| F6 PABP2 | Poly A Binding Protein Type 2 | | | Llama |
| CD40-1 | humanised mouse mAb to CD40 | 2 | 8 | Llama |
| CD40-2 | humanised mouse mAb to CD40 | | | Llama |
| CD40-3 | humanised mouse mAb to CD40 | | | Llama |
| CD40-4 | humanised mouse MAb to CD40 | | | Llama |
| CD40-5 | humanised mouse mAb to CD40 | | | Llama |
| CD40-6 | humanised mouse mAb to CD40 | | | Llama |
| CD40-7 | humanised mouse mAb to CD40 | | | Llama |
| MPOD6 | Salmonella salmon Typhimurium | | | Llama |
| 1-F6 RTV | Rotavirus | | | Llama |
| CutIII19 | Cutinase | | | Llama |
| ALB-1 | Human serum albumin | | 15 | Llama |
| ALB-2 | Human serum albumin | | 15 | Llama |
| ALB-3 | Human serum albumin | | 15 | Llama |
| ALB-4 | Human serum albumin | | 15 | Llama |
| ALB-5 | Human serum albumin | | 15 | Llama |

Alignment of the CEA1 binder (SEQ ID NO: 117) and a human VH3 germline (DP-47) (SEQ ID NO: 158) revealed a high degree of homology (two amino acid changes in FR1 on position 1 and 5 and four changes in FR3 on position 74, 83, 84 and 94), as shown below:

```
DP-47  EVQLLESGGGLVQPGGSLRLSCAASGFTFS SYAMS WVRQAPGKGLEWVSAISGSGGSTYY
CEA1   QVQLVESGGGLVQPGGSLRLSCAASGFTFS KYDMS WVRQAPGKGLEWVSRISSGGGSTYY

DP-47  ADSVKG  RFTISRDNSKNTLYLQMNSLRAEDTAVYYCAK  ---------------------
CEA1   ADSVKG  RFTISRDNAKNTLYLQNNSLKPEDTAVYYCAT  PTYSSDYRGLPPGQGTQVTVSS
```

A specific binder for the CEA tumor antigen, with high homology to the human germline gene DP-47 was therefore an ideal candidate to further humanize and evaluate the influence of mutagenesis on binding affinity in ELISA and BIAcore.

Mutagenesis of the residues in FR1 had no significant influence on specificity, binding affinity and expression level. Mutagenesis of most of the FR3 residues did not result in loss of specificity, affinity and expression levels. The most humanized and best performing CEA1 mutant was chosen for immunogenicity studies. Baboons were immunized intravenously, intramuscularly and subcutaneously with a weekly dose of 1 mg/kg body weight. Blood samples were taken and humoral response was evaluated in ELISA. No significant antibody response was raised against the CEA1 mutant.

Example 5

Construction of a Functional Single Domain Heavy Chain Antibody Fragment Library Derived from Human and Mouse VH cDNA templates were made starting from blood samples from 20 non-immunized human donors (or from other species containing antigen binding molecules with an Ig-fold). The peripheral blood lymphocytes (PBL) were isolated on Ficoll-Paque gradients (Amersham Biosciences). Total RNA was prepared individually from the 20 samples of PBL's as described in example 4. First strand cDNA was also individually synthesized from total RNA with random hexamers as primers (as in example 4).

Mutagenesis was carried out using a Framework 1 specific primer that is 5' linked to a SfiI site, as backward primer, and the mutagenic primer:
3'-ACC CGA GGA GCC TGG GAC CAG TGG CAG-5' (SEQ ID NO: 159)
or
3'-ACC CCG GTG AGG AGG GTC CAG TGG CAG-5 (SEQ ID NO: 160)
as forward primer. The DNA obtained was cut with BseRI and ligated to the double stranded primer:
5'-pC GTC AGG GGC CAA GGA ACC CAG GTC ACC GTC TCC TCA-3' (SEQ ID NO: 161)
3'-CTG CAG TCC CCG GTC CCC TGG GTC CAG TGG CAG AGG AGT-5' (SEQ ID NO: 162) for the PCR product obtained with the first mutagenic primer, or
5'-pAGG GGC CAA GGA ACC CAG GTC ACC GTC TCC TCA-3' (SEQ ID NO: 163)
3'-GT TCC CCG GTC CCC TGG GTC CAG TGG CAG AGG AGT-5' (SEQ ID NO: 164)
for the PCR product obtained with the second mutagenic primer.

This primer restores the CDR3 and Framework 4 coding regions. The resulting DNA was amplified using the same forward primer as above, and using
3'-C TGG GTC CAG TGG CAG AGG AGT CGCCGGCG-5' (SEQ ID NO: 165)
as backward primer. This primer created a NotI site at the end of the VH coding sequence. The resulting material was cut with SfiI and NotI and the resulting fragment cloned in pHEN4 to yield a phage display library.

The library was selected with a panel of antigens, such as Human Serum Albumin and human IgG1, thereby obtaining large numbers of antigen specific antibody fragments. Sequence analysis revealed the introduced residue on position 103. The produced and His6-tagged VH fragments showed good solubility characteristics, good specificity (not reactive against irrelevant antigens) and high affinities (range of 2 to 50 nM).

A mouse was immunized with a set of antigens (CEA and PSA) and after four weeks the spleen was removed, homogenized in guanidinium thiocyanate buffer with a Polytron homogenizer, debris removed by low speed centrifugation and total RNA extracted using the method described before. As was described above the mouse VH encoding gene segments were amplified thereby introducing the variant residues on position 103. Upon selection high affinity VH fragments were selected with good characteristics with respect to solubility.

Example 6

Isolation, Sequencing and Production of Human TNF Specific Fragments

Selection of binders for tumor necrosis factor α (TNF) from a phage library was carried out as described in Example 4. After panning the library, 48 individual clones were selected and tested in a phage ELISA on immobilized TNF and BSA.

The clones for which the signal on TNF was superior to the one obtained on BSA were selected for further characterization. By sequencing the selected clones, we were able to eliminate identical clones and to demonstrate that W103 was no longer encoded in the selected fragments.

The gene segments encoding the selected antibody fragment were recloned in the pHEN6 expression vector as described in example 3, which allowed us to produce the recombinant antibody fragment as soluble periplasmic proteins. The recombinant antibody fragments were purified to homogeneity from the periplasmic fraction by IMAC on Ni-NTA agarose and subsequent gel-filtration chromatography on Superdex-75. The purity was determined by SDS-PAGE.
6.1 Applications of anti-TNF Antibody Fragments.
6.1.1 Therapeutic Applications.

Anti-TNF specific fragments were tested in L929 murine fibrosarcoma cells following the protocol as described by Ameloot et al. (2001). L929 cells were seeded in 96-wells microtiter plates at 30,000 cells per wells. The next day, purified recombinant antibody fragments were added to some wells, whereas only PBS was added to control wells. In this experiment the final concentration of antibody fragment was 1 micromolar.

Subsequently a lethal dose of TNF was added to those wells where antibody was added and also to part of the control wells. After 18 hours, the level of surviving cells was estimated by the calorimetric method. In this way we demonstrated that these antibody fragments have the ability to neutralize the cytotoxic effect of TNF and have therapeutic potential.

6.1.2 Diagnostic Application of Anti-TNF VHH in ELISA.

To individual wells of a microtiter plate, we added 100 µl of the antibody fragments at a concentration of 5 µg/ml in PBS. After incubation overnight at 4° C. the plate is blocked with 1% BSA in PBS. The presence of functional immobilized antibody fragment was demonstrated by the binding of biotinylated TNF at 1 µg/ml. The presence of bound biotinylated TNF was demonstrated with streptavidin-alkaline phosphatase conjugate and subsequent reaction with para-nitrophenyl-phosphate.

6.1.3 Application of Anti-TNF VHH in Antibody Arrays.

Two different formats of antibodies arrays were tested, i.e. on nitrocellulose filters and glass slides. For the filter method 2 µl of the purified antibody fragments at concentration of 1 mg/ml in PBS were spotted with a micropipette on a nitrocellulose sheet. After drying, the sheet was blocked with 1% BSA in PBS. The presence of functional immobilized antibody fragment on the nitrocellulose sheet was demonstrated with biotinylated TNF. The presence of bound TNF was demonstrated with streptavidin-alkaline phosphatase conjugate and NBT-BCIP reagent. The appearance of dark spots on those positions where the TNF-specific fragments were applied proved that these antibody fragments retain functionality when passively coated on a solid support. This approach can be used for random screening and selection of antigen-specific fragments.

For the glass slide type of antibody array the anti-TNF antibody fragments were covalently immobilized. Purified antibody fragments were diluted to a concentration of 200 µg/ml in PBS containing 20% glycerol. The samples where transferred to wells of a 384 well microtiter plate. Subsequently an automated contact printer was used to deliver 5 nanoliter of the antibody solutions to a commercially available glass slide (Telechem-Superaldehyde).

After application of the samples, the glass slide was incubated for 1 hour in a humid chamber, to allow the reaction between the reactive aldehydes present on the glass slide and the lysine groups present on the antibody fragment surface to proceed.

The slide was subsequently blocked with 1% BSA/PBS, subsequently incubated with Cy3-modified TNF (fluorescent label Cy3-Amersham Biosciences) at 1 µg/ml and finally washed with PBS to remove unbound labeled TNF. After scanning the fluorescence intensity present on the surface of the slide, we observed an enhanced signal at those positions where the TNF specific antibody fragments were applied.

This result demonstrated that these antibody fragments were covalently immobilized with retention of binding capacity.

6.1.4 Affinity Chromatography.

Purified antibody fragments at a concentration of at least 1 mg/ml were dialyzed against 0.1 M sodium bicarbonate and subsequently mixed with 1 ml gel suspension (CNBr-activated Sepharose) following the protocol as described by the manufacturer (Amersham Biosciences).

After incubation for 3 hr, 100 µl of a 1M Tris pH 8 solution was added. After extensive washing, in order to remove unbound protein, the affinity resin was resuspended in 1 ml PBS.

The functionality of the immobilized anti-TNF antibody resin was tested as described below. To 1 ml of human plasma 10 µg of purified TNF was added. We then added 100 µl of the affinity resin. After of overnight incubation of this suspension, the resin was washed extensively with PBS. The pelleted beads were subsequently resuspended in 100 µl of a solution containing 1% SDS solution and boiled for 10 minutes. After centrifugation 20 µl of the supernatant was loaded on SDS-PAGE. A band of the expected molecular weight was enriched in the analyzed sample.

REFERENCES

Ameloot, P., Declercq, W., Fiers, W., Vandenabeele, P. and Brouckaert, P. (2001), J Biol Chem 276: 27098-27103.

Anker, R., Zavala, F. and Pollok, B. A. (1990). Eur J Immunol 20: 2757-2761.

Babu, K. S., Arshad, S. H. and Holgate, S. T. (2001). Expert Opin Biol 1:1049-1058.

Bodtger, U., Poulsend, L. K., Jacobi, H. H. and Mailing, H. J. (2002). Allergy 57: 297-305.

Chomczynski, P. and Sacchi, N. (1987) Anal Biochem 162: 156-159.

Chukwuocha, R., Hsiao, E. T., Shaw, P., Witztum, J. L. and Chen, P. P. (1999). J Immunol 163: 4604-4611.

Chothia, Novotny, Bruccoleri Karplus, (1985), J. Mol. Biol. 186, 651-663.

Desmyter et al, (1996), Nature structural biology, v 3: 803-811

Dimasi, N., Martin, F., Volpari, C., Brunetti, M., Biasiol, G., Altamura, S., Cortese, R., De Francesco, R., Steinkuhler, C. and Sollazzo, M. (1997). J Virol, 71: 7461-7469.

Ghahroudi, M. A. Desmyter, A., Wyns, L., Hamers, R. and Muyldermans, S. (1997). FEBS Letters 414: 521-526.

Gordon, F. H., Hamilton, M. I., Donoghue, S., Greenlees, C., Palmer, T., Rowley-Jones, D., Dhillon, A. P., Amlot, P. L. and Pounder, R. E. (2002). Aliment Pharmacol Ther 16: 699-705.

Hamers-Casterman C., Atarhouch, T., Muyldermans, S., Robinson, G., Hamers, C.; Songa E. B., Bendaham, N. and Hamers, R. (1993). Nature, 363: 446-448.

Hoogenboom H. R., Griffiths A. D., Johnson K. S., Chiswell D. J., Hudson P., and Winter, G. (1991). Nucleic Acid Res 19: 4133-4137.

Harmsen, M. M., Ruuls, R. C., Nijman, I. J., Niewold, T. A., Frenken, L. G. J. and de Geus, B. (2000). Mol Immunol, 37: 579-590.

Hommes, D. W., van de Heisteeg, B. H., van der Spek, M., Barteisman, J. F. and van Deventer, S. J. (2002). Inflamm Bowel Dis 8: 81-86.

Kabat, E.; Wu, T., T.; Perry, H., M.; Gottesman, K., S.; Foeller, C. 1991, US Public Health Services, NIH, Bethesda, Md.

Muyldermans, S., Cambillau, C. and Wyns, L. (2001). Trends Biochem Sci, 26: 230-235.

Nguyen, V. K., Hamers, R., Wyns, L. and Muyldermans, S. (2000). EMBO J, 19: 921-930.

Nuttall, S. D., Irving, R. A. and Hudson, P. J. (2000). Curr Pharm Biotechnol, 1: 253-263.

Pessi, A., Bianchi, E., Crameri, A., Venturi, S., Tramonatno, A. and Solazzo, M. (1993). Nature, 362: 367-369.

Quiocho, F. A. (1993). Nature, 362: 293-294.

Riechman (1996), J. Mol. Biol. 259: 957-969.

Sollinger, H., Kaplan, B., Pescovitz, M. D., Philosophe, B., Roza, A., Brayman, K. and Somberg, K. (2001). Transplantation 72: 1915-1919.

Vu, K. B., Ghahroudi, M. A., Wyns, L. and Muyldermans, S. (1997). Mol Immunol, 34, 1121-1131.

The invention claimed is:

1. An isolated functional immunoglobulin V-domain from the H-chain of a functional heavy chain antibody ($V_{HH}$) or from the H-chain of a four-chain antibody ($V_H$), wherein the amino acid at position 45 is leucine (L) or wherein the amino acid at position 45 is replaced with leucine (L) and wherein the amino acid at position 103 is arginine (R) or wherein the amino acid at position 103 is replaced with arginine (R), wherein said immunoglobulin V-domain is not stabilized by a disulfide bridge formed between CDR3 and either CDR1 or CDR2, further comprising leucine at position 108, said positions determined according to the Kabat numbering.

2. An isolated functional immunoglobulin V-domain from the H-chain of a functional heavy chain antibody (VHH) or from the H-chain of a four-chain antibody (VH), wherein the amino acid at position 45 is leucine (L) or wherein the amino acid at position 45 is replaced with leucine (L) and wherein the amino acid at position 103 is arginine (R) or wherein the amino acid at position 103 is replaced with arginine (R), wherein said immunoglobulin V-domain is not stabilized by a disulfide bridge formed between CDR3 and either CDR1 or CDR2, wherein said immunoglobulin V-domain does not have a cysteine residue in the CDR3 and in either CDR1 or CDR2, and further comprising leucine at position 108, said positions determined according to the Kabat numbering.

3. The isolated functional immunoglobulin V-domain of claim 1, further comprising valine (V) at position 37, glycine (G) at position 44 and/or tryptophan (W) at position 47, said positions determined according to the Kabat numbering.

4. The isolated functional immunoglobulin V-domain of claim 2, further comprising valine (V) at position 37, glycine (G) at position 44 and/or tryptophan (W) at position 47, said positions determined according to the Kabat numbering.

5. An isolated polypeptide comprising the isolated functional immunoglobulin V-domain of claim 3, wherein said polypeptide is a dimer, trimer or multimer.

6. An isolated fusion polypeptide comprising the isolated functional immunoglobulin V-domain of claim 4, wherein said polypeptide is a dimer, trimer or multimer.

7. An isolated fusion polypeptide comprising the isolated functional immunoglobulin V-domain of claim 1, wherein said polypeptide is a dimer, trimer or multimer.

8. An isolated fusion polypeptide comprising the isolated functional immunoglobulin V-domain of claim 2, wherein said polypeptide is a dimer, trimer or multimer.

9. A pharmaceutical composition comprising the isolated functional immunoglobulin V-domain according to any of claims 1 to 4, optionally in combination with a suitable excipient.

10. A pharmaceutical composition comprising the isolated polypeptide according to any of claims 5 to 8, optionally in combination with a suitable excipient.

* * * * *

SEQUENCE LISTING

<160> NUMBER OF SEQ ID NOS: 165

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 345
<212> TYPE: DNA
<213> ORGANISM: Artificial Sequence
<220> FEATURE:
<223> OTHER INFORMATION: anti-beta-lactamase VHHTEM04, wild type

<220> FEATURE:
<221> NAME/KEY: CDS
<222> LOCATION: (1)..(345)

<400> SEQUENCE: 11

```
cag gtg cag ctg gtg gag tct ggg gga ggc ttg gtg cag gct gga ggg       48
Gln Val Gln Leu Val Glu Ser Gly Gly Gly Leu Val Gln Ala Gly Gly
1               5                   10                  15 tct ctg agg ctc tcc tgt gca gcc tct gga ttc acc ttc agt agc gca       96
Ser Leu Arg Leu Ser Cys Ala Ala Ser Gly Phe Thr Phe Ser Ser Ala
            20                  25                  30 tgg atg aca tgg gtc cgc cag gct cca ggg aag gga ctc gag tgg gtc      144
Trp Met Thr Trp Val Arg Gln Ala Pro Gly Lys Gly Leu Glu Trp Val
        35                  40                  45 aca agt att gct acg gat ggg tcc acg gac tat gca gac tcc gtg aag      192
Thr Ser Ile Ala Thr Asp Gly Ser Thr Asp Tyr Ala Asp Ser Val Lys
    50                  55                  60 ggc cga ttc acc atc tcc aga gac aat gcc aag aac acg ctg tat ctg      240
Gly Arg Phe Thr Ile Ser Arg Asp Asn Ala Lys Asn Thr Leu Tyr Leu
65                  70                  75                  80 caa tta aac agc ctg aac act gaa gac acg gcc gtg tat tac tgt gca      288
Gln Leu Asn Ser Leu Asn Thr Glu Asp Thr Ala Val Tyr Tyr Cys Ala
                85                  90                  95 aaa gat cgt tgg ggg tat gtc gta aga ggc cag ggg acc cag gtc acc      336
Lys Asp Arg Trp Gly Tyr Val Val Arg Gly Gln Gly Thr Gln Val Thr
            100                 105                 110 gtc tcc tca                                                           345
Val Ser Ser
        115
```

<210> SEQ ID NO 12
<211> LENGTH: 115
<212> TYPE: PRT
<213> ORGANISM: Artificial Sequence
<220> FEATURE:
<223> OTHER INFORMATION: Synthetic Construct

<400> SEQUENCE: 12

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Ser Ala
            20                  25                  30

Trp Met Thr Trp Val Arg Gln Ala Pro Gly Lys Gly Leu Glu Trp Val
        35                  40                  45

Thr Ser Ile Ala Thr Asp Gly Ser Thr Asp Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Asn Thr Glu Asp Thr Ala Val Tyr Tyr Cys Ala
                85                  90                  95

Lys Asp Arg Trp Gly Tyr Val Val Arg Gly Gln Gly Thr Gln Val Thr
            100                 105                 110

Val Ser Ser
        115
```

<210> SEQ ID NO 13
<211> LENGTH: 6
<212> TYPE: PRT
<213> ORGANISM: Artificial Sequence
<220> FEATURE:
<223> OTHER INFORMATION: functional heavy chain antibody, functional -continued single domain heavy chain antibody, functional VH domain or
functional fragment thereof comprising this sequence

<400> SEQUENCE: 13

Arg Gly Gln Gly Thr Gln
1               5

<210> SEQ ID NO 14
<211> LENGTH: 6
<212> TYPE: PRT
<213> ORGANISM: Artificial Sequence
<220> FEATURE:
<223> OTHER INFORMATION: functional heavy chain antibody, functional
      single domain heavy chain antibody, functional VH domain or
      functional fragment thereof comprising this sequence

<400> SEQUENCE: 14

Arg Gly Lys Gly Thr Gln
1               5

<210> SEQ ID NO 15
<211> LENGTH: 11
<212> TYPE: PRT
<213> ORGANISM: Artificial Sequence
<220> FEATURE:
<223> OTHER INFORMATION: functional heavy chain antibody, functional
      single domain heavy chain antibody, functional VH domain or
      functional fragment thereof comprising this sequence
<220> FEATURE:
<221> NAME/KEY: MISC_FEATURE
<222> LOCATION: (2)..(7)
<223> OTHER INFORMATION: X is any amino acid
<220> FEATURE:
<221> NAME/KEY: MISC_FEATURE
<222> LOCATION: (10)..(10)
<223> OTHER INFORMATION: X is any amino acid

<400> SEQUENCE: 15

Val Xaa Xaa Xaa Xaa Xaa Xaa Gly Leu Xaa Trp
1               5                   10

<210> SEQ ID NO 16
<211> LENGTH: 11
<212> TYPE: PRT
<213> ORGANISM: Artificial Sequence
<220> FEATURE:
<223> OTHER INFORMATION: functional heavy chain antibody, functional
      single domain heavy chain antibody, functional VH domain or
      functional fragment thereof comprising this sequence

<400> SEQUENCE: 16

Leu Gly Gln Gly Thr Gln Val Thr Val Ser Ser
1               5                   10

<210> SEQ ID NO 17
<211> LENGTH: 11
<212> TYPE: PRT
<213> ORGANISM: Artificial Sequence
<220> FEATURE:
<223> OTHER INFORMATION: functional heavy chain antibody, functional
      single domain heavy chain antibody, functional VH domain or
      functional fragment thereof comprising this sequence

<400> SEQUENCE: 17

Gln Gly Gln Gly Thr Gly Val Thr Val Ser Ser
1               5                   10

<210> SEQ ID NO 18
<211> LENGTH: 11

```
<212> TYPE: PRT
<213> ORGANISM: Artificial Sequence
<220> FEATURE:
<223> OTHER INFORMATION: functional heavy chain antibody, functional
      single domain heavy chain antibody, functional VH domain or
      functional fragment thereof comprising this sequence

<400> SEQUENCE: 18

Pro Gly Gln Gly Thr Gln Val Thr Val Ser Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: functional heavy chain antibody, functional
      single domain heavy chain antibody, functional VH domain or
      functional fragment thereof comprising this sequence

<400> SEQUENCE: 19

Ser Ser Gln Gly Thr Gln Val Thr Val Ser Ser
1               5                   10

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27
```

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

```
<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
```

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<211> LENGTH: 57
<212> TYPE: DNA
<213> ORGANISM: Artificial Sequence
<220> FEATURE:
<223> OTHER INFORMATION: primer 1 (R103)
<220> FEATURE:
<221> NAME/KEY: misc_feature
<222> LOCATION: (55)..(55)
<223> OTHER INFORMATION: n can be A/G/C/T

<400> SEQUENCE: 80
gagtcattct cgacttgcgg ccgctgagga gacggtgacc tgggtcccct ggccncg    57

<210> SEQ ID NO 81
<211> LENGTH: 57
<212> TYPE: DNA
<213> ORGANISM: Artificial Sequence
<220> FEATURE:
<223> OTHER INFORMATION: primer 2 (R103)
<220> FEATURE:
<221> NAME/KEY: misc_feature
<222> LOCATION: (55)..(55)
<223> OTHER INFORMATION: y can be C/T

<400> SEQUENCE: 81
gagtcattct cgacttgcgg ccgctgagga cacggtgacc tgggtcccct ggccyct    57

<210> SEQ ID NO 82
<211> LENGTH: 57
<212> TYPE: DNA
<213> ORGANISM: Artificial Sequence
<220> FEATURE:
<223> OTHER INFORMATION: primer 3 (K103)
<220> FEATURE:
<221> NAME/KEY: misc_feature
<222> LOCATION: (55)..(55)
<223> OTHER INFORMATION: y can be T/C

<400> SEQUENCE: 82
gagtcattct cgacttgcgg ccgcgctgga cacggtgacc tgggtcccct ggccytt    57

<210> SEQ ID NO 83
<211> LENGTH: 57
<212> TYPE: DNA
<213> ORGANISM: Artificial Sequence
<220> FEATURE:
<223> OTHER INFORMATION: primer 4 (Q103)
<220> FEATURE:
<221> NAME/KEY: misc_feature
<222> LOCATION: (55)..(56)
<223> OTHER INFORMATION: s can be C/G; Y can be Y/T

<400> SEQUENCE: 83
gagtcattct cgacttgcgg ccgctgagga cacggtgacc tgggtcccct ggcsytg    57

<210> SEQ ID NO 84
<211> LENGTH: 57
<212> TYPE: DNA
<213> ORGANISM: Artificial Sequence
<220> FEATURE:
<223> OTHER INFORMATION: primer 5 (L103)
<220> FEATURE:
<221> NAME/KEY: misc_feature
<222> LOCATION: (55)..(55)
<223> OTHER INFORMATION: n can be A/G/C/T

<400> SEQUENCE: 84
gagtcattct cgacttgcgg ccgctgagga cacggtgacc tgggtcccct ggccnag    57

<210> SEQ ID NO 85
<211> LENGTH: 57
<212> TYPE: DNA
<213> ORGANISM: Artificial Sequence
<220> FEATURE:
<223> OTHER INFORMATION: primer 6 (F103)
<220> FEATURE:
<221> NAME/KEY: misc_feature
<222> LOCATION: (55)..(55)
<223> OTHER INFORMATION: r can be A/G

<400> SEQUENCE: 85
gagtcattct cgacttgcgg ccgctgagga cacggtgacc tgggtcccct ggccraa    57

<210> SEQ ID NO 86
<211> LENGTH: 57
<212> TYPE: DNA
<213> ORGANISM: Artificial Sequence
<220> FEATURE:
<223> OTHER INFORMATION: primer 7 (G103)
<220> FEATURE:
<221> NAME/KEY: misc_feature
<222> LOCATION: (55)..(55)

```
<223> OTHER INFORMATION: n can be A/G/C/T

<400> SEQUENCE: 86
gagtcattct cgacttgcgg ccgctgagga cacggtgacc tgggtccccc ccggncc        57

<210> SEQ ID NO 87
<211> LENGTH: 57
<212> TYPE: DNA
<213> ORGANISM: Artificial Sequence
<220> FEATURE:
<223> OTHER INFORMATION: primer 8 (S103)
<220> FEATURE:
<221> NAME/KEY: misc_feature
<222> LOCATION: (52)..(52)
<223> OTHER INFORMATION: n can be A/G/C/T
<220> FEATURE:
<221> NAME/KEY: misc_feature
<222> LOCATION: (55)..(55)
<223> OTHER INFORMATION: n can be A/G/C/T

<400> SEQUENCE: 87
gagtcattct cgacttgcgg ccgctgagga cacggtgacc tgggtcccct gnganga        57

<210> SEQ ID NO 88
<211> LENGTH: 57
<212> TYPE: DNA
<213> ORGANISM: Artificial Sequence
<220> FEATURE:
<223> OTHER INFORMATION: primer 9 (P103)
<220> FEATURE:
<221> NAME/KEY: misc_feature
<222> LOCATION: (55)..(55)
<223> OTHER INFORMATION: n can be A/G/C/T

<400> SEQUENCE: 88
gagtcattct cgacttgcgg ccgctgagga cacggtgacc tgggtcccct gctgngg        57

<210> SEQ ID NO 89
<211> LENGTH: 57
<212> TYPE: DNA
<213> ORGANISM: Artificial Sequence
<220> FEATURE:
<223> OTHER INFORMATION: primer 10 (Y103)

<400> SEQUENCE: 89
gagtcattct cgacttgcgg ccgctgagga cacggtgacc tgggtcccct ggccrta        57

<210> SEQ ID NO 90
<211> LENGTH: 345
<212> TYPE: DNA
<213> ORGANISM: Artificial Sequence
<220> FEATURE:
<223> OTHER INFORMATION: mutant TEM04
<220> FEATURE:
<221> NAME/KEY: CDS
<222> LOCATION: (1)..(345)

<400> SEQUENCE: 90 cag gtg cag ctg gtg gag tct ggg gga ggc ttg gtg cag gct gga ggg       48
Gln Val Gln Leu Val Glu Ser Gly Gly Gly Leu Val Gln Ala Gly Gly
1               5                   10                  15 tct ctg agg ctc tcc tgt gca gcc tct gga ttc acc ttc agt agc gca       96
Ser Leu Arg Leu Ser Cys Ala Ala Ser Gly Phe Thr Phe Ser Ser Ala
            20                  25                  30 tgg atg aca tgg gtc cgc cag gct cca ggg aag gga ctc gag tgg gtc      144
Trp Met Thr Trp Val Arg Gln Ala Pro Gly Lys Gly Leu Glu Trp Val
        35                  40                  45
```

```
aca agt att gct acg gat ggg tcc acg gac tat gca gac tcc gtg aag      192
Thr Ser Ile Ala Thr Asp Gly Ser Thr Asp Tyr Ala Asp Ser Val Lys
    50                  55                  60 ggc cga ttc acc atc tcc aga gac aat gcc aag aac acg ctg tat ctg      240
Gly Arg Phe Thr Ile Ser Arg Asp Asn Ala Lys Asn Thr Leu Tyr Leu
65                  70                  75                  80 caa tta aac agc ctg aac act gaa gac acg gcc gtg tat tac tgt gca      288
Gln Leu Asn Ser Leu Asn Thr Glu Asp Thr Ala Val Tyr Tyr Cys Ala
                85                  90                  95 aaa gat cgt tgg ggg tat gtc gta tgg ggc cag ggg acc cag gtc acc      336
Lys Asp Arg Trp Gly Tyr Val Val Trp Gly Gln Gly Thr Gln Val Thr
            100                 105                 110 gtc tcc tca                                                          345
Val Ser Ser
    115

<210> SEQ ID NO 91
<211> LENGTH: 115
<212> TYPE: PRT
<213> ORGANISM: Artificial Sequence
<220> FEATURE:
<223> OTHER INFORMATION: Synthetic Construct

<400> SEQUENCE: 91

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Ser Ala
            20                  25                  30

Trp Met Thr Trp Val Arg Gln Ala Pro Gly Lys Gly Leu Glu Trp Val
        35                  40                  45

Thr Ser Ile Ala Thr Asp Gly Ser Thr Asp Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Asn Thr Glu Asp Thr Ala Val Tyr Tyr Cys Ala
                85                  90                  95

Lys Asp Arg Trp Gly Tyr Val Val Trp Gly Gln Gly Thr Gln Val Thr
            100                 105                 110

Val Ser Ser
    115

<210> SEQ ID NO 92
<211> LENGTH: 351
<212> TYPE: DNA
<213> ORGANISM: Artificial Sequence
<220> FEATURE:
<223> OTHER INFORMATION: anti-carcinoembryonic antigen VHH CEA71, wild
      type
<220> FEATURE:
<221> NAME/KEY: CDS
<222> LOCATION: (1)..(351)

<400> SEQUENCE: 92 cag gtg cag ctg gtg gag tct ggg gga ggc ttg gtg caa cct ggg ggg       48
Gln Val Gln Leu Val Glu Ser Gly Gly Gly Leu Val Gln Pro Gly Gly
1               5                   10                  15 tct ctg aga ctc tcc tgt gca gcc tct gga ttc acc ttc agt agc agc       96
Ser Leu Arg Leu Ser Cys Ala Ala Ser Gly Phe Thr Phe Ser Ser Ser
            20                  25                  30 tac atg agc tgg gtc cgc cag gct cca ggg aag ggg ctg gag tgg gtg      144
Tyr Met Ser Trp Val Arg Gln Ala Pro Gly Lys Gly Leu Glu Trp Val
        35                  40                  45
```

```
tcc ggc att aat acc gat gga agt ttc acg cgc tat gcc gac tcc gtg        192
Ser Gly Ile Asn Thr Asp Gly Ser Phe Thr Arg Tyr Ala Asp Ser Val
        50                  55                  60 aag ggc cga ttc acc atc tcc aga gac aac gcc aag aac acg ctg tat        240
Lys Gly Arg Phe Thr Ile Ser Arg Asp Asn Ala Lys Asn Thr Leu Tyr
65                  70                  75                  80 ctg caa atg aac agc ctg aaa tct gag gac acg gcc ctg tat tac tgt        288
Leu Gln Met Asn Ser Leu Lys Ser Glu Asp Thr Ala Leu Tyr Tyr Cys
                85                  90                  95 gcc gta ggc ggc ggg tta ggc tat ggc ccc agg ggc cag ggg acc ctg        336
Ala Val Gly Gly Gly Leu Gly Tyr Gly Pro Arg Gly Gln Gly Thr Leu
            100                 105                 110 gtc act gtc tcc tca                                                    351
Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic Construct

<400> SEQUENCE: 93

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Tyr Met Ser Trp Val Arg Gln Ala Pro Gly Lys Gly Leu Glu Trp Val
        35                  40                  45

Ser Gly Ile Asn Thr Asp Gly Ser Phe Thr Arg Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Ala Val Gly Gly Gly Leu Gly Tyr Gly Pro Arg Gly Gln Gly Thr Leu
            100                 105                 110

Val Thr Val Ser Ser
        115

<210> SEQ ID NO 94
<211> LENGTH: 351
<212> TYPE: DNA
<213> ORGANISM: Artificial Sequence
<220> FEATURE:
<223> OTHER INFORMATION: CEA71, mutant
<220> FEATURE:
<221> NAME/KEY: CDS
<222> LOCATION: (1)..(351)

<400> SEQUENCE: 94 cag gtg cag ctg gtg gag tct ggg gga ggc ttg gtg caa cct ggg ggg        48
Gln Val Gln Leu Val Glu Ser Gly Gly Gly Leu Val Gln Pro Gly Gly
1               5                   10                  15 tct ctg aga ctc tcc tgt gca gcc tct gga ttc acc ttc agt agc agc        96
Ser Leu Arg Leu Ser Cys Ala Ala Ser Gly Phe Thr Phe Ser Ser Ser
            20                  25                  30 tac atg agc tgg gtc cgc cag gct cca ggg aag ggg ctg gag tgg gtg       144
Tyr Met Ser Trp Val Arg Gln Ala Pro Gly Lys Gly Leu Glu Trp Val
        35                  40                  45
```

```
tcc ggc att aat acc gat gga agt ttc acg cgc tat gcc gac tcc gtg      192
Ser Gly Ile Asn Thr Asp Gly Ser Phe Thr Arg Tyr Ala Asp Ser Val
    50                  55                  60 aag ggc cga ttc acc atc tcc aga gac aac gcc aag aac acg ctg tat      240
Lys Gly Arg Phe Thr Ile Ser Arg Asp Asn Ala Lys Asn Thr Leu Tyr
65                  70                  75                  80 ctg caa atg aac agc ctg aaa tct gag gac acg gcc ctg tat tac tgt      288
Leu Gln Met Asn Ser Leu Lys Ser Glu Asp Thr Ala Leu Tyr Tyr Cys
                85                  90                  95 gcc gta ggc ggc ggg tta ggc tat ggc ccc tgg ggc cag ggg acc ctg      336
Ala Val Gly Gly Gly Leu Gly Tyr Gly Pro Trp Gly Gln Gly Thr Leu
            100                 105                 110 gtc act gtc tcc tca                                                  351
Val Thr Val Ser Ser
        115

<210> SEQ ID NO 95
<211> LENGTH: 117
<212> TYPE: PRT
<213> ORGANISM: Artificial Sequence
<220> FEATURE:
<223> OTHER INFORMATION: Synthetic Construct

<400> SEQUENCE: 95

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Tyr Met Ser Trp Val Arg Gln Ala Pro Gly Lys Gly Leu Glu Trp Val
        35                  40                  45

Ser Gly Ile Asn Thr Asp Gly Ser Phe Thr Arg Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Ala Val Gly Gly Gly Leu Gly Tyr Gly Pro Trp Gly Gln Gly Thr Leu
            100                 105                 110

Val Thr Val Ser Ser
        115

<210> SEQ ID NO 96
<211> LENGTH: 36
<212> TYPE: DNA
<213> ORGANISM: Artificial Sequence
<220> FEATURE:
<223> OTHER INFORMATION: primer A4short-TEM04

<400> SEQUENCE: 96
ggagacggtg acctgggtcc cctggcccca tacgac                              36

<210> SEQ ID NO 97
<211> LENGTH: 35
<212> TYPE: DNA
<213> ORGANISM: Artificial Sequence
<220> FEATURE:
<223> OTHER INFORMATION: primer A4short-CEAVH

<400> SEQUENCE: 97
ggagacggtg acctgggtcc cctggcccca ggggc                               35
```

-continued

<210> SEQ ID NO 98
<211> LENGTH: 22
<212> TYPE: DNA
<213> ORGANISM: Artificial Sequence
<220> FEATURE:
<223> OTHER INFORMATION: primer Call001

<400> SEQUENCE: 98
gtcctggctg ctcttctaca ag					22

<210> SEQ ID NO 99
<211> LENGTH: 23
<212> TYPE: DNA
<213> ORGANISM: Artificial Sequence
<220> FEATURE:
<223> OTHER INFORMATION: primer Call002

<400> SEQUENCE: 99
ggtacgtgct gttgaactgt tcc					23

<210> SEQ ID NO 100
<211> LENGTH: 39
<212> TYPE: DNA
<213> ORGANISM: Artificial Sequence
<220> FEATURE:
<223> OTHER INFORMATION: primer SM018

<400> SEQUENCE: 100
ccagccggcc atggctcagg tgcagctggt ggagtctgg					39

<210> SEQ ID NO 101
<211> LENGTH: 39
<212> TYPE: DNA
<213> ORGANISM: Artificial Sequence
<220> FEATURE:
<223> OTHER INFORMATION: primer SM017

<400> SEQUENCE: 101
ccagccggcc atggctgatg tgcagctggt ggagtctgg					39

<210> SEQ ID NO 102
<211> LENGTH: 33
<212> TYPE: DNA
<213> ORGANISM: Artificial Sequence
<220> FEATURE:
<223> OTHER INFORMATION: A4short primer

<400> SEQUENCE: 102
catgccatga ctcgcggccc agccggccat ggc					33

<210> SEQ ID NO 103
<211> LENGTH: 116
<212> TYPE: PRT
<213> ORGANISM: Camelus dromedarius
<220> FEATURE:
<221> NAME/KEY: MISC_FEATURE
<223> OTHER INFORMATION: N3-A

<400> SEQUENCE: 103

Asp Val Gln Leu Gln Glu Ser Gly Gly Ser Leu Val Gln Pro Gly Gly
1               5                   10                  15

Ser Leu Arg Leu Ser Cys Ala Ala Ser Gly Phe Thr Phe Ser Ala Tyr
            20                  25                  30

Tyr Met Ile Trp Val Arg Gln Ala Pro Gly Lys Gly Leu Glu Trp Val
        35                  40                  45

```
Ser Gly Ile Ser Ala Asn Gly Arg Asp Thr Leu Tyr Glu Asp Ser Val
        50                  55                  60

Glu Gly Arg Phe Ala Ile Ser Arg Asp Asn Ala Lys Asn Thr Leu Tyr
 65                  70                  75                  80

Leu Gln Met Asn Ser Leu Arg Ser Glu Asp Thr Ala Leu Tyr Tyr Cys
                85                  90                  95

Val Ile Gly Ala Leu Ile Thr Gly Arg Arg Gly Gln Gly Thr Gln Val
            100                 105                 110

Thr Val Ser Ser
            115

<210> SEQ ID NO 104
<211> LENGTH: 117
<212> TYPE: PRT
<213> ORGANISM: Camelus dromedarius
<220> FEATURE:
<221> NAME/KEY: MISC_FEATURE
<223> OTHER INFORMATION: N8-B

<400> SEQUENCE: 104

Asp Val Gln Leu Gln Glu Ser Gly Gly Gly Leu Val Gln Pro Gly Gly
 1               5                  10                  15

Ser Leu Arg Leu Ser Cys Ala Ala Ser Gly Phe Leu Phe Ser Asp Thr
            20                  25                  30

Tyr Met Thr Trp Ala Arg Gln Ala Pro Gly Lys Gly Leu Glu Trp Leu
        35                  40                  45

Gly Gly Ile Ser Lys Asp Gly Ser Gly Thr Leu Tyr Glu Asp Ser Val
    50                  55                  60

Glu Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Leu Tyr Tyr Cys
                85                  90                  95

Ser Thr Gly Ala Leu Leu Pro Thr Arg Pro Gly Gln Gly Thr Gln
            100                 105                 110

Val Thr Val Ser Ser
            115

<210> SEQ ID NO 105
<211> LENGTH: 120
<212> TYPE: PRT
<213> ORGANISM: Camelus dromedarius
<220> FEATURE:
<221> NAME/KEY: MISC_FEATURE
<223> OTHER INFORMATION: C9-B

<400> SEQUENCE: 105

Asp Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
            20                  25                  30

Tyr Met Thr Trp Val Arg Gln Ala Pro Gly Lys Gly Leu Glu Trp Val
        35                  40                  45

Ser Val Ile Ser Asn Asp Gly Arg Tyr Thr Asp Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Thr Glu Asp Thr Ala Leu Tyr Thr Cys
                85                  90                  95
```

Val Arg Gly Tyr Tyr Leu Thr Asn Leu Pro Ala Gly Asp Arg Gly Gln
            100                 105                 110

Gly Thr Gln Val Thr Val Ser Ser
        115                 120

<210> SEQ ID NO 106
<211> LENGTH: 116
<212> TYPE: PRT
<213> ORGANISM: Camelus dromedarius
<220> FEATURE:
<221> NAME/KEY: MISC_FEATURE
<223> OTHER INFORMATION: C11-B

<400> SEQUENCE: 106

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Ile Phe Ser Asn Thr
            20                  25                  30

Tyr Met Thr Trp Val Arg Gln Ala Pro Gly Lys Gly Leu Glu Trp Val
        35                  40                  45

Ser Gly Ile Ser Ala Asp Gly Arg Asp Thr Leu Tyr Ala Asp Ser Val
    50                  55                  60

Glu Gly Arg Phe Ala Ile Ser Arg Asp Asn Ala Lys Asn Thr Leu Tyr
65                  70                  75                  80

Leu Gln Met Asn Ser Leu Arg Ser Glu Asp Thr Ala Leu Tyr Tyr Cys
                85                  90                  95

Val Thr Gly Ala Leu Met Thr Gly Arg Arg Gly Gln Gly Thr Gln Val
            100                 105                 110

Thr Val Ser Ser
        115

<210> SEQ ID NO 107
<211> LENGTH: 117
<212> TYPE: PRT
<213> ORGANISM: Camelus dromedarius
<220> FEATURE:
<221> NAME/KEY: MISC_FEATURE
<223> OTHER INFORMATION: C12-A

<400> SEQUENCE: 107

Asp Val Gln Leu Gln Glu Ser Gly Gly Gly Leu Val Arg Pro Gly Gly
1               5                   10                  15

Ser Leu Arg Leu Ser Cys Ala Ala Ser Gly Phe Leu Phe Ser Gly Thr
            20                  25                  30

Tyr Met Thr Trp Ala Arg Gln Ala Pro Gly Lys Gly Leu Glu Trp Leu
        35                  40                  45

Cys Gly Ile Asn Lys Asp Gly Ser Gly Thr Leu Tyr Ala Asp Ser Val
    50                  55                  60

Glu Gly Arg Phe Thr Cys Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Ser Thr Gly Ala Leu Leu Pro Thr Arg Pro Gln Gly Gln Gly Thr Gln
            100                 105                 110

Val Thr Val Ser Ser
        115

<210> SEQ ID NO 108

```
<211> LENGTH: 116
<212> TYPE: PRT
<213> ORGANISM: Camelus dromedarius
<220> FEATURE:
<221> NAME/KEY: MISC_FEATURE
<223> OTHER INFORMATION: C1-B

<400> SEQUENCE: 108

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ser
            20                  25                  30

Tyr Met Thr Trp Ala Arg Gln Ala Pro Gly Lys Gly Leu Glu Trp Val
        35                  40                  45

Ser Gly Ile Asn Arg Asp Gly Asn Asn Pro Leu Tyr Ala Asp Ser Val
    50                  55                  60

Glu Gly Arg Phe Thr Val Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Val Ala Gly Ala Leu Val Ala Gly Ala Arg Gly Gln Gly Thr Gln Val
            100                 105                 110

Thr Val Ser Ser
        115

<210> SEQ ID NO 109
<211> LENGTH: 120
<212> TYPE: PRT
<213> ORGANISM: Camelus dromedarius
<220> FEATURE:
<221> NAME/KEY: MISC_FEATURE
<223> OTHER INFORMATION: C24-A

<400> SEQUENCE: 109

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Thr Pro Ser
            20                  25                  30

Tyr Met Ser Trp Val Arg Gln Ala Pro Gly Lys Gly Leu Glu Trp Val
        35                  40                  45

Ser Val Ile Ser Asn Asp Gly Arg Tyr Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Leu Tyr Thr Cys
                85                  90                  95

Val Arg Gly Tyr Tyr Leu Thr Asn Leu Pro Ala Gly Asp Arg Gly Gln
            100                 105                 110

Gly Thr Gln Val Thr Val Ser Ser
        115                 120

<210> SEQ ID NO 110
<211> LENGTH: 118
<212> TYPE: PRT
<213> ORGANISM: Camelus dromedarius
<220> FEATURE:
<221> NAME/KEY: MISC_FEATURE
<223> OTHER INFORMATION: N13-A

<400> SEQUENCE: 110
```

Asp Val Gln Leu Gln Glu Ser Gly Gly Gly Ser Val Gln Pro Gly Gly
1               5                   10                  15

Ser Leu Arg Leu Ser Cys Ala Ala Ser Gly Phe Thr Phe Lys Asp Ala
            20                  25                  30

Ser Met Asn Trp Val Arg Gln Ala Pro Gly Lys Gly Leu Glu Trp Val
        35                  40                  45

Ser Ala Ile Asn Gly Gly Thr Val Thr Asp Tyr Ala Asp Pro Met
    50                  55                  60

Glu Gly Arg Phe Thr Ile Ser Arg Asp Asn Ala Lys Asn Thr Leu Tyr
65                  70                  75                  80

Leu Gln Met Asn Ser Leu Asn Phe Glu Asp Thr Ala Leu Tyr Tyr Cys
                85                  90                  95

Ala Thr Gly Trp Leu Phe Arg Ala Asn Asn Tyr Arg Gly Gln Gly Thr
            100                 105                 110

Gln Val Thr Val Ser Ser
        115

<210> SEQ ID NO 111
<211> LENGTH: 121
<212> TYPE: PRT
<213> ORGANISM: Camelus dromedarius
<220> FEATURE:
<221> NAME/KEY: MISC_FEATURE
<223> OTHER INFORMATION: N15-B

<400> SEQUENCE: 111

Asp Val Gln Leu Gln Glu Ser Gly Gly Gly Ser Val Gln Ala Gly Gly
1               5                   10                  15

Ser Leu Arg Leu Ala Cys Ala Ala Thr Ala Tyr Thr Tyr Asp Ser Asn
            20                  25                  30

Val Leu Gly Trp Phe Arg Gln Ala Pro Gly Lys Glu His Glu Gly Val
        35                  40                  45

Ala Val Ile Tyr Thr Gly Thr Arg Thr Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Gly Asp Thr Ala Met Tyr Phe Cys
                85                  90                  95

Ala Ala Asn Val Arg Leu Gly Val Trp Ser Phe Asp Tyr Arg Gly
            100                 105                 110

Gln Gly Thr Gln Val Thr Val Ser Ser
        115                 120

<210> SEQ ID NO 112
<211> LENGTH: 118
<212> TYPE: PRT
<213> ORGANISM: Lama glama
<220> FEATURE:
<221> NAME/KEY: MISC_FEATURE
<223> OTHER INFORMATION: ALB-1

<400> SEQUENCE: 112

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Ser Ser Phe
            20                  25                  30

Pro Met Thr Trp Val Arg Gln Ala Pro Gly Lys Gly Leu Glu Trp Val
        35                  40                  45

Ser Gly Ile Leu Glu Gly Gly Ser Pro Ala Tyr Ala Asp Ser Val
            50                  55                  60

Lys Gly Arg Phe Thr Ile Ser Arg Asp Asp Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Gly Tyr Val Tyr Ala Arg Glu Gly Ala Arg Ser Gln Gly Thr
            100                 105                 110

Gln Val Thr Val Ser Ser
            115

<210> SEQ ID NO 113
<211> LENGTH: 114
<212> TYPE: PRT
<213> ORGANISM: Lama glama
<220> FEATURE:
<221> NAME/KEY: MISC_FEATURE
<223> OTHER INFORMATION: ALB-2

<400> SEQUENCE: 113

Gln Val Gln Leu Gln Glu Ser Gly Gly Gly Leu Val Gln Pro Gly Gly
  1               5                  10                  15

Ser Leu Arg Leu Thr Cys Thr Ala Ser Gly Phe Ala Phe Ser Asn Phe
             20                  25                  30

Gly Met Ser Trp Val Arg Gln Pro Pro Gly Lys Gly Leu Glu Trp Val
         35                  40                  45

Ser Ala Ile Ser Ala Asp Ser Ser Thr Lys Asn Tyr Ala Asp Ser Val
     50                  55                  60

Lys Gly Arg Phe Thr Ile Ser Arg Asp Asn Thr Lys Lys Met Leu Tyr
 65                  70                  75                  80

Leu Glu Met Asn Ser Leu Lys Pro Glu Asp Thr Ala Val Tyr His Cys
                 85                  90                  95

Val Ile Gly Arg Gly Ser Ala Ser Ser Gln Gly Thr Gln Val Thr Val
            100                 105                 110

Ser Ser

<210> SEQ ID NO 114
<211> LENGTH: 115
<212> TYPE: PRT
<213> ORGANISM: Lama glama
<220> FEATURE:
<221> NAME/KEY: MISC_FEATURE
<223> OTHER INFORMATION: ALB-3

<400> SEQUENCE: 114

Gln Val Gln Leu Gln Glu Ser Gly Gly Gly Leu Val Gln Pro Gly Asn
  1               5                  10                  15

Ser Leu Arg Leu Ser Cys Ala Ala Ser Gly Phe Ala Phe Gly Asn Phe
             20                  25                  30

Gly Met Ser Trp Val Arg Gln Ala Pro Gly Lys Glu Pro Glu Trp Val
         35                  40                  45

Ser Ser Ile Asp Ser Ile Gly Ser Asp Thr Leu Tyr Ala Asp Phe Val
     50                  55                  60

Lys Gly Arg Phe Thr Ile Ser Arg Asp Asn Ala Lys Ser Thr Leu Tyr
 65                  70                  75                  80

Leu Gln Met Asn Ser Leu Lys Pro Glu Asp Thr Ala Val Tyr Tyr Cys
                 85                  90                  95

Thr Ile Gly Gly Ser Leu Ser Arg Ser Ser Gln Gly Thr Gln Val Thr

Val Ser Ser
        115

<210> SEQ ID NO 115
<211> LENGTH: 115
<212> TYPE: PRT
<213> ORGANISM: Lama glama
<220> FEATURE:
<221> NAME/KEY: MISC_FEATURE
<223> OTHER INFORMATION: ALB-4

<400> SEQUENCE: 115

Gln Val Gln Leu Gln Glu Ser Gly Gly Gly Leu Val Gln Pro Gly Asn
1               5                   10                  15

Ser Leu Arg Leu Ser Cys Ala Ala Ser Gly Phe Ser Phe Arg Ser Phe
            20                  25                  30

Gly Met Ser Trp Val Arg Gln Ala Pro Gly Lys Gly Pro Glu Trp Val
        35                  40                  45

Ser Ser Ile Asn Ser Ser Gly Asp Asp Thr Arg Tyr Thr Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Ser Ser Ile Ser Arg Ser Ser Gln Gly Thr Gln Val Thr
            100                 105                 110

Val Ser Ser
        115

<210> SEQ ID NO 116
<211> LENGTH: 114
<212> TYPE: PRT
<213> ORGANISM: Lama glama
<220> FEATURE:
<221> NAME/KEY: MISC_FEATURE
<223> OTHER INFORMATION: ALB-5

<400> SEQUENCE: 116

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Ala Phe Ser Ser Phe
            20                  25                  30

Gly Met Ser Trp Val Arg Gln Pro Pro Gly Lys Gly Leu Glu Trp Val
        35                  40                  45

Ser Ala Ile Ser Ala Asp Ser Ser Thr Lys Asn Tyr Ala Asp Ser Val
    50                  55                  60

Lys Gly Arg Phe Thr Ile Ser Arg Asp Asn Asp Lys Lys Met Leu Tyr
65                  70                  75                  80

Leu Glu Met Asn Lys Leu Lys Pro Glu Asp Thr Ala Val Tyr His Cys
                85                  90                  95

Val Ile Gly Arg Gly Ser Pro Ser Ser Gln Gly Thr Gln Val Thr Val
            100                 105                 110

Ser Ser

<210> SEQ ID NO 117
<211> LENGTH: 120
<212> TYPE: PRT
<213> ORGANISM: Camelus dromedarius

```
<220> FEATURE:
<221> NAME/KEY: MISC_FEATURE
<223> OTHER INFORMATION: CEA1

<400> SEQUENCE: 117

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asp Met Ser Trp Val Arg Gln Ala Pro Gly Lys Gly Leu Glu Trp Val
        35                  40                  45

Ser Arg Ile Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65              70                  75                  80

Leu Gln Met Asn Ser Leu Lys Pro Glu Asp Thr Ala Val Tyr Tyr Cys
                85                  90                  95

Ala Thr Pro Thr Tyr Ser Ser Asp Tyr Arg Gly Leu Pro Pro Gly Gln
            100                 105                 110

Gly Thr Gln Val Thr Val Ser Ser
        115                 120

<210> SEQ ID NO 118
<211> LENGTH: 117
<212> TYPE: PRT
<213> ORGANISM: Camelus dromedarius
<220> FEATURE:
<221> NAME/KEY: MISC_FEATURE
<223> OTHER INFORMATION: CEA72

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Ser Ser
            20                  25                  30

Tyr Met Ser Trp Val Arg Gln Ala Pro Gly Lys Gly Leu Glu Trp Val
        35                  40                  45

Ser Gly Ile Asn Thr Asp Gly Ser Phe Thr Arg Tyr Ala Asp Ser Val
    50                  55                  60

Lys Gly Arg Phe Thr Ile Ser Arg Asp Asn Ala Lys Asn Thr Leu Tyr
65              70                  75                  80

Leu Gln Met Asn Ser Leu Lys Ser Glu Asp Thr Ala Leu Tyr Tyr Cys
                85                  90                  95

Ala Val Gly Gly Gly Leu Gly Tyr Gly Pro Arg Gly Gln Gly Thr Gln
            100                 105                 110

Val Thr Val Ser Ser
        115

<210> SEQ ID NO 119
<211> LENGTH: 118
<212> TYPE: PRT
<213> ORGANISM: Camelus dromedarius
<220> FEATURE:
<221> NAME/KEY: MISC_FEATURE
<223> OTHER INFORMATION: B13

<400> SEQUENCE: 119

Gln Val Gln Leu Gln Ala Ser Gly Gly Gly Leu Val Gln Pro Gly Gly
1               5                   10                  15
```

Ser Leu Arg Leu Ser Cys Ala Ala Ser Gly Phe Asp Phe Met Asn Val
            20                  25                  30

Tyr Met Thr Trp Val Arg Gln Ala Pro Gly Lys Gly Val Glu Trp Val
        35                  40                  45

Ser Gly Ile Ser Val Ser Gly Ser Ile Thr His Tyr Ser Glu Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Lys Ser Glu Asp Thr Ala Arg Tyr Tyr Cys
                85                  90                  95

Ala Arg Gly Gly Tyr Asn Arg Tyr Tyr Gly Ala Leu Gly Gln Gly Thr
            100                 105                 110

Leu Val Thr Val Ser Ser
            115

<210> SEQ ID NO 120
<211> LENGTH: 100
<212> TYPE: PRT
<213> ORGANISM: Camelus dromedarius
<220> FEATURE:
<221> NAME/KEY: MISC_FEATURE
<223> OTHER INFORMATION: 1DBOVA11
<220> FEATURE:
<221> NAME/KEY: MISC_FEATURE
<222> LOCATION: (14)..(14)
<223> OTHER INFORMATION: X can be any amino acid
<220> FEATURE:
<221> NAME/KEY: MISC_FEATURE
<222> LOCATION: (32)..(32)
<223> OTHER INFORMATION: X can be any amino acid
<220> FEATURE:
<221> NAME/KEY: MISC_FEATURE
<222> LOCATION: (57)..(57)
<223> OTHER INFORMATION: X can be any amino acid
<220> FEATURE:
<221> NAME/KEY: MISC_FEATURE
<222> LOCATION: (62)..(63)
<223> OTHER INFORMATION: X can be any amino acid
<220> FEATURE:
<221> NAME/KEY: MISC_FEATURE
<222> LOCATION: (87)..(88)
<223> OTHER INFORMATION: X can be any amino acid

<400> SEQUENCE: 120

Gln Val Gln Leu Val Glu Ser Gly Gly Gly Ser Val Gln Xaa Gly Glu
1               5                   10                  15

Ser Leu Arg Leu Ser Cys Val Ala Ser Gly Phe Thr Phe Asp Val Xaa
            20                  25                  30

Tyr Met Asn Trp Val Arg Gln Ala Pro Gly Lys Gly Leu Glu Trp Val
        35                  40                  45

Ser Gly Ile Ser Ala Ser Gly Tyr Xaa Thr Thr Tyr Ala Xaa Xaa Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Xaa Xaa Thr Arg Gly Gln Gly Thr Gln Val
                85                  90                  95

Thr Val Ser Ser
            100

<210> SEQ ID NO 121
<211> LENGTH: 118
<212> TYPE: PRT
<213> ORGANISM: Camelus dromedarius
<220> FEATURE:

<221> NAME/KEY: MISC_FEATURE
<223> OTHER INFORMATION: 1DBOVA23

<400> SEQUENCE: 121

Gln Val Gln Leu Val Glu Ser Gly Gly Gly Ser Val Gln Ala Gly Gly
1               5                   10                  15

Ser Leu Ile Ile Ser Cys Ala Ala Ser Gly Phe Asp Phe Asn Asn
            20                  25                  30

Tyr Met Thr Trp Val Arg Gln Ala Pro Gly Lys Gly Val Glu Trp Val
            35                  40                  45

Ser Gly Ile Ser Val Ser Gly Ser Ile Thr His Tyr Thr Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Arg Tyr Tyr Cys
                85                  90                  95

Gly Thr Gly Gly Tyr Gly Arg Tyr Tyr Gly Thr Leu Gly Gln Gly Thr
            100                 105                 110

Gln Val Thr Val Ser Ser
            115

<210> SEQ ID NO 122
<211> LENGTH: 121
<212> TYPE: PRT
<213> ORGANISM: Camelus dromedarius
<220> FEATURE:
<221> NAME/KEY: MISC_FEATURE
<223> OTHER INFORMATION: 1DBOVA43

<400> SEQUENCE: 122

Gln Val Gln Leu Val Glu Ser Gly Gly Gly Leu Val Gln Pro Gly Gly
1               5                   10                  15

Ser Leu Arg Leu Ser Cys Val Gly Ser Gly Phe Thr Phe Ser Ser Tyr
            20                  25                  30

Tyr Ile Ser Trp Val Arg Gln Ala Pro Gly Lys Gly Leu Glu Trp Val
            35                  40                  45

Ser Gly Ile Ser Gly Ser Gly Ala Thr Thr Ser Tyr Thr Asp Ser Val
        50                  55                  60

Lys Gly Arg Phe Thr Ile Ser Arg Asp Asn Ala Lys Asn Thr Val Tyr
65                  70                  75                  80

Leu Gln Leu Asn Ser Leu Glu Thr Glu Asp Ser Ala Met Tyr Tyr Cys
                85                  90                  95

Arg Leu Gly Tyr Gly Thr Pro Pro Gly Val Trp Pro Ser Gln Arg
            100                 105                 110

Gln Gly Thr Gln Val Thr Val Ser Ser
            115                 120

<210> SEQ ID NO 123
<211> LENGTH: 114
<212> TYPE: PRT
<213> ORGANISM: Camelus dromedarius
<220> FEATURE:
<221> NAME/KEY: MISC_FEATURE
<223> OTHER INFORMATION: A2-19

<400> SEQUENCE: 123

Gln Val Gln Leu Gln Ala Ser Gly Gly Gly Leu Val Gln Pro Gly Gly
1               5                   10                  15

Ser Leu Lys Leu Ser Cys Val Val Ser Gly Phe Leu Phe Ser Asn Tyr

```
                20                  25                  30
Ala Phe Ser Trp Val Arg Gln Ala Pro Gly Lys Gly Leu Glu Trp Val
            35                  40                  45

Ser Thr Ile Gly Thr Ser Ser Gly Tyr Thr Asn Tyr Ala Pro Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Thr Glu Asp Thr Ala Met Tyr Tyr Cys
                85                  90                  95

Arg Arg Pro Gly Thr Asp Glu Arg Gly Gln Gly Thr Gln Val Thr Val
            100                 105                 110

Ser Ser

<210> SEQ ID NO 124
<211> LENGTH: 118
<212> TYPE: PRT
<213> ORGANISM: Camelus dromedarius
<220> FEATURE:
<221> NAME/KEY: MISC_FEATURE
<223> OTHER INFORMATION: A4-17

<400> SEQUENCE: 124

Gln Val Gln Leu Gln Ala Ser Gly Gly Gly Leu Val Gln Pro Gly Gly
1               5                   10                  15

Ser Leu Arg Leu Ser Cys Ala Ala Ser Gly Phe Asp Phe Ser Asn Val
            20                  25                  30

Tyr Met Thr Trp Val Arg Gln Ala Pro Gly Lys Gly Val Glu Trp Val
            35                  40                  45

Ser Gly Ile Ser Val Ser Gly Ser Ile Thr His Tyr Ser Asp Ser Val
    50                  55                  60

Lys Asp Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Arg Tyr Tyr Cys
                85                  90                  95

Ala Arg Gly Gly Tyr Asn Thr Tyr Ser Gly Ala Leu Gly Gln Gly Thr
            100                 105                 110

Gln Val Thr Val Ser Ser
        115

<210> SEQ ID NO 125
<211> LENGTH: 126
<212> TYPE: PRT
<213> ORGANISM: Camelus dromedarius
<220> FEATURE:
<221> NAME/KEY: MISC_FEATURE
<223> OTHER INFORMATION: B368

<400> SEQUENCE: 125

Val Gln Leu Val Glu Ser Gly Gly Gly Ser Val Gln Ala Gly Gly Ser
1               5                   10                  15

Leu Ile Leu Ser Cys Thr Ala Ser Gly Leu Pro Tyr Lys Ser Tyr Cys
            20                  25                  30

Met Gly Trp Phe Arg Gln Ala Ala Gly Lys Glu Pro Glu Gly Val Ala
            35                  40                  45

Thr Ile Asn Ser Gly Thr Gly Ser Lys Phe Tyr Thr Asp Ser Val Lys
    50                  55                  60

Gly Arg Phe Thr Ile Ser Leu Asp Asn Asp Asn Asn Arg Val Tyr Leu
65                  70                  75                  80
```

Glu Met Ser Ser Leu Lys Pro Glu Asp Thr Ala Thr Tyr Tyr Cys Ala
                85                  90                  95

Ala Gly Gln Arg His Ser Cys Gly Tyr Val Leu Lys Asn Thr Asp Gly
            100                 105                 110

Trp Thr His Arg Ala Gln Gly Thr Gln Val Thr Val Ser Ser
        115                 120                 125

<210> SEQ ID NO 126
<211> LENGTH: 116
<212> TYPE: PRT
<213> ORGANISM: Camelus dromedarius
<220> FEATURE:
<221> NAME/KEY: MISC_FEATURE
<223> OTHER INFORMATION: R24

<400> SEQUENCE: 126

Ser Ala Gln Val Gln Leu Gln Ala Ser Gly Gly Leu Val Gln Pro
1               5                   10                  15

Gly Gly Ser Leu Lys Leu Ser Cys Val Val Ser Gly Phe Leu Phe Ser
            20                  25                  30

Asn Tyr Ala Phe Ser Trp Val Arg Gln Ala Pro Gly Lys Gly Leu Glu
        35                  40                  45

Trp Val Ser Thr Ile Gly Thr Ser Ser Gly Tyr Thr Asn Tyr Ala Pro
    50                  55                  60

Ser Val Lys Gly Arg Phe Thr Ile Ser Arg Asp Asn Ala Lys Asn Thr
65                  70                  75                  80

Val Tyr Leu Gln Leu Asn Ser Leu Lys Thr Glu Asp Thr Ala Met Tyr
                85                  90                  95

Tyr Cys Arg Arg Pro Gly Thr Asp Glu Arg Gly Gln Gly Thr Gln Val
            100                 105                 110

Thr Val Ser Ser
        115

<210> SEQ ID NO 127
<211> LENGTH: 121
<212> TYPE: PRT
<213> ORGANISM: Camelus dromedarius
<220> FEATURE:
<221> NAME/KEY: MISC_FEATURE
<223> OTHER INFORMATION: cAbAn04

<400> SEQUENCE: 127

Gln Val Gln Leu Val Glu Ser Gly Gly Gly Ser Val Glu Ala Gly Gly
1               5                   10                  15

Ser Leu Arg Leu Ser Cys Val Val Ser Gly Tyr Ser Val Ser Ile Gly
            20                  25                  30

Cys Met Ala Trp Phe Arg Gln Ala Pro Gly Ser Gly Glu Gly Val
        35                  40                  45

Ala Gly Ile Ser Arg Gly Gly Ser Met Thr Asp Tyr Thr Ala Ser Val
    50                  55                  60

Lys Gly Arg Phe Thr Ile Ser Arg Asp Asn Asp Gln Arg Thr Val Thr
65                  70                  75                  80

Leu Gln Met Asn Ser Leu Lys Pro Glu Asp Thr Ala Val Tyr Tyr Cys
                85                  90                  95

Ala Arg Asp Gly Pro Glu Ile Ala Thr Met Ile Gly Gly Ser Arg Gly
            100                 105                 110

Arg Gly Thr Gln Val Thr Val Ser Ser
        115                 120

<210> SEQ ID NO 128
<211> LENGTH: 131
<212> TYPE: PRT
<213> ORGANISM: Camelus dromedarius
<220> FEATURE:
<221> NAME/KEY: MISC_FEATURE
<223> OTHER INFORMATION: cAbBLA01

<400> SEQUENCE: 128

Gln Leu Gln Leu Val Glu Ser Gly Gly Gly Ser Val Gln Ser Gly Gly
1               5                   10                  15

Ser Leu Arg Leu Ser Cys Lys Val Ser Gly Tyr Ile Gly Ser Thr Asn
            20                  25                  30

Cys Met Gly Trp Phe Arg Gln Ala Pro Gly Lys Glu Arg Glu Gly Val
        35                  40                  45

Ala Ser Leu Phe Thr Gly Ser Gly Asn Thr Tyr Tyr Gly Asp Ser Val
    50                  55                  60

Lys Gly Arg Phe Thr Ile Ser Glu Asp Asn Ala Lys Asn Thr Val Ser
65                  70                  75                  80

Leu Gln Met Asn Ser Leu Lys Pro Glu Asp Thr Ala Met Tyr Tyr Cys
                85                  90                  95

Ala Ser Ser Ser Asn Val Gly Ser Asp Glu Ser Cys Gly Arg Lys Asn
            100                 105                 110

Thr Arg Gln Phe Val Tyr Thr Tyr Gln Gly Gln Gly Thr Gln Val Thr
        115                 120                 125

Val Ser Ser
    130

<210> SEQ ID NO 129
<211> LENGTH: 115
<212> TYPE: PRT
<213> ORGANISM: Camelus dromedarius
<220> FEATURE:
<221> NAME/KEY: MISC_FEATURE
<223> OTHER INFORMATION: cAbTEM04

<400> SEQUENCE: 129

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Ser Ala
            20                  25                  30

Trp Met Thr Trp Val Arg Gln Ala Pro Gly Lys Gly Leu Glu Trp Val
        35                  40                  45

Thr Ser Ile Ala Thr Asp Gly Ser Thr Asp Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Asn Thr Glu Asp Thr Ala Val Tyr Tyr Cys Ala
                85                  90                  95

Lys Asp Arg Trp Gly Tyr Val Val Arg Gly Gln Gly Thr Gln Val Thr
            100                 105                 110

Val Ser Ser
    115

<210> SEQ ID NO 130
<211> LENGTH: 126
<212> TYPE: PRT
<213> ORGANISM: Camelus dromedarius

<220> FEATURE:
<221> NAME/KEY: MISC_FEATURE
<223> OTHER INFORMATION: 1D2CA30

<400> SEQUENCE: 130

Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Val Ser Thr Tyr
            20                  25                  30

Cys Met Gly Trp Phe Arg Gln Ala Pro Gly Lys Glu Arg Glu Gly Val
        35                  40                  45

Ala Thr Ile Leu Gly Gly Ser Thr Tyr Tyr Gly Asp Ser Val Lys Gly
    50                  55                  60

Arg Phe Thr Ile Ser Gln Asp Asn Ala Lys Asn Thr Val Tyr Leu Gln
65                  70                  75                  80

Met Asn Ser Leu Lys Pro Glu Asp Thr Ala Ile Tyr Tyr Cys Ala Gly
                85                  90                  95

Ser Thr Val Ala Ser Thr Gly Trp Cys Ser Arg Leu Arg Pro Tyr Asp
            100                 105                 110

Tyr His Tyr Arg Gly Gln Gly Thr Gln Val Thr Val Ser Ser
        115                 120                 125

<210> SEQ ID NO 131
<211> LENGTH: 115
<212> TYPE: PRT
<213> ORGANISM: Lama glama
<220> FEATURE:
<221> NAME/KEY: MISC_FEATURE
<223> OTHER INFORMATION: C4 PABP2

<400> SEQUENCE: 131

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Arg Ser
            20                  25                  30

Trp Met Tyr Trp Val Arg Gln Ala Pro Gly Lys Gly Leu Glu Trp Val
        35                  40                  45

Ser Ser Ile Thr Pro Gly Gly Ser Glu Pro Phe Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Phe Cys
                85                  90                  95

Ala Lys Asp Ser Lys Asn Gly Pro Arg Gly Gln Gly Thr Gln Val Thr
            100                 105                 110

Val Ser Ser
        115

<210> SEQ ID NO 132
<211> LENGTH: 115
<212> TYPE: PRT
<213> ORGANISM: Lama glama
<220> FEATURE:
<221> NAME/KEY: MISC_FEATURE
<223> OTHER INFORMATION: E3 PABP2

<400> SEQUENCE: 132

Gln Val Gln Leu Gln Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Arg Ser
            20                  25                  30

Trp Met Tyr Trp Val Arg Gln Ala Pro Gly Lys Gly Leu Glu Trp Val
            35                  40                  45

Ser Ser Ile Thr Pro Gly Gly Thr Glu Ala Tyr Ala Asp Ser Val
 50                      55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Leu Tyr Phe Cys
                85                  90                  95

Ala Lys Asp Ser Lys Asn Gly Pro Arg Gly Gln Gly Thr Gln Val Thr
                100                 105                 110

Val Ser Ser
        115

<210> SEQ ID NO 133
<211> LENGTH: 115
<212> TYPE: PRT
<213> ORGANISM: Lama glama
<220> FEATURE:
<221> NAME/KEY: MISC_FEATURE
<223> OTHER INFORMATION: F6 PABP2

<400> SEQUENCE: 133

Gln Val Gln Leu Gln Glu Ser Gly Gly Gly Leu Val Gln Pro Gly Gly
 1               5                   10                  15

Ser Leu Arg Leu Ser Cys Ala Thr Ser Gly Phe Ile Phe Ser Asp Tyr
            20                  25                  30

Trp Met Tyr Trp Val Arg Gln Ala Pro Gly Lys Gly Leu Glu Trp Val
            35                  40                  45

Ser Ser Ile Thr Pro Gly Ala Ser Thr Thr Leu Tyr Ala Asp Ser Val
 50                      55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                85                  90                  95

Ala Lys Gly Ser Lys Ile Gly Pro Arg Gly Gln Gly Thr Gln Val Thr
                100                 105                 110

Val Ser Ser
        115

<210> SEQ ID NO 134
<211> LENGTH: 115
<212> TYPE: PRT
<213> ORGANISM: Lama glama
<220> FEATURE:
<221> NAME/KEY: MISC_FEATURE
<223> OTHER INFORMATION: LA-1

<400> SEQUENCE: 134

Gln Val Gln Leu Gln Asp Asp Ser Gly Gly Gly Leu Val Gln Pro Gly
 1               5                   10                  15

Gly Ser Leu Lys Leu Ser Cys Ala Ala Ser Gly Phe Thr Phe Ser Asn
            20                  25                  30

Tyr Glu Met Ser Trp Val Arg Gln Ala Pro Gly Lys Gly Leu Glu Trp
            35                  40                  45

Val Ser Ser Ile Asn Asn Gly Gly Asp Ile Thr Tyr Tyr Ala Asn Ser
 50                      55                  60
```

-continued

```
Val Lys Gly Arg Phe Thr Ile Ser Arg Asp Asn Thr Lys Asn Thr Leu
 65                  70                  75                  80

Tyr Leu Gln Met Asn Ser Leu Lys Ser Glu Asp Thr Ala Val Tyr Tyr
                 85                  90                  95

Cys Lys Val Pro Asn Arg Arg Leu Arg Gly Pro Gly Thr Gln Val Thr
            100                 105                 110

Val Ser Ser
        115
```

<210> SEQ ID NO 135
<211> LENGTH: 114
<212> TYPE: PRT
<213> ORGANISM: Lama glama
<220> FEATURE:
<221> NAME/KEY: MISC_FEATURE
<223> OTHER INFORMATION: CD40-1

<400> SEQUENCE: 135

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Ser Arg Tyr
            20                  25                  30

Ser Met Tyr Trp Val Arg Gln Ala Pro Gly Lys Gly Leu Glu Trp Val
        35                  40                  45

Ser Glu Ile Tyr Pro Asp Gly Asn Gly Trp Tyr Thr Ser Ser Val Lys
    50                  55                  60

Gly Arg Phe Thr Ile Ser Arg Asp Asn Asp Lys Asn Met Leu Tyr Leu
 65                  70                  75                  80

Gln Met Asn Ser Leu Lys Pro Asp Asp Thr Ala Val Tyr Tyr Cys Ala
                 85                  90                  95

Leu Ser Arg Ser Gly Gly Arg Gly Gln Gly Thr Arg Val Thr Val
            100                 105                 110

Ser Ser
```

<210> SEQ ID NO 136
<211> LENGTH: 111
<212> TYPE: PRT
<213> ORGANISM: Lama glama
<220> FEATURE:
<221> NAME/KEY: MISC_FEATURE
<223> OTHER INFORMATION: CD40-2

<400> SEQUENCE: 136

```
Glu Val Gln Leu Val Glu Ser Gly Gly Gly Leu Val Gln Ala Gly Gly
 1               5                  10                  15

Ser Leu Glu Leu Ser Cys Ser Phe Gly Gly Arg Ala Phe Asp Arg Tyr
            20                  25                  30

Phe Met Ala Trp Phe Arg Gln Ala Pro Gly Lys Gly Leu Glu Trp Val
        35                  40                  45

Ser Arg Ile Tyr Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
 65                  70                  75                  80

Gln Met Asn Asn Leu Lys Pro Glu Asp Thr Ala Val Tyr Tyr Cys Asp
                 85                  90                  95

Ile Ala Gly Arg Arg Gly Gln Gly Ile Gln Val Thr Val Ser Ser
            100                 105                 110
```

```
<210> SEQ ID NO 137
<211> LENGTH: 112
<212> TYPE: PRT
<213> ORGANISM: Lama glama
<220> FEATURE:
<221> NAME/KEY: MISC_FEATURE
<223> OTHER INFORMATION: CD40-3

<400> SEQUENCE: 137
```

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Asn Thr Val
            20                  25                  30

Asp Met Gly Trp Phe Arg Gln Ala Pro Gly Lys Glu Arg Glu Phe Val
        35                  40                  45

Ala His Ile Ser Trp Arg Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Val Tyr Tyr Cys
                85                  90                  95

Asp Ile Ala Gly Arg Arg Gly Gln Gly Thr Gln Val Thr Val Ser Ser
            100                 105                 110

```
<210> SEQ ID NO 138
<211> LENGTH: 114
<212> TYPE: PRT
<213> ORGANISM: Lama glama
<220> FEATURE:
<221> NAME/KEY: MISC_FEATURE
<223> OTHER INFORMATION: CD40-4

<400> SEQUENCE: 138
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Ser Met Tyr Trp Val Arg Gln Ala Pro Gly Lys Gly Leu Glu Trp Val
        35                  40                  45

Ser Glu Ile Tyr Pro Asp Gly Asn Gly Trp Tyr Thr Ser Ser Val Lys
    50                  55                  60

Gly Arg Phe Thr Ile Ser Arg Asp Asn Asp Lys Asn Met Leu Tyr Leu
65                  70                  75                  80

Gln Met Asn Ser Leu Lys Pro Asp Asp Thr Ala Val Tyr Tyr Cys Ala
                85                  90                  95

Leu Ser Arg Ser Gly Gln Gly Arg Gly Gln Gly Thr Arg Val Thr Val
            100                 105                 110

Ser Ser

```
<210> SEQ ID NO 139
<211> LENGTH: 111
<212> TYPE: PRT
<213> ORGANISM: Lama glama
<220> FEATURE:
<221> NAME/KEY: MISC_FEATURE
<223> OTHER INFORMATION: CD40-5

<400> SEQUENCE: 139
```

Glu Val Gln Leu Val Glu Ser Gly Gly Gly Leu Val Gln Ala Gly Gly
1               5                   10                  15

-continued

```
Ser Leu Glu Leu Ser Cys Ser Phe Gly Arg Ala Phe Asp Arg Tyr
         20                  25                  30

Phe Met Ala Trp Phe Arg Gln Ala Pro Gly Lys Gly Leu Glu Trp Val
         35                  40                  45

Ser Arg Ile Tyr Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Asn Leu Lys Pro Glu Asp Thr Ala Val Tyr Tyr Cys Asp
             85                  90                  95

Ile Ala Gly Arg Arg Gly Gln Gly Ile Gln Val Thr Val Val Ser
            100                 105                 110
```

<210> SEQ ID NO 140
<211> LENGTH: 112
<212> TYPE: PRT
<213> ORGANISM: Lama glama
<220> FEATURE:
<221> NAME/KEY: MISC_FEATURE
<223> OTHER INFORMATION: CD40-6

<400> SEQUENCE: 140

```
Glu Val Gln Leu Val Glu Ser Gly Gly Gly Leu Val Gln Ala Gly Asp
 1               5                  10                  15

Ser Leu Arg Leu Ser Cys Ala Ala Ser Gly Arg Thr Phe Asn Thr Val
             20                  25                  30

Asp Met Gly Trp Phe Arg Gln Ala Pro Gly Lys Glu Arg Glu Phe Val
         35                  40                  45

Ala His Ile Ser Trp Arg Gly Gly Ser Thr Tyr Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Asn Leu Lys Pro Glu Asp Thr Ala Val Tyr Tyr Cys
             85                  90                  95

Asp Ile Ala Gly Arg Arg Gly Gln Gly Thr Gln Val Thr Val Ser Ser
            100                 105                 110
```

<210> SEQ ID NO 141
<211> LENGTH: 114
<212> TYPE: PRT
<213> ORGANISM: Lama glama
<220> FEATURE:
<221> NAME/KEY: MISC_FEATURE
<223> OTHER INFORMATION: CD40-7

<400> SEQUENCE: 141

```
Ala Val Gln Leu Glu Glu Ser Gly Gly Asp Ser Val Gln Ala Gly Gly
 1               5                  10                  15

Ser Leu Arg Leu Ser Cys Ala Ala Ser Gly Phe Thr Phe Ser Arg Tyr
             20                  25                  30

Ser Met Tyr Trp Val Arg Gln Pro Pro Gly Lys Gly Leu Glu Trp Val
         35                  40                  45

Ser Glu Ile Tyr Pro Asp Gly Asn Gly Trp Tyr Thr Ser Ser Val Lys
 50                  55                  60

Gly Arg Phe Thr Ile Ser Arg Asp Asn Asp Lys Asn Met Leu Tyr Leu
 65                  70                  75                  80

Gln Met Asn Ser Leu Lys Pro Asp Asp Thr Ala Val Tyr Tyr Cys Ala
             85                  90                  95
```

-continued

Leu Ser Arg Ser Gly Gln Gly Arg Gly Gln Gly Thr Arg Val Thr Val
            100                 105                 110

Ser Ser

<210> SEQ ID NO 142
<211> LENGTH: 120
<212> TYPE: PRT
<213> ORGANISM: Lama glama
<220> FEATURE:
<221> NAME/KEY: MISC_FEATURE
<223> OTHER INFORMATION: MPOD6 Salmon

<400> SEQUENCE: 142

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Phe Met Asn Trp Val Arg Gln Ala Pro Gly Lys Gly Leu Glu Trp Val
            35                  40                  45

Ser Gly Ile Tyr Ser Asp Gly Ser Lys Thr Tyr Tyr Gly Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Ser Ala Val Tyr Tyr Cys
                85                  90                  95

Thr Arg Gly Thr Gly Trp Ser Ser Thr Pro Tyr Thr Tyr Arg Gly Gln
            100                 105                 110

Gly Thr Gln Val Thr Val Ser Ser
        115                 120

<210> SEQ ID NO 143
<211> LENGTH: 127
<212> TYPE: PRT
<213> ORGANISM: Lama glama
<220> FEATURE:
<221> NAME/KEY: MISC_FEATURE
<223> OTHER INFORMATION: 1-F6 RTV

<400> SEQUENCE: 143

Gln Val Gln Leu Gln Glu Val Arg Gly Arg Leu Val Gln Leu Gly Gly
1               5                   10                  15

Ser Leu Arg Leu Ser Cys Ala Ala Ser Gly Phe Thr Phe Lys Tyr Tyr
            20                  25                  30

Ala Met Ser Trp Val Arg Gln Ala Pro Gly Lys Gly Leu Glu Trp Val
            35                  40                  45

Ser Tyr Ile Asn Asp Asn Gly Gly Tyr Thr Asp Tyr Ser Asp Ser Val
        50                  55                  60

Lys Gly Arg Phe Thr Ile Ser Arg Asp Asn Ala Lys Asn Thr Leu Tyr
65                  70                  75                  80

Leu His Met Asn Arg Leu Lys Pro Glu Asp Thr Ala Val Tyr Phe Cys
                85                  90                  95

Ala Lys Trp Asp Thr Asp Ala Val Ser Ser Ser Arg Tyr Lys Thr His
            100                 105                 110

Asn Gly Asp Ile Arg Gly Pro Gly Thr Gln Val Thr Val Ser Ser
        115                 120                 125

<210> SEQ ID NO 144
<211> LENGTH: 121
<212> TYPE: PRT

<213> ORGANISM: Lama glama
<220> FEATURE:
<221> NAME/KEY: MISC_FEATURE
<223> OTHER INFORMATION: CUTIII19

<400> SEQUENCE: 144

Gln Val Gln Leu Val Glu Ser Gly Gly Gly Leu Val Gln Ala Gly Glu
1               5                   10                  15

Ser Leu Thr Leu Ser Cys Thr Ala Ser Gly Gly Ser Phe Asn Asn Trp
            20                  25                  30

His Met Gly Trp Phe Arg Gln Ala Pro Gly Thr Glu Arg Glu Phe Val
        35                  40                  45

Ala Ala Ile Arg Arg Ala Tyr Gly Ser Thr Phe Tyr Ala Asp Ser Val
    50                  55                  60

Lys Gly Arg Phe Thr Ile Ala Arg Asp Asn Ala Lys Asn Thr Val Tyr
65                  70                  75                  80

Leu Gln Met Ser Ser Leu Lys Pro Glu Asp Ser Ala Val Tyr Tyr Cys
                85                  90                  95

Ala Ala Lys Arg Ala Phe Arg Val Gly Asp Phe Glu Tyr Tyr Gly
            100                 105                 110

Gln Gly Thr Gln Val Thr Val Ser Ser
        115                 120

<210> SEQ ID NO 145
<211> LENGTH: 117
<212> TYPE: PRT
<213> ORGANISM: Camelus dromedarius
<220> FEATURE:
<221> NAME/KEY: MISC_FEATURE
<223> OTHER INFORMATION: A4cut9

<400> SEQUENCE: 145

Gln Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Tyr Met Asn Trp Val Arg Gln Ala Pro Gly Lys Gly Leu Glu Trp Val
        35                  40                  45

Pro Gly Ile Asn Lys Asp Gly Ser Val Ser His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Arg Met Asn Ser Leu Lys Ser Glu Asp Thr Ala Leu Tyr Tyr Cys
                85                  90                  95

Ala Thr Ile Ala Gly Phe Arg Val Gly Gly Pro Gly Thr Gln
            100                 105                 110

Val Thr Val Ser Ser
        115

<210> SEQ ID NO 146
<211> LENGTH: 119
<212> TYPE: PRT
<213> ORGANISM: Camelus dromedarius
<220> FEATURE:
<221> NAME/KEY: MISC_FEATURE
<223> OTHER INFORMATION: CACU13

<400> SEQUENCE: 146

Asp Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Arg Phe Asp Ser Val
            20                  25                  30

Ala Met Thr Trp Val Arg Gln Thr Pro Gly Lys Gly Leu Glu Trp Val
        35                  40                  45

Ser Ser Ile Ser Trp Asp Gly Thr Thr Ser Tyr Ala Ala Ser Val
 50                  55                  60

Lys Gly Arg Phe Thr Ile Ser Arg Asp Asn Ala Lys Asn Thr Leu Tyr
 65                  70                  75                  80

Leu Gln Leu Asp Ser Leu Lys Thr Glu Asp Thr Ala Met Tyr Tyr Cys
                85                  90                  95

Thr Lys Thr Gly Val Asp Tyr Arg Asp Ser Arg Asp Gly Arg Gly
            100                 105                 110

Thr Gln Val Thr Val Ser Ser
            115

<210> SEQ ID NO 147
<211> LENGTH: 119
<212> TYPE: PRT
<213> ORGANISM: Camelus dromedarius
<220> FEATURE:
<221> NAME/KEY: MISC_FEATURE
<223> OTHER INFORMATION: CABCUT4

<400> SEQUENCE: 147

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Arg Phe Asp Ser Val
            20                  25                  30

Ala Met Thr Trp Val Arg Gln Ala Pro Gly Lys Gly Leu Glu Trp Val
        35                  40                  45

Ser Ser Ile Ser Trp Asp Gly Thr Thr Ser Tyr Ala Ala Ser Val
 50                  55                  60

Lys Gly Arg Phe Thr Ile Ser Arg Asp Asn Ala Lys Asn Thr Leu Tyr
 65                  70                  75                  80

Leu Gln Leu Asp Ser Leu Asn Thr Glu Asp Thr Ala Met Tyr Tyr Cys
                85                  90                  95

Thr Lys Thr Gly Val Asp Tyr Arg Asp Ser Arg Ser Arg Gly Gln Gly
            100                 105                 110

Thr Gln Val Thr Val Ser Ser
            115

<210> SEQ ID NO 148
<211> LENGTH: 127
<212> TYPE: PRT
<213> ORGANISM: Camelus dromedarius
<220> FEATURE:
<221> NAME/KEY: MISC_FEATURE
<223> OTHER INFORMATION: CU16

<400> SEQUENCE: 148

Gln Val Gln Leu Val Glu Ser Gly Gly Gly Ser Val Gln Ala Gly Gly
 1               5                  10                  15

Ser Leu Lys Leu Thr Cys Glu Leu Ser Gly Phe Asn Gly Arg Ser Asn
            20                  25                  30

Cys Met Gly Trp Phe Arg Gln Val Leu Gly Lys Asp Arg Glu Gly Val
        35                  40                  45

Ala Ala Ile Asn His Pro Glu Gly Ser Glu Phe Tyr Asp Asp Ser Val
 50                  55                  60

```
Lys Gly Arg Phe Lys Ile Thr Arg Asp Gly Leu Lys Asp Ala Asp Ser
 65                  70                  75                  80

Leu Gln Met Asn Asn Leu Lys Pro Glu Asp Thr Ala Thr Tyr Tyr Cys
                 85                  90                  95

Ala Leu Arg Pro Tyr Asp Cys Tyr Ser Gly Ala Trp Ser Pro Ala Asp
            100                 105                 110

Phe Tyr Tyr Arg Gly Ala Arg Gly Thr Gln Val Thr Val Ser Ser
        115                 120                 125

<210> SEQ ID NO 149
<211> LENGTH: 116
<212> TYPE: PRT
<213> ORGANISM: Camelus dromedarius
<220> FEATURE:
<221> NAME/KEY: MISC_FEATURE
<223> OTHER INFORMATION: 48dpvy3

<400> SEQUENCE: 149

Gln Val Gln Leu Gln Ala Ser Gly Gly Gly Ser Val Glu Ala Gly Gly
1               5                   10                  15

Ser Leu Arg Leu Ser Cys Ala Ala Ser Gly Asp Thr Ala Lys Leu Asn
            20                  25                  30

Cys Met Ala Trp Phe Arg Gln Ala Pro Gly Lys Glu Arg Glu Arg Val
        35                  40                  45

Ala Ser Leu Ser Thr Arg Leu Thr Thr Thr Ser Tyr Thr Asp Ser Val
    50                  55                  60

Lys Gly Arg Phe Thr Ile Ser Gln Asp Thr Ala Thr Asn Thr Val Tyr
 65                  70                  75                  80

Leu Glu Met Asn Ser Leu Gln Pro Glu Asp Thr Ala Val Tyr Tyr Cys
                 85                  90                  95

Gln Leu Ser Arg Gly Gly Thr Asn Tyr Arg Gly Gln Gly Thr Leu Val
            100                 105                 110

Thr Val Ser Ser
        115

<210> SEQ ID NO 150
<211> LENGTH: 126
<212> TYPE: PRT
<213> ORGANISM: Camelus dromedarius
<220> FEATURE:
<221> NAME/KEY: MISC_FEATURE
<223> OTHER INFORMATION: 48DPVY16

<400> SEQUENCE: 150

Gln Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Tyr Ser Ser Asn
            20                  25                  30

Cys Met Gly Trp Phe Arg Gln Ala Leu Gly Lys Glu Arg Glu Gly Val
        35                  40                  45

Ala Ala Ile Tyr Thr Gly Gly Ser Thr Tyr Tyr Ala Asp Ser Val
    50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ser Leu Leu Pro Leu Val Ala Gly Ile Gly Val Trp Asp Ala
            100                 105                 110
```

-continued

Phe Asp Tyr Arg Gly Gln Gly Thr Gln Val Thr Val Ser Ser
            115                 120                 125

<210> SEQ ID NO 151
<211> LENGTH: 127
<212> TYPE: PRT
<213> ORGANISM: Camelus dromedarius
<220> FEATURE:
<221> NAME/KEY: MISC_FEATURE
<223> OTHER INFORMATION: 48DPVY10

<400> SEQUENCE: 151

Gln Val Gln Leu Gln Ala Ser Gly Gly Gly Ser Val Gln Ala Gly Gly
1               5                   10                  15

Ser Leu Arg Leu Ser Cys Val Ala Ser Gln Tyr Glu Tyr Ser Asn Asn
            20                  25                  30

Tyr Ile Ala Trp Phe Arg Gln Ala Pro Gly Lys Glu Arg Glu Gly Val
        35                  40                  45

Ala Ala Ile Tyr Thr Gly Gly Val Thr Arg Ala Ser Pro Tyr Tyr Ala
    50                  55                  60

Asp Pro Val Lys Gly Arg Phe Ser Ile Ser Lys Asp Asn Ala Lys Asn
65                  70                  75                  80

Thr Val Tyr Leu Gln Met Asn Asp Leu Lys Pro Glu Asp Ser Gly Thr
                85                  90                  95

Tyr Ile Cys Ala Ser Ser Ile His Gly Leu Gly Asn Pro Leu Arg Ser
            100                 105                 110

Glu Phe Ser Tyr Tyr Gly Gln Gly Thr Leu Val Thr Val Ser Ser
        115                 120                 125

<210> SEQ ID NO 152
<211> LENGTH: 123
<212> TYPE: PRT
<213> ORGANISM: Camelus dromedarius
<220> FEATURE:
<221> NAME/KEY: MISC_FEATURE
<223> OTHER INFORMATION: 48DPVY23

<400> SEQUENCE: 152

Gln Val Gln Leu Gln Ala Ser Gly Gly Gly Ser Val Glu Ala Gly Gly
1               5                   10                  15

Ser Leu Arg Leu Ser Cys Ala Ala Ser Gly Asp Thr Ala Lys Leu Asn
            20                  25                  30

Cys Met Ala Trp Phe Arg Gln Ala Pro Gly Lys Glu Arg Glu Arg Val
        35                  40                  45

Ala Leu Leu Ser Thr Arg Leu Thr Thr Thr Ser Tyr Thr Asp Ser Val
    50                  55                  60

Lys Gly Arg Phe Thr Ile Ser Gln Asp Thr Ala Thr Asn Thr Val Tyr
65                  70                  75                  80

Leu Glu Met Asn Ser Leu Gln Pro Glu Asp Thr Ala Ile Tyr Tyr Cys
                85                  90                  95

Ala Ala Arg Trp Ala Gly Arg Ser Cys Leu Val Ser Val Tyr Asp Tyr
            100                 105                 110

Tyr Gly Gln Gly Thr Leu Val Thr Val Ser Ser
        115                 120

<210> SEQ ID NO 153
<211> LENGTH: 125
<212> TYPE: PRT
<213> ORGANISM: Camelus dromedarius -continued

```
<220> FEATURE:
<221> NAME/KEY: MISC_FEATURE
<223> OTHER INFORMATION: PVYIA15

<400> SEQUENCE: 153

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Lys Ser Gly Gly Gly Arg Thr Tyr Tyr Ala Asp Ser Val
    50                  55                  60

Lys Gly Arg Phe Thr Ile Ser Arg Asp Asn Ala Lys Asn Thr Leu Thr
65                  70                  75                  80

Leu Gln Leu Asn Ser Leu Lys Thr Glu Asp Thr Ala Met Tyr Tyr Cys
                85                  90                  95

Ala Lys Gly Ala Arg Tyr Asp Ser Asp Tyr Asp Val Thr Trp Leu Asp
            100                 105                 110

Ser Tyr Ser Gly Gln Gly Thr Gln Val Thr Val Ser Ser
        115                 120                 125

<210> SEQ ID NO 154
<211> LENGTH: 117
<212> TYPE: PRT
<213> ORGANISM: Camelus dromedarius
<220> FEATURE:
<221> NAME/KEY: MISC_FEATURE
<223> OTHER INFORMATION: PVYIA2

<400> SEQUENCE: 154

Asp Val Gln Leu Val Glu Ser Gly Gly Gly Ser Val Gln Ala Gly Gly
1               5                   10                  15

Ser Leu Arg Leu Ser Cys Thr Ala Ser Gly Leu Arg Leu Asn Thr Tyr
            20                  25                  30

His Met Ser Trp Val Arg Gln Ala Pro Gly Lys Gly Leu Glu Trp Val
        35                  40                  45

Ser Thr Ile Tyr Ile Gly Gly Thr Thr Thr Ser His Ala Asn Ser Val
    50                  55                  60

Ser Gly Arg Phe Thr Ile Ser Arg Asp Asp Ala Lys Asn Thr Leu Tyr
65                  70                  75                  80

Leu Gln Met Asn Asn Leu Lys Pro Glu Asp Thr Ala Val Tyr Phe Cys
                85                  90                  95

Ala Thr Gly Ser Val Asn Ala Tyr Gly Val Lys Gly Gln Gly Thr Gln
            100                 105                 110

Val Thr Val Ser Ser
        115

<210> SEQ ID NO 155
<211> LENGTH: 119
<212> TYPE: PRT
<213> ORGANISM: Camelus dromedarius
<220> FEATURE:
<221> NAME/KEY: MISC_FEATURE
<223> OTHER INFORMATION: PVYIA1

<400> SEQUENCE: 155

Gln Val Gln Leu Val Glu Ser Gly Gly Gly Ser Val Gln Ala Gly Gly
1               5                   10                  15
```

```
Ser Leu Thr Leu Ser Cys Thr Val Ser Gly Tyr Asp Phe Asn Arg Cys
            20                  25                  30

Ser Met Asn Trp Tyr Arg Glu Asn Pro Gly Lys Glu Arg Glu Phe Val
        35                  40                  45

Ala Gly Ile Asp Ser Asp Gly Thr Thr Thr Tyr Ala Asp Ser Val Lys
 50                  55                  60

Gly Arg Phe Thr Ile Ser His Asp Asn Thr Arg Asn Thr Leu Tyr Leu
 65                  70                  75                  80

Gln Met Asn Ser Leu Lys Ser Glu Asp Thr Ala Leu Tyr Tyr Cys Arg
                85                  90                  95

Leu Gly Gly Leu Arg Thr Trp Pro Gln Tyr Gly Tyr Arg Gly Gln Gly
            100                 105                 110

Thr Gln Val Thr Val Ser Ser
            115

<210> SEQ ID NO 156
<211> LENGTH: 119
<212> TYPE: PRT
<213> ORGANISM: Camelus dromedarius
<220> FEATURE:
<221> NAME/KEY: MISC_FEATURE
<223> OTHER INFORMATION: PVY17

<400> SEQUENCE: 156

Gln Val Gln Leu Val Glu Ser Gly Gly Gly Leu Val Gln Pro Gly Gly
 1               5                  10                  15

Ser Leu Arg Leu Ser Cys Thr Ala Ser Gly Leu Arg Leu Asn Thr Tyr
            20                  25                  30

His Met Ser Trp Val Arg Gln Ala Pro Gly Lys Gly Leu Glu Trp Val
        35                  40                  45

Ser Thr Ile Tyr Ile Gly Gly Thr Thr Ser His Ala Asn Ser Val
 50                  55                  60

Ser Gly Arg Phe Thr Ile Ser Arg Asp Ala Lys Asn Thr Leu Tyr
 65                  70                  75                  80

Leu Gln Met Asn Asn Leu Lys Pro Glu Asp Thr Ala Val Tyr Phe Cys
                85                  90                  95

Ala Thr Gly Ser Val Asn Ala Tyr Gly Val Lys Gly Gln Gly Thr Leu
            100                 105                 110

Val Thr Val Ser Ser Ala Ala
            115

<210> SEQ ID NO 157
<211> LENGTH: 124
<212> TYPE: PRT
<213> ORGANISM: Camelus dromedarius
<220> FEATURE:
<221> NAME/KEY: MISC_FEATURE
<223> OTHER INFORMATION: 1D2L28

<400> SEQUENCE: 157

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Ser Ile Tyr
            20                  25                  30

Arg Met Ser Trp Val Arg Gln Ala Pro Gly Gln Gly Leu Glu Trp Val
        35                  40                  45

Ser Ser Ile Asp Ser Gly Gly Gly Ile Thr Tyr Tyr Ala Asp Ser Val
 50                  55                  60
```

```
Lys Gly Arg Phe Thr Ile Ser Arg Asp Asn Ala Lys Asn Thr Leu Tyr
 65                  70                  75                  80

Leu Gln Leu Asn Ser Leu Lys Thr Glu Asp Thr Ala Met Tyr Tyr Cys
                 85                  90                  95

Ala Arg Gly His Tyr Leu Tyr Asp Asp Ile Phe Thr Gly Ala Lys
            100                 105                 110

Gly Gln Gly Thr Gln Val Thr Val Ser Ser Gly Arg
            115                 120

<210> SEQ ID NO 158
<211> LENGTH: 98
<212> TYPE: PRT
<213> ORGANISM: Homo sapiens
<220> FEATURE:
<221> NAME/KEY: MISC_FEATURE
<223> OTHER INFORMATION: DP-47 (a human VH3 germline)

<400> SEQUENCE: 158

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 159
<211> LENGTH: 27
<212> TYPE: DNA
<213> ORGANISM: Artificial Sequence
<220> FEATURE:
<223> OTHER INFORMATION: first mutagenic primer (in example 5)

<400> SEQUENCE: 159
acccgaggag cctgggacca gtggcag                                      27

<210> SEQ ID NO 160
<211> LENGTH: 27
<212> TYPE: DNA
<213> ORGANISM: Artificial Sequence
<220> FEATURE:
<223> OTHER INFORMATION: second mutagenic primer (in example 5)

<400> SEQUENCE: 160
accccggtga ggagggtcca gtggcag                                      27

<210> SEQ ID NO 161
<211> LENGTH: 37
<212> TYPE: DNA
<213> ORGANISM: Artificial Sequence
<220> FEATURE:
<223> OTHER INFORMATION: upper strand of first double stranded primer
      (in example 5)
<220> FEATURE:
<221> NAME/KEY: misc_feature
<222> LOCATION: (1)..(1)
<223> OTHER INFORMATION: c is phosphorylated
```

```
<400> SEQUENCE: 161
cgtcaggggc caaggaaccc aggtcaccgt ctcctca                              37

<210> SEQ ID NO 162
<211> LENGTH: 39
<212> TYPE: DNA
<213> ORGANISM: Artificial Sequence
<220> FEATURE:
<223> OTHER INFORMATION: lower strand of first double stranded primer
      (in example 5)

<400> SEQUENCE: 162
tgaggagacg gtgacctggg tccctggcc cctgacgtc                             39

<210> SEQ ID NO 163
<211> LENGTH: 33
<212> TYPE: DNA
<213> ORGANISM: Artificial Sequence
<220> FEATURE:
<223> OTHER INFORMATION: upper strand of second double stranded primer
      (in example 5)
<220> FEATURE:
<221> NAME/KEY: misc_feature
<222> LOCATION: (1)..(1)
<223> OTHER INFORMATION: a is phosphorylated

<400> SEQUENCE: 163
aggggccaag gaacccaggt caccgtctcc tca                                  33

<210> SEQ ID NO 164
<211> LENGTH: 35
<212> TYPE: DNA
<213> ORGANISM: Artificial Sequence
<220> FEATURE:
<223> OTHER INFORMATION: lower strand of second double stranded primer
      (in example 5)

<400> SEQUENCE: 164
tgaggagacg gtgacctggg tccctggcc ccttg                                 35

<210> SEQ ID NO 165
<211> LENGTH: 30
<212> TYPE: DNA
<213> ORGANISM: Artificial Sequence
<220> FEATURE:
<223> OTHER INFORMATION: backward primer (in example 5)

<400> SEQUENCE: 165
ctgggtccag tggcagagga gtcgccggcg                                      30
```